(12) United States Patent
Huang et al.

(10) Patent No.: US 12,578,344 B2
(45) Date of Patent: Mar. 17, 2026

(54) COMPOSITIONS, KITS, AND METHODS FOR DETECTING PRECLINICAL ALZHEIMER'S DISEASE

(71) Applicant: NeuroQuest Ltd., Karmiel (IL)

(72) Inventors: Xin Huang, Mernda (AU); Yihan Li, Parkville (AU); James Doecke, Tamborine (AU); Baijun Gu, Mernda (AU); Michal Eisenbach-Schwartz, Rehovot (IL)

(73) Assignee: NEUROQUEST LTD., Misgav Business Park (IL)

( * ) Notice: Subject to any disclaimer, the term of this patent is extended or adjusted under 35 U.S.C. 154(b) by 0 days.

(21) Appl. No.: 17/882,671

(22) Filed: Aug. 8, 2022

(65) Prior Publication Data

US 2023/0054073 A1    Feb. 23, 2023

Related U.S. Application Data

(60) Provisional application No. 63/231,034, filed on Aug. 9, 2021.

(51) Int. Cl.
*G01N 33/58*      (2006.01)
*C07K 16/28*      (2006.01)
*G01N 33/68*      (2006.01)

(52) U.S. Cl.
CPC ....... *G01N 33/582* (2013.01); *C07K 16/2803* (2013.01); *G01N 33/6896* (2013.01); *C07K 2317/30* (2013.01)

(58) Field of Classification Search
CPC ............. G01N 33/582; G01N 33/6896; G01N 2800/2821; C07K 16/2803; C07K 2317/30

(Continued)

(56) References Cited

U.S. PATENT DOCUMENTS 4,444,879 A * 4/1984 Foster ................ G01N 33/6854
                                                                    435/805
5,426,029 A   6/1995 Rittershaus et al.
                        (Continued)

FOREIGN PATENT DOCUMENTS

JP        2010510492 A    4/2010
WO        03/100419 A1    12/2003
                        (Continued)

OTHER PUBLICATIONS

Shinohara M, Tachibana M, Kanekiyo T, Bu G. Role of LRP1 in the pathogenesis of Alzheimer's disease: evidence from clinical and preclinical studies. J Lipid Res. Jul. 2017;58(7):1267-1281. (Year: 2017).*

(Continued)

*Primary Examiner* — Christopher L Chin
*Assistant Examiner* — Ellis Follett Lusi
(74) *Attorney, Agent, or Firm* — Wilson Sonsini Goodrich & Rosati

(57)    ABSTRACT

Compositions and kits for diagnosing and prognosing Alzheimer's Disease (AD) in a human patient include a binding agent such as a monoclonal antibody for a bio-marker conjugated to a detectable moiety such as a fluoro-phore, wherein the biomarker is chosen from CD163, CD91, CD59, MerTK and other phagocytosis-related molecules. Further compositions and kits employ panels of fluorophore-conjugated monoclonal antibodies for biomarkers including scavenger receptors. Methods for determining the relative expression of biomarkers, diagnosing AD, and determining the efficacy of AD therapeutic candidates such as phagocy-tosis-promoting agents and scavenger receptor agonists also appear.

24 Claims, 1 Drawing Sheet

(58) Field of Classification Search

USPC ....................................................... 435/7.24

See application file for complete search history.

(56) References Cited

U.S. PATENT DOCUMENTS

| | | | |
|---|---|---|---|
| 7,741,046 | B2 | 6/2010 | Larsen et al. |
| 9,240,043 | B2 | 1/2016 | Christiansen et al. |
| 9,579,346 | B2 | 2/2017 | McGrath et al. |
| 2008/0118916 | A1* | 5/2008 | Sood .................... G01N 33/542 |
| | | | 435/6.14 |
| 2013/0230499 | A1 | 9/2013 | Eisenbach-Schwartz et al. |
| 2015/0057176 | A1 | 2/2015 | Eisenbach-Schwartz et al. |
| 2015/0209404 | A1 | 7/2015 | Eisenbach-Schwartz et al. |
| 2024/0069042 | A1 | 2/2024 | Huang et al. |

FOREIGN PATENT DOCUMENTS

| | | | | |
|---|---|---|---|---|
| WO | WO-2006090096 | A1 * | 8/2006 | .............. G01N 1/30 |
| WO | 2007/136782 | A2 | 11/2007 | |
| WO | WO-2008133759 | A2 | 11/2008 | |
| WO | 2011/111043 | A1 | 9/2011 | |
| WO | 2013/144957 | A1 | 10/2013 | |
| WO | 2023/017513 | A1 | 2/2023 | |

OTHER PUBLICATIONS

Wood, B.L. (2013). Flow Cytometric Monitoring of Residual Disease in Acute Leukemia. In: Czader, M. (eds) Hematological Malignancies. Methods in Molecular Biology, vol. 999. Humana Press, Totowa, NJ. (Year: 2013).*

Wolf et al. Monocyte cholesterol homeostasis correlates with the presence of detergent resistant membrane microdomains. Cytometry A. Jul. 2007;71(7):486-94. (Year: 2007).*

BD Biosciences. BD Lyoplate Human Cell Surface Marker Screening Panel. Technical Data Sheet. 560747 Rev. 7. Feb. 2020. (Year: 2020).*

Humphries et al. The use of flow cytometry to detect expression of subunits encoded by 11 Salmonella enterica serotype Typhimurium fimbrial operons. Mol Microbiol. Jun. 2003;48(5):1357-76. (Year: 2003).*

Hoffman et al. High-Content Immunophenotyping and Hierarchical Clustering Reveal Sources of Heterogeneity and New Surface Markers of Human Blood Monocyte Subsets. Thromb Haemost. Jan. 2020; 120(1):141-155. (Year: 2020).*

Mamo, J. C. L. et al., 'Plasma lipoprotein β-amyloid in subjects with Alzheimer's disease or mild cognitive impairment,' Annals of Clinical Biochemistry, 2008, 45, 395-403.

2020 Alzheimer's disease facts and figures, Alzheimers Association Report, Alzheimer's Dement., vol. 16 (2020) 391-460 (70 pages).

Arancio O. et al., 'RAGE potentiates Aβ-induced perturbation of neuronal function in transgenic mice,' The EMBO Journal, vol. 23, 2004 (10 pages).

Baruch K. et al, 'Aging-induced type I interferon signaling at the choroid plexus negatively affects brain function,' Science, Oct. 3, 2014, 346(6205), 89-93 (9 pages).

Baruch K. et al., 'PD-1 immune checkpoint blockade reduces pathology and improves memory in mouse models of Alzheimer's disease,' Nature Medicine, vol. 22, Feb. 2016, 135-39 (5 pages).

Baum L. et al., 'Low density lipoprotein receptor related protein gene exon 3 polymorphism association with Alzheimer's disease in Chinese,' Elsevier, Neuroscience Letters 247, 1998, 33-36 (4 pages).

A. M. Blom, 'The role of complement inhibitors beyond controlling inflammation,' The Association for the Publication of the Journal of Internal Medicine, 2017, 116-28 (13 pages).

Bourgeat P. et al., 'Comparison of MR-less PiB SUVR quantification methods,' Elsevier, Neurobiology of Aging 36, 2015, S159-66 (8 pages).

Bourgeat P. et al., 'Implementing the centiloid transformation for 11C-PiB and β-amyloid 18F-PET tracers using CapAIBL,' Elsevier, NeuroImage 183, 2018, 387-393 (7 pages).

Bradshaw E. M. et al., 'CD33 Alzheimer's disease locus: Altered monocyte function and amyloid biology,' Nat Neurosci. Jul. 2013; 16(7): 848-850 (14 pages).

G. W. Brier, 'Verification of Forecasts Expressed in Terms of probability,' Monthly Weather Review, vol. 78, No. 1, Jan. 1950 (3 pages).

Cheng Y. et al., 'Peripheral clearance of brain-derived Aβ in Alzheimer's disease: pathophysiology and therapeutic perspectives,' Translational Neurodegeneration, 2020 (11 pages).

Coraci I. S. et al., 'CD36, a Class B Scavenger Receptor, Is Expressed on Microglia in Alzheimer's Disease Brains and Can Mediate Production of Reactive Oxygen Species in Response to β-Amyloid Fibrils,' American Journal of Pathology, vol. 160, No. 1, Jan. 2002, 101-112 (12 pages).

Deane R. et al., 'RAGE mediates amyloid-β peptide transport across the blood-brain barrier and accumulation in brain,' Nature Medicine, vol. 9, No. 7, Jul. 2003, 907-913 (7 pages).

Dubois B. et al., 'Preclinical Alzheimer's disease: Definition, natural history, and diagnostic criteria,' Alzheimers Dement. Mar. 2016, 12(3): 292-323 (56 pages).

Endemann G. et al., 'CD36 Is a Receptor for Oxidized Low Density Lipoprotein,' The Journal of Biological Chemistry, vol. 268, No. 16, Issue of Jun. 5, 1993, 11811-11816 (6 pages).

Fagan A. M. et al., 'Longitudinal change in CSF biomarkers in autosomal-dominant Alzheimer disease,' Sci Transl Med., Mar. 5, 2014, 6(226) (35 pages).

Fossati S. et al., 'Plasma tau complements CSF tau and P-tau in the diagnosis of Alzheimer's disease,' Elsevier, Alzheimers & Dementia: Diagnosis, Assessment & Disease Monitoring 11, 2019, 483-492 (10 pages).

Fourgeaud L. et al., 'TAM receptors regulate multiple features of microglial physiology,' Nature, Apr. 14, 2016, 532 (7598): 240-244 (24 pages).

Fowler C. et al., 'Fifteen Years of the Australian Imaging, Biomarkers and Lifestyle (AIBL) Study: Progress and Observations from 2,359 Older Adults Spanning the Spectrum from Cognitive Normality to Alzheimer's Disease,' Journal of Alzheimer's Disease Reports 5, 2021, 443-468 (26 pages).

Frenkel D. et al., 'Scara1 deficiency impairs clearance of soluble Amyloid-β by mononuclear phagocytes and accelerates Alzheimer's-like disease progression,' Nat Commun. vol. 4 (2013) 2030 (19 pages).

Gal., 'Mutations in MERTK, the human orthologue of the RCS rat retinal dystrophy gene, cause retinitis pigmentosa,' Nature Genetics, vol. 26, Nov. 2000, 270-271 (2 pages).

Gu B. J. et al., 'Innate phagocytosis by peripheral blood monocytes is altered in Alzheimer's disease,' Acta Neuropathology, 2016, 132, 377-389 (13 pages).

Ho Y.H. et al., 'Remodeling of Bone Marrow Hematopoietic Stem Cell Niches Promotes Myeloid Cell Expansion during Premature or Physiological Aging,' Cell Stem Cell 25, Sep. 5, 2019, 407-418. e1-e6 (19 pages).

Hollenbach E. et al., 'Confirmation of an association between a polymorphism in exon 3 of the lowdensity lipoprotein receptor-related protein gene and Alzheimer's disease,' American Academy of Neurology, 1998, 1905-1908 (4 pages).

Huang K. L. et al., 'A common haplotype lowers PU.1 expression in myeloid cells and delays onset of Alzheimer's disease,' Nature Neuroscience, vol. 20, No. 8, Aug. 2017, 1052-1066 (15 pages).

Jack Jr. C. R. et al., 'A/T/N: An unbiased descriptive classification scheme for Alzheimer disease biomarkers,' American Academy of Neurology, 2016, 87, 539-547 (9 pages).

Janelidze S. et al., 'Associations of Plasma Phospho-Tau217 Levels With Tau Positron Emission Tomography in Early Alzheimer Disease,' JAMA Neurol. 2021, 78(2), 149-156 (8 pages).

Jiang Y. et al., 'Large-scale plasma proteomic profiling identifies a high-performance biomarker panel for Alzheimer's disease screening and staging,' The Journal of the Alzheimers Association, Alzheimer's Dement. 2021, 1-15 (15 pages).

Klickstein L. B. et al., 'Identification of Distinct C3b and C4b Recognition Sites in the Human C3b/C4b Receptor (CRI, CD35) by Deletion Mutagenesis,' The Rockefeller University Press, vol. 168, Nov. 1988, 1699-1717 (19 pages).

(56) References Cited

OTHER PUBLICATIONS

Klunk W. E. et al., 'The Centiloid Project: Standardizing Quantitative Amyloid Plaque Estimation by PET,' Alzheimers Dement., Jan. 2015, 11(1): 1-15.e4. (31 pages).

Kounnas M. C. et al., 'LDL Receptor-Related Protein, a Multifunctional ApoE Receptor, Binds Secreted I-Amyloid Precursor Protein and Mediates Its Degradation,' Cell, vol. 82, 331-340, Jul. 28, 1995 (10 pages).

Kunis G. et al., 'IFN-c-dependent activation of the brain's choroid plexus for CNS immune surveillance and repair,' BRAIN: A Journal of Neurology, 2013, 136, 3427-3440 (14 pages).

Gu, B.J. et al., "The P2X7-nonmuscle myosin membrane complex regulates phagocytosis of nonopsonized particles and bacteria by a pathway attenuated by extracellular ATP," Blood, 115, (2010) 1621-31.

Becker, S. et al., "Decreased CD11b expression, phagocytosis, and oxidative burst in urban particulate pollution-exposed human monocytes and alveolar macrophages," Journal of Toxicology & Environmental Health Part A 55, (1998) 455-477.

Chazotte, B., "Labeling the Plasma Membrane with TMA-DPH," Cold Spring Harbor Laboratory Press (2011) 567-570.

Choucair-Jaafar, N. et al., "Complement receptor 3 (CD11b/CD18) is implicated in the elimination of b-amyloid peptides," Fundamental & Clinical Pharmacology 25 (2011) 115-122.

Deane, R. et al., "A multimodal RAGE-specific inhibitor reduces amyloid β-mediated brain disorder in a mouse model of Alzheimer disease," The Journal of Clinical Investigation, vol. 122, No. 4, (2012) 1377-1392.

Debacq-Chainiaux, F. et al., "Protocols to detect senescence-associated beta-galactosidase (SA-βgal) activity, a biomarker of senescent cells in culture and in vivo," Nature Protocols, vol. 4, No. 12, (2009) 1798-1806.

Dobri, A. M. et al., "CD36 in Alzheimer's Disease: An Overview of Molecular Mechanisms and Therapeutic Targeting," Neuroscience 453, (2021) 301-311.

Fallman, M. et al., "Signaling properties of CR3 (CD11b/CD18) and CR1 (CD35) in relation to phagocytosis of complement-opsonized particles," The Journal of Immunology, vol. 151, (1993) 330-338.

Giunta, M. et al., "The leukocyte expression of CD36 is low in patients with Alzheimer's disease and mild cognitive Impairment," Neurobiology of Aging 28, (2007) 515-518.

Gu, B. J. et al., "P2X7 receptor-mediated scavenger activity of mononuclear phagocytes toward non-opsonized particles and apoptotic cells is inhibited by serum glycoproteins but remains active in cerebrospinal fluid," The Journal of Biological Chemistry, vol. 287, No. 21, (2012) 17318-17330.

Gu, B. J. et al., "A Quantitative Method for Measuring Innate Phagocytosis by Human Monocytes Using Real-Time Flow Cytometry," Cytometry Part A, 85A, (2014) 313-321.

Gu, B.J. et al., "P2X7 as a scavenger receptor for innate phagocytosis in the brain," British Journal of Pharmacology 175, (2018) 4195-4208.

Hu, N. et al., "Decreased expression of CD33 in peripheral mononuclear cells of Alzheimer's disease patients," Neuroscience Letters 563, (2014) 51-54.

Ida, N. et al., "Analysis of Heterogeneous bA4 Peptides in Human Cerebrospinal Fluid and Blood by a Newly Developed Sensitive Western Blot Assay," The Journal of Biological Chemistry, vol. 271, No. 37, (1996) 22908-22914.

Jay, T. R. et al., "TREM2 deficiency eliminates TREM2+ inflammatory macrophages and ameliorates pathology in Alzheimer's disease mouse models," The Journal of Experimental Medicine, vol. 212, No. 3, (2015) 287-295.

Jhang, K. A. et al., "Sulforaphane rescues amyloid-beta peptide-mediated decrease in MerTK expression through its anti-inflammatory effect in human THP-1 macrophages," Journal of Neuroinflammation 15, 75 (2018).

Karch, C. M. et al., "Alzheimer's Disease Genetics: From the bench to the clinic," Neuron; 83(1), (2014) 11-26.

Li, X. et al., "Prostaglandin E2 receptor subtype 2 regulation of scavenger receptor CD36 modulates microglial Abeta42 phagocytosis," The American Journal of Pathology 185, (2015) 230-239.

Linehan, E. et al., "Aging impairs peritoneal but not bone marrow-derived macrophage phagocytosis," Aging Cell 13, (2014) 699-708.

Lukacsi, S. et al., "The role of CR3 (CD11b/CD18) and CR4 (CD11c/CD18) in complement-mediated phagocytosis and podosome formation by human phagocytes," Immunology Letters 189, (2017) 64-72.

Mcgeer, P. L. et al., "Detection of the Membrane Inhibitor of Reactive Lysis (Cd59) in Diseased Neurons of Alzheimer Brain," Brain Research, 544 (1991) 315-319.

Miles, L. A. et al., "Small Molecule Binding to Alzheimer Risk Factor CD33 Promotes Abeta Phagocytosis," iScience 19, (2019) 110-118.

Pey, P. et al., "CD163: a marker of alternative microglial activation in Alzheimer's disease," Brain Pathology 20, (2010) 22.

Pey, P. et al., "Phenotypic profile of alternative activation marker CD163 is different in Alzheimer's and Parkinson's disease," Acta Neuropathologica Communications, 2:21, (2014).

Pierce, A. M. et al., TAM receptor tyrosine kinases: Expression, disease and oncogenesis in the central nervous system, Brain Res, 1542, (2014) 206-220.

Sanchez-Mico, M. V. et al., "Amyloid-β impairs the phagocytosis of dystrophic synapses by astrocytes in Alzheimer's disease," Glia, (2021) 997-1011.

Sandor, N. et al., "CD11c/CD18 Dominates Adhesion of Human Monocytes, Macrophages and Dendritic Cells over CD11b/CD18," PLOS One, (2016).

Sanz, J. M. et al., "Activation of microglia by amyloid β requires P2X7 receptor expression," The Journal of Immunology, 182, (2009) 4378-4385.

Schulz, B. et al., "Beta-amyloid (Abeta40, Abeta42) binding to modified LDL accelerates macrophage foam cell formation," Biochimica et Biophysica Acta, 1771, (2007) 1335-1344.

Sokolowski, J. D. et al., "Phagocytic Clearance in Neurodegeneration," The American Journal of Pathology, vol. 178, No. 4, (2011) 1416-1428.

Thal, L. J. et al. "The Role of Biomarkers in Clinical Trials for Alzheimer Disease," Alzheimer Dis Assoc Disord., (2006) 6-15.

Wang, Y. et al., "TREM2 lipid sensing sustains microglia response in an Alzheimer's disease model," Cell, 160, (2015) 1061-1071.

Wilhelmus, M. M. et al., "Lipoprotein Receptor-Related Protein-1 Mediates Amyloid-B-Mediated Cell Death of Cerebrovascular Cells," The American Journal of Pathology, vol. 171, No. 6, (2007) 1989-1999.

Yang, L. B. et al., "Deficiency of complement defense protein CD59 may contribute to neurodegeneration in Alzheimer's disease," The Journal of Neuroscience, vol. 20, (2000) 7505-7509.

Yang, L. B. et al., "Decrease of complement defense protein CD59 in neurons of Alzheimer's disease and high pathology control brains," Neurobiology of Aging 23, (2002) S228.

Yu, Y. et al., "Microglial Aβ Receptors in Alzheimer's Disease," Cell Mol Neurobiol., vol. 35, (2015) 71-83.

Zhao, L., "CD33 in Alzheimer's Disease—Biology, Pathogenesis, and Therapeutics: A Mini-Review," Gerontology 65, (2019) 323-331.

Zhu, X. et al., "Impacts of CR1 genetic variants on cerebrospinal fluid and neuroimaging biomarkers in alzheimer's disease," BMC Medical Genetics 21:181 (2020).

Jeynes, B. et al., "Evidence for altered LRP/RAGE expression in Alzheimer lesion pathogenesis," Current Alzheimer Research, vol. 5, No. 5, (2008) 432-437.

International Search Report and Written Opinion for PCT/IL2022/050865 dated Nov. 18, 2022 (12 pages).

Huang et al., Leukocyte surface biomarkers implicate deficits of innate immunity in sporadic Alzheimer's disease, Alzheimer's & Dementia, Nov. 9, 2022, 1-11. https://doi.org/10.1002/alz.12813.

Phitonex NovaFuor Conjugation Kit Protocol, accessed 2021, (2 pages).

PrabhuDas et al., "Standardizing Scavenger Receptor Nomenclature," J. Immunol. 2014, 192(5): 1997-2006.

(56)  References Cited

OTHER PUBLICATIONS

Lambert, J. C. et al., 'Genome-wide association study identifies variants at CLU and CR1 associated with Alzheimer's disease,' Nature Genetics, vol. 41, No. 10, Oct. 2009, 1094-1100 (7 pages).

Lendon, C. L. et al., 'Genetic association studies between dementia of the Alzheimer's type and three receptors for apolipoprotein E in a Caucasian population,' Elselvier, Neuroscience Letters 222, 1997, 187-190 (4 pages).

Lim, Y. et al., 'Effect of amyloid on memory and non-memory decline from preclinical to clinical Alzheimer's disease,' Brain: A Journal of Neurology, 2014, 221-231 (11 pages).

Lim, Y. et al., 'Sensitivity of composite scores to amyloid burden in preclinical Alzheimer's disease: Introducing the Z-scores of Attention, Verbal fluency, and Episodic memory for Nondemented older adults composite score,' Elselvier, Alzheimers & Dementia: Diagnosis, Assessment, and Disease Monitoring 2, 2016, 19-26 (8 pages).

Masters, C. L. et al., 'Alzheimer's disease,' Nature Reviews: Disease Primers vol. 1, 2015 (18 pages).

McKhann, G. M. et al., 'The diagnosis of dementia due to Alzheimer's disease: Recommendations from the National Institute on Aging-Alzheimer's Association work groups on diagnostic guidelines for Alzheimer's disease,' Alzheimers Dement., May 2011, 7(3): 263-269 (11 pages).

Naj, A. C. et al., 'Common variants in MS4A4/MS4A6E, CD2uAP, CD33, and EPHA1 are associated with late-onset Alzheimer's disease,' Nat Genet., May 2011, 43(5): 436 441 (17 pages).

Nakamura, A. et al., 'High performance plasma amyloid-β biomarkers for Alzheimer's disease,' Nature, vol. 554, Feb. 8, 2018, 249-272 (24 pages).

Pang, W. W. et al., 'Human bone marrow hematopoietic stem cells are increased in frequency and myeloid-biased with age,' PNAS, vol. 108, No. 50, Dec. 13, 2011, 20012-20017 (6 pages).

Pencina, M. J. et al., 'Evaluating the added predictive ability of a new marker: From area under the ROC curve to reclassification and beyond,' Statistics in Medicine: Statist. Med. 2008, 27:157-172 (16 pages).

Phongpreecha, T. et al., 'Single-cell peripheral immunoprofiling of Alzheimer's and Parkinson's diseases,' Science Advances: Diseases and Disorders, 2020 (11 pages).

Pickering, J. W. et al., 'New Metrics for Assessing Diagnostic Potential of Candidate Biomarkers,' www.cjasn.org vol. 7, Aug. 2012 (13 pages).

Raposo, C. et al., 'CNS Repair Requires Both Effector and Regulatory T Cells with Distinct Temporal and Spatial Profiles,' The Journal of Neuroscience, Jul. 30, 2014, 34(31):10141-10155 (15 pages).

Razai-Zadeh, K. et al., 'Can peripheral leukocytes be used as Alzheimer's disease biomarkers?,' Expert Rev Neurother., Nov. 2009, 9(11): 1623-1633 (18 pages).

Roberts, K. F. et al., 'Amyloid-β efflux from the CNS into the plasma,' Ann Neurol., Dec. 2014, 76(6): 837-844 (17 pages).

Rowe, C. C. et al., 'Amyloid imaging results from the Australian Imaging, Biomarkers and Lifestyle (AIBL) study of aging,' Elselvier, Neurobiology of Aging 31, 2010, 1275-1283 (9 pages).

Sampath, P. et al., 'Monocyte Subsets: Phenotypes and Function in Tuberculosis Infection,' Frontiers in Immunology, vol. 9, Article 1726, Jul. 2018 (8 pages).

Scheltens, P. et al., 'Alzheimer's Disease,' www.thelancet.com, vol. 388, Jul. 30, 2016, 505-17 (13 pages).

Sperling, R. A. et al., 'Toward defining the preclinical stages of Alzheimer's disease: Recommendations from the National Institute on Aging-Alzheimer's Association workgroups on diagnostic guidelines for Alzheimer's disease,' Alzheimers Dement., May 2011, 7(3): 280-292 (24 pages).

Sperling, R. A. et al., 'Association of Factors With Elevated Amyloid Burden in Clinically Normal Older Individuals,' JAMA Neurol., Jun. 2020, 77(6): 1-11 (25 pages).

Stewart, C. R. et al., 'CD36 ligands promote sterile inflammation through assembly of a Toll-like receptor 4 and 6 heterodimer,' Nat Immunol., Feb. 2010, 11(2): 155-161 (18 pages).

Steyerberg, E. W. et al., 'Assessing the performance of prediction models: a framework for some traditional and hovel measures,' Epidemiology, Jan. 2010, 21(1): 128-138 (21 pages).

Tansey, K. E. et al., 'Genetic risk for Alzheimer's disease is concentrated in specific macrophage and microglial transcriptional networks,' Genome Medicine, 2018, 10:14 (10 pages).

Tosto, G. et al., 'Genome-wide Association Studies in Alzheimer's Disease: A Review,' Curr Neurol Neurosci Rep. 2013, 13:381 (7 pages).

Wang, J. et al., 'A systemic view of Alzheimer disease—insights from amyloid-β metabolism beyond the brain,' www. nature.com, vol. 13, Oct. 2017, 612-623 (12 pages).

Wu, Y. et al., 'Dementia in western Europe: epidemiological evidence and implications for policy making,' www.thelancet.com/neurology, vol. 15, Jan. 2016, 116-124 (9 pages).

Yan, S. D. et al., 'RAGE and amyloid-P peptide neurotoxicity in Alzheimer's disease,' Nature: vol. 382, Aug. 22, 1996, 685-691 (7 pages).

Zhao, Y. et al., 'TREM2 is a receptor for β-amyloid which mediates microglial function,' Neuron., Mar. 7, 2018, 97(5): 1023-1031.e7. (30 pages).

Phitonex NovaFluor(TM) Conjugation Kit Protocol (2020) (2 pages).

Zhang, V.J., "Blood Biomarkers for Alzheimer's Disease and Multiple Sclerosis," Honours Thesis, Univ. Melbourne (Australia) (Oct. 3, 2017) (74 pages).

Li, Y., "Search for Leukocyte-Based Biomarkers for the Early Diagnosis of Alzheimer's Disease," Honour Thesis, Univ. Melbourne (Australia) (Oct. 8, 2019) (98 pages).

BD Biosciences, Alexa Fluor® 647 Mouse Anti-Human CD163 (2 pages). Accessed on Aug. 11, 2025, Available at https://www. bdbiosciences.com/content/dam/bdb/product_assets/product_pdf/ singcolorpureantibody/alexa_fluor%E2%84%A2_647/pdf_1/568202. pdf.

BD Biosciences, FITC Mouse Anti-Human CD91 (2 pages). Accessed on Aug. 11, 2025, Available at https://www.bdbiosciences.com/ content/dam/bdb/product_assets/product_pdf/singcolorpureantibody/ fitc/pdf_0/550496.pdf.

BD Biosciences, PE Mouse Anti-Human CD59 (2 pages). Accessed on Aug. 11, 2025, Available at https://www.bdbiosciences.com/ content/dam/bdb/product_assets/product_pdf/singcolorpureantibody/ pe/pdf_1/555764.pdf.

Goetzl, Edward J. et al., High Complement Levels in Astrocyte-Derived Exosomes of Alzheim er Disease, Feb. 6, 2018 Annals of Neurology, vol. 83, No. 3, pp. 544-552 (17 pages).

* cited by examiner

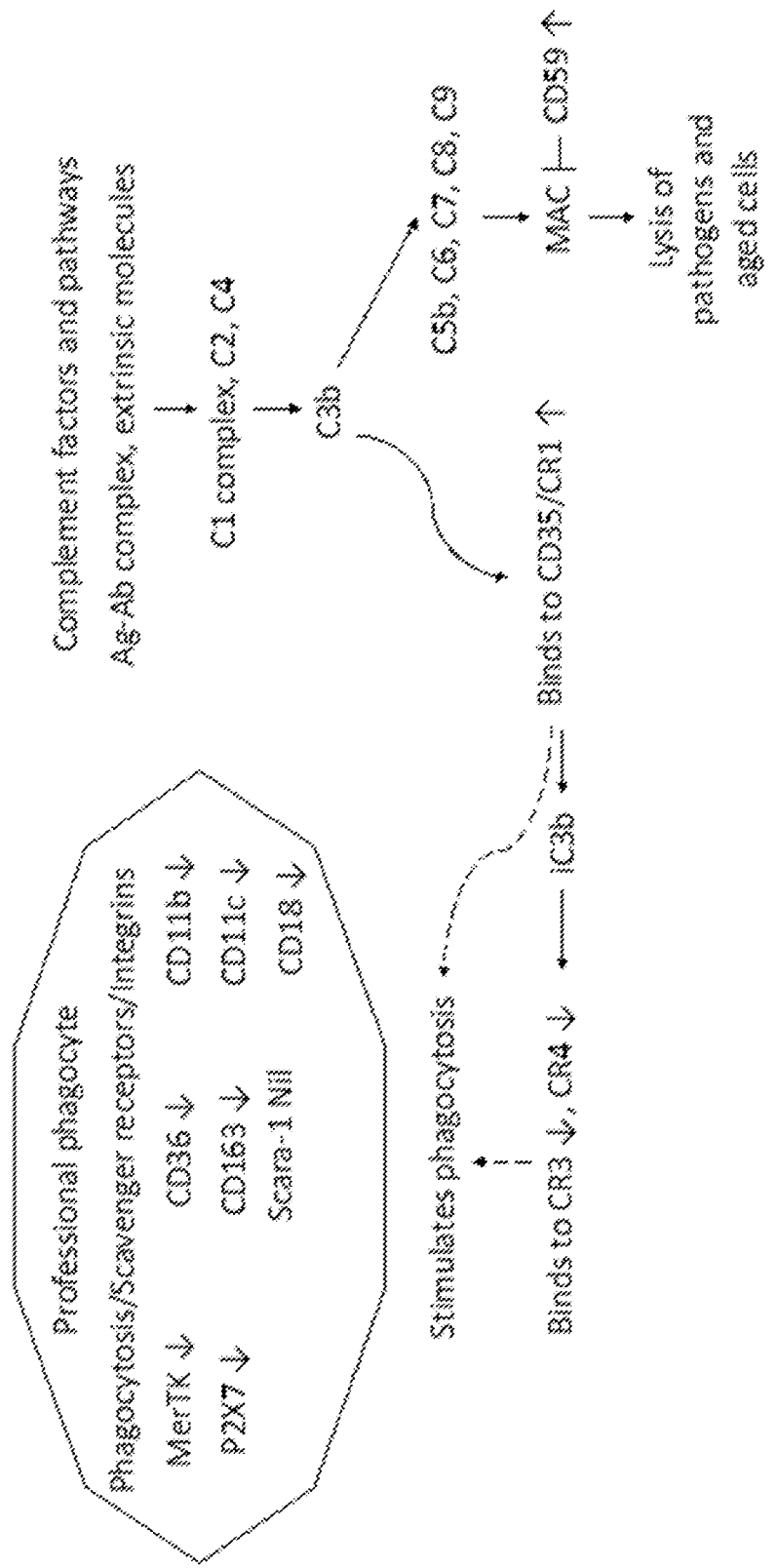

COMPOSITIONS, KITS, AND METHODS FOR DETECTING PRECLINICAL ALZHEIMER'S DISEASE

CROSS-REFERENCE TO RELATED APPLICATIONS

This application claims benefit of priority under 35 U.S.C. § 119(e) of U.S. Provisional Patent Application No. 63/231, 034 entitled, "COMPOSITIONS, KITS, AND METHODS FOR DETECTING PRECLINICAL ALZHEIMER'S DISEASE," filed on Aug. 9, 2021, which is incorporated herein by reference in its entirety.

STATEMENT REGARDING FEDERALLY SPONSORED RESEARCH OR DEVELOPMENT

This invention was made with government support under APP1048082 (2013-2015), APP1061419 (2014-2016), APP1120095 (2017-2019) awarded by the National Health and Medical Research Council (Australia). The Australian government may have certain rights in the invention. Further support was provided by the Bethlehem Griffiths Research Foundation.

FIELD OF INVENTION

This invention relates to the detection and prognosis of Alzheimer's Disease, in some instances before clinically-significant symptoms emerge.

BACKGROUND OF THE INVENTION

The causes of Alzheimer's Disease (AD) are poorly understood, yet the disease correlates with a dramatic decrease in quality of life and high costs of care for patients suffering from its most advance stage. AD typically develops over years. Progressing from cognitively normal (CN), through mild cognitive impairment (MCI), to clinical AD dementia, a patient experiences diminishing short-term memory, attentiveness, and abstract thinking along with increasing apathy, social withdrawal, and isolation. Accumulation of amyloid beta (Aβ) protein in the form of oligomers and plaques has been detected in both familial and sporadic instances of AD.

Employing a novel hypothesis, Applicants have examined a suite of cell-surface leukocyte biomarkers using flow-cytometric techniques for their association with cerebral Aβ accumulation as potential biomarkers for AD. That study, on CN, MCI, and AD patient groups, have yielded surprising correlations allowing for the diagnosis and prognosis of AD. Applicants' discoveries have yielded inventive compositions and methods disclosed herein.

SUMMARY OF THE INVENTION

Certain embodiments of the present invention allow for the use of individual biomarkers not associated with AD before. Applicants have unexpectedly identified several biomarkers suitable for the methods, compositions, and kits of the present invention such as, for example, CD163, CD91, and MerTK. Those biomarkers have been found to be diminished or increased (down-regulated or up-regulated) in AD patients and MCI patients, relative to CN patients, showing their usefulness in diagnosing and prognosing AD, alone or in combination with one or more other biomarkers. Specifically, CD163 and MerTK are down-regulated in AD, while CD91 is up-regulated. See Table 1. Accordingly, some compositions of the present invention include a binding agent such as an antibody for a biomarker such as CD163, CD91, and MerTK, and the antibody is coupled to a detectable moiety such as a fluorophore. In addition, such compositions may include the use of particular binding agents, such as, for example, mouse anti-human IgG monoclonal antibodies for those and other biomarkers. Compositions optionally include an anticoagulant and possibly whole human blood. Kits, such as comprising an antibody-fluorophore conjugate for a biomarker, also appear in embodiments of the present invention.

Further embodiments employ those antibody-fluorophore conjugates in useful methods. Thus, Applicants have invented the use of binding agents for certain biomarkers in methods for the diagnosis of AD in a human patient, for example. Certain embodiments relate to methods for diagnosing AD in a human patient, one such method comprising:

obtaining a blood sample from the human patient;

optionally storing the blood sample in ice;

optionally testing the blood sample within three hours of obtaining the blood sample;

reacting the blood sample with an antibody for a biomarker conjugated with a fluorophore to obtain bound biomarker;

measuring the concentration of bound biomarker in the blood sample by fluorescence of the fluorophore;

comparing the concentration with a concentration range of biomarker in healthy humans;

observing a change in concentration of biomarker in the blood sample;

thereby diagnosing AD in the human patient.

Other aspects relate to methods for determining the efficacy of an AD therapeutic candidate in a human patient, one such method comprising:

(A) obtaining a first blood sample from the human patient;

optionally storing the first blood sample in ice;

optionally testing the first blood sample within three hours of obtaining the first blood sample;

reacting the first blood sample with an antibody for a biomarker conjugated with a fluorophore to obtain first bound biomarker;

measuring a first concentration of first bound biomarker in the first blood sample by fluorescence of the fluorophore;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with the antibody for the biomarker conjugated with the fluorophore to obtain second bound biomarker;

measuring a second concentration of second bound biomarker in the second blood sample by fluorescence of the fluorophore;

(D) observing a change from the first concentration of first bound biomarker to the second concentration of second bound biomarker;

(E) thereby determining the efficacy of the AD therapeutic candidate in the human patient.

Further embodiments relate to panels of biomarkers for diagnosis of AD and evaluation of AD drug efficacy. Accordingly, some additional embodiments include compositions and kits, such as, for example, a composition or kit comprising a first binding agent for a first biomarker conjugated with a first detectable moiety, and a second binding agent for a second biomarker conjugated with a second detectable moiety. Other embodiments include a third binding agent for a third biomarker conjugated with a third detectable moiety. Still other embodiments contain more binding agents each conjugated with a detectable moiety. Ideally, the emission spectra of the several fluorophores do not significantly overlap, or otherwise can be distinguished for quantitative assessment of the presence of the several biomarkers. Panels of antibody-fluorophore conjugates can appear in compositions or kits. A composition indicates one or more ingredients in a single mixture, while a kit includes one or more compositions.

Suitable biomarkers for diagnosis of AD and evaluation of AD drug efficacy include CD11c, CD59, and CD163, in one panel, for example. Another example includes antibody-fluorophore conjugates for CD11b, CD11c, and CD18. An additional panel includes antibody-fluorophore conjugates for CD91, CD59, and CD163, for example. A further panel comprises antibody-fluorophore conjugates for one or more scavenger receptors and their regulators. Another panel comprises antibody-fluorophore conjugates for one or more scavenger receptors and their regulators, and one or more antibody-fluorophore conjugates for one or more leukocyte CD markers. Scavenger receptors and their regulators include, but are not limited to, CD163, CD91, P2X7, MerTK, CD59, CD11c, CD11 b, and CD18. Further scavenger receptors have been identified in the literature, for example, in M. PrabhuDas et al., "Standardizing Scavenger Receptor Nomenclature," J. Immunol., 192(5), (2014) 1997-2006. Leukocyte CD markers include, but are not limited to, CD14, CD15, CD16, CD19, and CD3. Other panels include antibody-fluorophore conjugates for one or more of CD33, CD35, CD36, CD59, CD91, P2X7, and RAGE, and one or more of CD11b, CD11c, CD18, CD163, and MerTK. Yet another panel includes antibody-fluorophore conjugates for one or more of CD11c, CD11b, CD18, CD59, and one or more of CD14, CD15, CD16, CD19, and CD3. Further panels include antibody-fluorophore conjugates for one or more of CD91, CD163, P2X7, and MerTK, and one or more of CD14, CD15, CD16, CD19, and CD3. Still other panels include three groups, such as antibody-fluorophore conjugates for one or more of CD91, CD163, P2X7, and MerTK; one or more of CD11c, CD11 b, CD18, CD59; and one or more of CD14, CD15, CD16, CD19, and CD3.

Still other instances of the present invention relate to methods of measuring relative expression of biomarkers in a human patient, one such method comprising:

obtaining a sample of whole blood from the human patient;

contacting the sample with monoclonal antibodies for the biomarkers conjugated with fluorophores to form bound biomarkers;

measuring fluorescence of the fluorophores, thereby determining the relative expression of the biomarkers.

Yet additional embodiments relate to methods for diagnosing AD in a human patient, one such method comprising:

obtaining a blood sample from the human patient;

optionally storing the blood sample in ice;

optionally testing the blood sample within three hours of obtaining the blood sample;

reacting the blood sample with monoclonal antibodies for the biomarkers conjugated with fluorophores to form bound biomarkers;

measuring a concentration of bound biomarkers in the blood sample by fluorescence of the fluorophores;

observing changes in the concentration of each of the bound biomarkers relative to concentration ranges of biomarkers in healthy humans;

thereby diagnosing AD in the human patient.

Still other aspects relate to methods for determining the efficacy of an AD therapeutic candidate in a human patient, one such method comprising:

(A) obtaining a first blood sample from the human patient;

optionally storing the first blood sample in ice;

optionally testing the first blood sample within three hours of obtaining the first blood sample;

reacting the first blood sample with a first aliquot of monoclonal antibodies for biomarkers conjugated with fluorophores to obtain first bound biomarkers;

measuring a first concentration of first bound biomarkers;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with a second aliquot of the monoclonal antibodies for biomarkers conjugated with fluorophores to obtain second bound biomarkers;

measuring a second concentration of second bound biomarkers by fluorescence of the fluorophores;

(D) observing changes from the first concentration of first bound biomarkers to the second concentration of second bound biomarkers in the human patient;

(E) thereby determining the efficacy of the AD therapeutic candidate in the human patient.

Other examples of the present invention relate to methods for diagnosing AD in a human patient, another such method comprising:

obtaining a blood sample from the human patient;

optionally storing the blood sample in ice;

optionally testing the blood sample within three hours of obtaining the blood sample;

reacting the blood sample with a monoclonal antibody for a scavenger receptor conjugated with a fluorophore to obtain bound scavenger receptor;

measuring a concentration of bound scavenger receptor in the blood sample by fluorescence of the fluorophore;

observing a decrease in the concentration of bound scavenger receptor relative to a concentration range of scavenger receptor in healthy humans;

thereby diagnosing AD in the human patient.

Still further embodiments relate to methods for determining the efficacy of an AD therapeutic candidate in a human patient, one such method comprising:

(A) obtaining a first blood sample from the human patient;

optionally storing the first blood sample in ice;

optionally testing the first blood sample within three hours of obtaining the first blood sample;

reacting the first blood sample with a first aliquot of a plurality of antibody-fluorophore conjugates, each antibody-fluorophore conjugate in the plurality comprising a monoclonal antibody for a scavenger receptor conjugated with a fluorophore;

thereby forming first bound scavenger receptors;

measuring first concentrations of the first bound scavenger receptors in the first blood sample by fluorescence of the fluorophores;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with a second aliquot of the plurality of antibody-fluorophore conjugates;

thereby forming second bound scavenger receptors;

measuring second concentrations of the second bound scavenger receptors in the second blood sample by fluorescence of the fluorophores;

(D) observing an increase from the first concentration of first bound scavenger receptors to the second concentration of second bound scavenger receptors in the human patient;

(E) thereby determining the efficacy of the AD therapeutic candidate in the human patient.

Still further embodiments of the present invention relate to compositions, kits, and methods optimized for assessing AD risks in patients, efficacy of AD medicines, and other uses. In some cases, those embodiments include binding agents for certain biomarkers conjugated with detectable moieties. For example, certain of those embodiments relate to a composition comprising:

a monoclonal antibody for CD11c conjugated with a first fluorophore;

a monoclonal antibody for CD14 conjugated with a second fluorophore;

a monoclonal antibody for CD59 conjugated with a third fluorophore; and a monoclonal antibody for CD163 conjugated with a fourth fluorophore.

For another example, others of those embodiments relate to a composition comprising:

a monoclonal antibody for CD91 conjugated with a first fluorophore;

a monoclonal antibody for CD59 conjugated with a second fluorophore; and a monoclonal antibody for CD163 conjugated with a third fluorophore.

Further instances of the present invention relate to a kit comprising:

a monoclonal antibody for CD11c conjugated with a first fluorophore;

a monoclonal antibody for CD14 conjugated with a second fluorophore;

a monoclonal antibody for CD59 conjugated with a third fluorophore; and a monoclonal antibody for CD163 conjugated with a fourth fluorophore.

Other instances relate to a kit comprising:

a first binding agent for CD91 conjugated with a first detectable moiety;

a second binding agent for CD59 conjugated with a second detectable moiety; and a third binding agent for CD163 conjugated with a third detectable moiety.

Any suitable antibodies can be used in the various embodiments of the present invention, such as, for example, mouse anti-human IgG monoclonal antibodies.

Another aspect relates to a composition comprising:

a monoclonal antibody for CD91 conjugated with a first fluorophore;

a monoclonal antibody for CD14 conjugated with a second fluorophore;

a monoclonal antibody for CD59 conjugated with a third fluorophore; and a monoclonal antibody for CD163 conjugated with a fourth fluorophore.

An additional aspect relates to a composition comprising:

a monoclonal antibody for CD91 conjugated with a first fluorophore;

a monoclonal antibody for CD59 conjugated with a second fluorophore; and a monoclonal antibody for CD163 conjugated with a third fluorophore.

Further aspects relate to a kit comprising:

a monoclonal antibody for CD91 conjugated with a first fluorophore;

a monoclonal antibody for CD14 conjugated with a second fluorophore;

a monoclonal antibody for CD59 conjugated with a third fluorophore; and a monoclonal antibody for CD163 conjugated with a fourth fluorophore.

In certain additional aspects, a kit may comprise:

a monoclonal antibody for CD91 conjugated with a first fluorophore;

a monoclonal antibody for CD59 conjugated with a second fluorophore; and a monoclonal antibody for CD163 conjugated with a third fluorophore.

Still further aspects relate to using compositions and kits comprising binding agent-detectable moiety conjugates such as antibody-fluorophore conjugates for CD11c, CD14, CD59, and CD163 for (1) determining the relative expression of those biomarkers in a human patient; (2) diagnosing AD in a human patient; and (3) determining the efficacy of an AD therapeutic candidate in a human patient, as those methods are described herein.

While the disclosure provides certain specific embodiments, the invention is not limited to those embodiments. A person of ordinary skill will appreciate from the description herein that modifications can be made to the described embodiments and therefore that the specification is broader in scope than the described embodiments. All examples are therefore non-limiting.

BRIEF DESCRIPTION OF THE DRAWINGS

FIG. 1 depicts a mechanism that may explain the usefulness of some embodiments of the present invention, without binding that invention to theory.

DETAILED DESCRIPTION

As required, detailed embodiments of the present invention are disclosed herein; however, it is to be understood that the disclosed embodiments are merely exemplary of the invention that may be embodied in various forms. The figures are not necessarily to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Unless defined otherwise, all technical and scientific terms used herein have the same meaning as is commonly understood by one of ordinary skill in the art to which this disclosure belongs. In the event that there is a plurality of definitions for a term herein, those in this disclosure prevail unless stated otherwise.

Wherever the phrase "for example," "such as," "including" and the like are used herein, the phrase "and without limitation" is understood to follow unless explicitly stated otherwise. Similarly "an example," "exemplary" and the like are understood to be non-limiting.

The term "substantially" allows for deviations from the descriptor that don't negatively impact the intended purpose. Descriptive terms are understood to be modified by the term "substantially" even if the word "substantially" is not explicitly recited.

The term "about" when used in connection with a numerical value refers to the actual given value, and to the approximation to such given value that would reasonably be inferred by one of ordinary skill in the art, including approximations due to the experimental and or measurement conditions for such given value.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

A biomarker is a specific chemical moiety expressed in the human body. An antibody is an immunologic protein adapted to bind to a specific biomarker. Antibodies can be present in monomeric or polymeric forms. "Fluorophore" indicates a chemical species that absorbs light at an excitation wavelength and emits fluorescence at an emission wavelength for the purposes of detection and quantification. As known in the art, a fluorophore will exhibit a characteristic absorption spectrum and an emission spectrum. Antibody-fluorophore conjugates include an antibody and at least one fluorophore chemically connected together so that the antibody can bind to a biomarker and be detected or even quantified by the fluorescence intensity of the connected fluorophore(s).

A kit includes two or more compositions such as those described herein. Optionally, a kit includes other useful items such as sample preparation reagents, collection tubes, control samples, instructions for use, or a combination of such items.

Certain abbreviations used herein and their definitions include

Aβ Amyloid β peptide
AD Alzheimer's Disease
AIBL Australian Imaging, Biomarkers and Lifestyle study
APC Allophycocyanin
APOE Human apolipoprotein E (symbol for gene is italicized; for protein is not).
APP Amyloid precursor protein
ATN Amyloid, tau, neurodegeneration
AUC Area under curve
CDR Clinical dementia rating
CN Cognitively normal
CSF Cerebrospinal fluid
FACS Fluorescence-activated cell sorting
FCIP Flow cytometry immunophenotyping
FITC Fluorescein isothiocyanate
GWAS Genome-wide association study
IDI Integrated discrimination improvement
mAb monoclonal antibodies
MAC Membrane attack complex
MCI Mild cognitive impairment
MFI Mean fluorescent intensity
MRI Magnetic resonance imaging
MMSE Mini Mental State Examination
PACC Preclinical Alzheimer's Cognitive Composite
PE R-phycoerythrin
PerCP peridinin-chlorophyll-protein complex
PET Positron emission tomography
RAGE Receptor for advanced glycation end products
ROC Receiver operating characteristic Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

I. Individual Biomarkers

As stated above, Applicants have unexpectedly identified several biomarkers suitable in such methods and compositions, such as, for example, CD163, CD91, and MerTK. Those biomarkers have been found to be changed in AD patients and MCI patients, relative to CN patients. Specifically, CD163 and MerTK are down-regulated in AD, while CD91 is up-regulated, with strong correlation with AD. See Table 1 below. They can be used individually or in combination with each other and/or other biomarkers for diagnosing AD and other uses. Table 1 includes results obtained in accordance with the protocols set forth in the Examples.

TABLE 1

Biological relevance and changes of potential biomarkers in AD.

| GO class (direct) | Potential biomarkers | Biological relevance to AD | Changes in AD |
|---|---|---|---|
| Amyloid-beta binding & microglial cell activation | CD11b | Integrin subunit alpha M; Complement component receptor 3 alpha; Phagocytosis; Integrins; C3b binding. | Phase I, III Nil; Phase II ↓ |

TABLE 1-continued

Biological relevance and changes of potential biomarkers in AD.

| GO class (direct) | Potential biomarkers | Biological relevance to AD | Changes in AD |
|---|---|---|---|
| Integrin binding | CD11c | Integrin subunit alpha X; Complement component receptor 4 alpha; Regulation of actin cytoskeleton. | Phase I, II, III ↓ |
| Amyloid-beta binding & microglial cell activation | CD18/ITGB2 | Integrin subunit beta 2; Combines with different alpha chains, e.g. CD11b and CD11c, to form different integrin heterodimers also referred to as CR3 and CR4. | Phase III ↓ |
| Protein binding | CD33 | GWAS associated gene for AD [21]; Myeloid cell surface antigen; Immunoglobulin superfamily cell adhesion molecule. | Phase II ↓ |
| Complement component C3b/4b binding | CD35/CR1 | GWAS associated gene for AD [22]; Phagocytosis; Integrins; Complement receptor 1. | Phase III ↑ |
| Amyloid-beta binding & antigen processing and presentation | CD36 | Scavenger receptor class B member 1; Phagocytosis; Receptor for oxidized low-density lipoprotein (LDL) [32]; Receptor for Aβ [33]. | Phase III ↓ |
| Protein binding | CD59 | Complement inhibitory protein; Prevent formation of the complement membrane attack complex (MAC) [20]. | Phase III ↑ |
| Amyloid-beta binding & scavenger receptor activity | CD91 | Low-density lipoprotein receptor-related protein 1 (LRP1); | Phase III ↑ |
| Scavenger receptor activity | CD163 | Scavenger receptor. | Phase III ↓ |
| Protein binding & protein phosphorylation | MerTK | Receptor protein-tyrosine kinase; Mediates phagocytosis in microglial cells [44] and retinal pigment epithelium [45]. | Phase III ↓ |
| Extracellularly ATP-gated cation channel activity | P2X7/P2RX7 | Innate phagocytosis [7]. | Phase I, III ↓; Phase II Nil |
| Amyloid-beta binding & microglial cell activation | RAGE/AGER | Mediates Aβ transport across the blood-brain barrier and accumulation in brain [30-31]. | Phase III ↑ |
| Amyloid-beta binding & scavenger receptor activity | SCARA-1/ MSR1 | Macrophage scavenger receptor 1; Phagocytosis; Mediates uptake of fibrillar amyloid [5]. | Phase III ↑ |

GO: Gene ontology.
↑: up-regulation.
↓: down-regulation.
Nil: No change.

Embodiments of the present invention employ binding agents for biomarkers, such as, for example, from single chain variable fragments, antibody mimetics, antibody fragments, antibodies, monoclonal antibodies, and combinations thereof. The binding agents should exhibit adequate selectivity and affinity for the desired biomarkers. Any suitable antibodies can be used in the embodiments of the present invention. For example, antibodies can be monoclonal, and be derived from mice, horses, rabbits, or pigs, for example via hybridomas. In some cases, the antibody is a mouse anti-human IgG monoclonal antibody for the biomarker. Care should be taken to avoid the presence of antibody inhibitors, such as, for example, heparin.

Further embodiments employ detectable moieties, such as, for example, radioisotopes, stable isotopes, fluorophores, and combinations thereof. The detectable moieties should be selected to avoid an overlap in their signaling that would confuse the detecting technology. For example, the same radioisotope should not be conjugated to different binding agents in the same kit. Similarly, fluorophores should be selected to avoid overlapping emission spectra. Any suitable fluorophores can be used in the embodiments of the present invention. Suitable fluorophores include, but are not limited to, those sold under the Alexa Fluor® trademark, such as Alexa Fluor® 488, Alexa Fluor® 647; allophycocyanin; fluorescein compounds such as fluorescein isothiocyanate, fluorescein amidite, and 6-carboxyfluorescein; R-phycoerythrin; erythrosine; a peridinin-chlorophyll-protein complex such as that known as PerCP; rhodamine dyes such as carboxytetramethylrhodamine, tetramethylrhodamine, and sulforhodamine; coumarin; lanthanide phosphors; quantum dots; and other fluorophores known in the art. Care should be taken to avoid using two fluorophores with closely-overlapping emission spectra. For example, Alexa Fluor® 647 should not be used with allophycocyanin. Alexa Fluor® 488 should not be used with fluorescein isothiocyanate. Also, in some cases, to eliminate non-specific binding, a blocking/bleaching reagent may be employed, such as is known in the art.

Further examples of fluorophores include, but are not limited to, BD Horizon™ and BD Horizon Brilliant™ Ultraviolet family of dyes sold by Becton, Dickinson and Company (Franklin Lakes, NJ), such as, for example, those fluorophores known as BUV395; BUV563; BUV615, BUV661; BUV737; BUV805, BV421; BV480; BV510, BV605; BV650; BV711; BV750; and BV786. Further fluorophores include BF Horizon™ tandem conjugate PE-CF594, tandem conjugate PerCP with a cyanine dye known as PerCP-Cy™ 5.5 offered by Becton, Dickinson and Company (Franklin Lakes, NJ); R-phycoerythrin (PE); and BD Horizon™ Red 718; or a combination of two or more thereof. Additional examples include NovaFluor™ brand fluorescent labels offered by Phitonex, Inc. now part of Thermo Fisher Scientific Inc. (Waltham, MA), such as, for example, those fluorophores known as NovaFluor™ Blue 510, NovaFluor™ Blue 530, NovaFluor™ Blue 555, NovaFluor™ Blue 610-30S, NovaFluor™ Blue 610-70S, NovaFluor™ Blue 660-120S, NovaFluor™ Blue 660-40S, NovaFluor™ Yellow 570, NovaFluor™ Yellow 610, NovaFluor™ Yellow 660, NovaFluor™ Yellow 690, NovaFluor™ Yellow 700, NovaFluor™ Yellow 720, NovaFluor™ Red 660, NovaFluor™ Red 685, NovaFluor™ Red 700, or a combination thereof.

Still other fluorophores may be chosen from fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, and combinations thereof.

Specific examples of antibody-fluorophore conjugates include mouse anti-human CD163 antigen conjugated with fluorescent dye sold under the trademark Alexa Fluor® 647 (Molecular Probes, Inc., Eugene OR); mouse anti-human CD91 antigen conjugated with fluorescein isothiocyanate; and mouse anti-human MerTK antigen conjugated with fluorescent dye sold under the trademark BD Horizon Brilliant™ Blue 700 (Beckton, Dickinson and Company, Franklin Lakes, NJ).

Conjugating a binding agent to a detectable moiety, such as an antibody to a fluorophore, can be accomplished by any suitable method. For example, known chemistries are well-developed and commercially available. Fluorophore-conjugated antibodies are available, such as, for example, from Becton, Dickinson and Company. Radioisotopes such as $^{18}F$ and stable isotopes such as $^2H$ can be incorporated into the binding agent, or into a molecule that stably attaches to the binding agent. Fluorodeoxyglucose containing $^{18}F$, or a deuterated molecule can be used, for example. Quantum dots conjugated to a binding agent such as an antibody also may be mentioned.

Compositions useful in the present invention are not limited. Certain instances provide a composition comprising a mouse anti-human IgG monoclonal antibody for CD163 conjugated with a fluorophore; and at least one anti-coagulant. Any suitable anti-coagulant can be used in the various embodiments of the present invention, such as, for example, ethylene diamine tetraacetic acid, at least one salt thereof, citric acid, at least one salt thereof, or a combination of any of the foregoing. Any suitable salt may be used, such as, for example, alkali metal salts such as monosodium, disodium, trisodium, or tetrasodium salts may be mention. Other instances relate to a composition comprising a mouse anti-human IgG monoclonal antibody for CD163 conjugated with a fluorophore; ethylene diamine tetraacetic acid, at least one salt thereof, citric acid, at least one salt thereof, or a combination of any of the foregoing; and whole blood of a human patient. Any of those compositions can include additional useful ingredients, such as, for example, bovine serum albumin and sodium azide.

Various methods appear in embodiments of the present invention. Some methods relate to diagnosing AD in a human patient. Certain of those methods include obtaining a blood sample from the human patient;

optionally storing the blood sample in ice, which can include refrigeration;

optionally testing the blood sample within three hours of obtaining the blood sample;

reacting the blood sample with a monoclonal antibody for a biomarker such as CD163, CD91, or MerTK conjugated with a fluorophore to obtain bound biomarker;

measuring the concentration of bound biomarker in the blood sample by fluorescence of the fluorophore;

comparing the concentration with a concentration range of the biomarker in healthy humans;

observing a changed concentration of the biomarker in the blood sample; thereby diagnosing AD in the human patient.

In some cases, a blood sample is obtained from a human patient, and optionally stored on ice or in refrigeration. As used herein, "storing on ice" includes any sort of refrigeration, to include anything from a food-free refrigerator to an ice bath to dry ice, so long as the storage method does not harm the sample. The sample can be tested within any suitable time, such as within three hours of being withdrawn. The sample is tested by reacting the blood sample with an antibody for a biomarker conjugated with a fluorophore to obtain bound biomarker, and measuring the concentration of bound biomarker in the blood sample by fluorescence of the fluorophore. Fluorescence can be measured by any suitable technique, such as flow cytometry analysis.

Certain instances allow for the comparison of a concentration of the biomarker in the patient in question with a concentration range of the biomarker in healthy humans. This comparison can be achieved in any suitable manner. Data for healthy humans can be found in the literature, or can be developed by testing a number of healthy persons otherwise determined to be free of AD or MCI. Those healthy persons, for example, can exhibit any suitable indication of health, such as, for example, having <25CL as measured by amyloid PET imaging. The concentration can be compared at any suitable level. In some cases, the concentration is compared in whole blood. In other cases, the concentration is compared on leukocytes. In still other cases, the concentration is compared on subsets of leukocytes, such as, for example, wherein the leukocytes are chosen from monocytes, C14+ monocytes, CD14+CD16− monocytes, neutrophils, CD14− neutrophils, CD14−CD16+ neutrophils, lymphocytes, B lymphocytes, T lymphocytes, natural killer cells, and combinations thereof. The subsets of leukocytes can be identified according to any suitable method. Cell sorting can be performed, or the cells can be gated according to methods known in flow cytometry, for example.

The concentration of detectable moiety can be measured by any suitable method. Scintillation counting, mass spectroscopy, and fluorescence may be mentioned. Measuring the concentration of bound biomarker comprises measuring the mean fluorescence intensity of bound biomarker conjugated to a fluorophore, for example. In the case of CD 163, observing a decreased concentration of CD163 in a blood sample can mean measuring a decrease in mean fluorescence intensity of at least about 11%, at least about 12%, at least about 13%, at least about 14%, at least about 15%, at least about 16%, at least about 17%, at least about 18%, or at least about 19% compared to a mean fluorescence intensity of bound CD163 for a pool of human participants who have <25CL as measured by amyloid PET imaging.

Observing an increased concentration of CD91 in a blood sample can mean measuring an increase in mean fluorescence intensity of at least about 44%, at least about 50%, at least about 55%, or at least about 59% compared to a mean fluorescence intensity of bound CD91 for a pool of human patients who have <25CL as measured by amyloid PET imaging.

Observing a decreased concentration of MerTK in the blood sample comprises measuring a decrease in mean fluorescence intensity of at least about 12% compared to a mean fluorescence intensity of bound MerTK for a pool of human patients who have <25CL as measured by amyloid PET imaging.

Other methods relate to the testing of AD therapeutic candidates to see if they would be efficacious as drugs to treat, prevent, or delay the onset of AD. Certain of those methods include (A) obtaining a first blood sample from the human patient;

optionally storing the first blood sample in ice;

optionally testing the first blood sample within three hours of obtaining the first blood sample;

wherein the testing is performed by reacting the first blood sample with a first aliquot of a monoclonal antibody for a biomarker such as CD163, CD91, or MerTK conjugated with a fluorophore to obtain first bound biomarker;

measuring a first concentration of first bound biomarker in the first blood sample by fluorescence of the fluorophore;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with a second aliquot of the monoclonal antibody for the biomarker conjugated with the fluorophore to obtain second bound biomarker;

measuring a second concentration of second bound biomarker in the second blood sample by fluorescence of the fluorophore;

(D) observing a change from the first concentration of first bound biomarker to the second concentration of second bound biomarker;

(E) thereby determining the efficacy of the AD therapeutic candidate in the human patient. In the cases of CD163 and MerTK, those biomarkers are down-regulated in AD, so an efficacious AD therapeutic candidate would up-regulate or increase the concentration of those biomarkers in a human patient. For CD91, this biomarker is up-regulated in AD, so an efficacious AD therapeutic candidate would down-regulate or decrease the concentration of that biomarker in a human patient.

Any suitable AD therapeutic candidate can be used. In some cases, the AD therapeutic candidate is a phagocytosis-promoting agent, a scavenger receptor agonist, or both. Thus, a candidate drug can act to promote phagocytosis; it can act as an agonist on a scavenger receptor; or both activities can appear. Of course, other mechanisms of action can be tested by this protocol as well. A suitable AD therapeutic candidate can have any regulatory approval status, from investigational new drugs to those approved therapeutics requiring post-market surveillance, for example, as the method is probing the candidate's efficacy on the particular patient. The AD therapeutic candidate can be administered in any suitable amount, by any suitable route. In some cases, the amount is a therapeutically effective amount, or a suspected therapeutically effective amount. For example, an AD therapeutic candidate can be administered to the patient in an amount of less than 1 g/kg body weight of the patient, per day. For another example, an AD therapeutic candidate can be administered to the patient in an amount greater than about 1 ng/kg body weight of the patient, per day. In other cases, an AD therapeutic candidate can be administered to the patient in an amount of not more than about 0.1 µg/kg, not more than about 1 µg/kg, not more than about 10 µg/kg, or not more than about 100 µg/kg per day. Any suitable time period can be employed, such as, for example, 1 day, 5 days, 10 days, 30 days, 60 days, 90 days, 180 days, 365 days. or more than 365 days. Oral administration, injections via intravenous or intramuscular routes, transdermal patches, implants, and the like may be employed, for example.

II. Combinations of Biomarkers

Applicants have found that combinations of biomarkers hold predictive value in diagnosing and prognosing AD and drug efficacy evaluation. Those biomarkers can represent indicators of a single mechanism, such as, for example, phagocytosis-modulating molecules. Or those biomarkers can indicate more than one mechanism or aspect of the patient's health, such as, for example, one or more phagocytosis-modulating molecules in combination with one or more leukocyte CD markers including CD14 (monocyte), CD16 (monocyte, NK cells, neutrophils), CD15 (neutrophils), CD19 (B lymphocytes) and CD3 (T lymphocytes).

Some embodiments of the present invention probe the expression of one or more scavenger receptors for diagnosing or prognosing AD. Table 1, set forth above, describes the expected activities of certain biomarkers including scavenger receptors. Particular panels, of scavenger receptors and other biomarkers include, for example, CD11c, CD59, and CD163, CD11 b, CD11c, and CD18, CD91, CD59, and CD163, one or more of CD33, CD35, CD36, CD59, CD91, P2X7, and RAGE, with one or more of CD11 b, CD11c, CD18, CD163, and MerTK;

one or more of CD163, CD91, P2X7, MerTK CD59, CD11c, CD11 b, and CD18, with one or more of CD14, CD15, CD16, CD19, and CD3, one or more of CD11c, CD11 b, CD18, and CD59, with one or more of CD14, CD15, CD16, CD19, and CD3, one or more of CD11c, CD11 b, CD18, and CD59, with one or more of CD14, CD15, CD16, CD19, and CD3, one or more of CD91, CD163, P2X7, and MerTK, with one or more of one or more of CD14, CD15, CD16, CD19, and CD3, one or more of CD91, CD163, P2X7, and MerTK, with one or more of CD11c, CD11b, CD18, and CD59, and with one or more of CD14, CD15, CD16, CD19, and CD3.

Those panels would be represented by the presence of a binding agent such as a monoclonal antibody for the particular biomarker conjugated with a suitable detectable moiety such as a fluorophore. In any combination of antibody-fluorophore conjugates, it can be appreciated, the fluorophores should be selected so that there is not significant or unresolvable overlap in their emission spectra, or one could not readily determine the relative intensities of the overlapping spectra. In some cases, care should be taken on the excitation parameters as well, so that qualitative information can be obtained. All fluorophores should be adequately illuminated under the intensities of excitation used, so that quantitative data emerges. Some embodiments of the present invention depend on the relative concentrations of biomarkers, or on the concentration of one or more biomarkers in a patient's sample relative to that of healthy persons.

Certain instances relate to compositions and kits. For example, one instance relates to a composition or a kit comprising a monoclonal antibody for CD11c conjugated with a first fluorophore; a monoclonal antibody for CD59 conjugated with a second fluorophore; and a monoclonal antibody for CD163 conjugated with a third fluorophore. Another instance relates to a composition or a kit comprising a mouse anti-human IgG monoclonal antibody for CD11c conjugated with a first fluorophore; a mouse anti-human IgG monoclonal antibody for CD59 conjugated with a second fluorophore; and a mouse anti-human IgG monoclonal antibody for CD163 conjugated with a third fluorophore. A further instance relates to a composition or a kit comprising a mouse anti-human IgG monoclonal antibody for CD91 conjugated with a first fluorophore; a mouse anti-human IgG monoclonal antibody for CD59 conjugated with a second fluorophore; and a mouse anti-human IgG monoclonal antibody for CD163 conjugated with a third fluorophore. Suitable fluorophores include those described above. In some cases, the first fluorophore is allophycocyanin or fluorescein isothiocyanate; the second fluorophore is R-phycoerythrin; and the third fluorophore is fluorescent dye sold under the trademark Alexa Fluor® 647 (Molecular Probes, Inc., Eugene OR).

Optionally, the composition or kit includes at least one anticoagulant. Any suitable anticoagulant can be used as described above. Any suitable additional ingredients also may appear, such as, for example, bovine serum albumin and sodium azide.

Compositions according to the present invention may include whole blood from a human patient. Such a composition appears when a sample from the patient is being tested according to the present invention.

Various methods appear in several embodiments of the present invention. Some methods relate to measuring the relative expression of certain biomarkers in a patient. It has been found that for MCI and AD patients, certain biomarkers increase while other biomarkers decrease, relative to CN patients. For example, one such method relates to measuring relative expression of CD11c, CD59, and CD163 in a human patient, the method comprising:

obtaining a sample of whole blood from the human patient;

contacting the sample with a monoclonal antibody for CD11c conjugated with a first fluorophore;

a monoclonal antibody for CD59 conjugated with a second fluorophore; and a monoclonal antibody for CD163 conjugated with a third fluorophore, to form bound CD11c, bound CD59, and bound CD163;

measuring fluorescence of the first fluorophore, the second fluorophore, and the third fluorophore, thereby determining the relative expression of CD11c, CD59, and CD163. As explained above, any suitable antibodies and fluorophores can be employed. With reference to Table 1, if CD11c and CD163 appear down-regulated while CD59 appears up-regulated, the patient can be assessed for MCI or AD, and further treatment or prophylaxis measures may be taken.

Another such method relates to measuring relative expression of CD91, CD59, and CD163 in a human patient, the method comprising:

obtaining a sample of whole blood from the human patient;

contacting the sample with a monoclonal antibody for CD91 conjugated with a first fluorophore;

a monoclonal antibody for CD59 conjugated with a second fluorophore; and a monoclonal antibody for CD163 conjugated with a third fluorophore, to form bound CD91, bound CD59, and bound CD163;

measuring fluorescence of the first fluorophore, the second fluorophore, and the third fluorophore, thereby determining the relative expression of CD91, CD59, and CD163. As explained above, any suitable antibodies and fluorophores can be employed. With reference to Table 1, if CD91 and CD59 appear up-regulated while CD163 appears down-regulated, the patient can be assessed for MCI or AD, and further treatment or prophylaxis measures may be taken.

Methods for diagnosing AD in a human patient, which may include assessing whether the patient falls into a CN, MCI, or AD diagnosis, also can employ combinations of biomarkers. One such method includes reacting a blood sample from the patient with a plurality of antibody-fluorophore conjugates, each antibody-fluorophore conjugate in the plurality comprising a mouse anti-human IgG monoclonal antibody for a scavenger receptor conjugated with a fluorophore thereby forming bound scavenger receptors;

measuring concentrations of the bound scavenger receptors in the blood sample by fluorescence of the fluorophores; and observing a decrease in the concentration of at least one bound scavenger receptor relative to a concentration range of a corresponding scavenger receptor in healthy humans; thereby diagnosing AD in the human patient. In some cases, the scavenger receptors are chosen from CD163, MerTK, CD11b, CD11c, CD18, and combinations thereof.

Measuring the concentration of bound biomarkers can proceed in any suitable manner. Whole blood, leukocytes, or subsets of leukocytes can be examined. One biomarker can be examined on one subset of leukocytes, for example, while another biomarker can be examined on a different subset of leukocytes. In some cases, for example, measuring the concentration of bound biomarker comprises measuring the mean fluorescence intensity of bound biomarker. Similarly observing a change (increase or decrease) in the concentration of bound biomarker may involve comparing a mean fluorescence intensity of bound biomarker for the human patient with a mean fluorescence intensity of bound biomarker for a pool of human participants who have <25CL as measured by amyloid PET imaging. For example, observing a decrease in the concentration of bound CD11c may involve measuring a decrease in mean fluorescence intensity of at least about 15%, at least about 19%, at least about 22%, at least about 25%, at least about 28%, at least about 30%, or at least about 34% compared to a mean fluorescence intensity of bound CD11c for the pool of human participants who have <25CL as measured by amyloid PET imaging. In another example, observing an increase in the concentration of bound CD59 comprises measuring an increase in mean fluorescence intensity of at least about 27%, at least about 30%, at least about 35%, at least about 40%, at least about 45%, at least about 50%, at least about 55%, at least about 60%, at least about 65%, at least about 70%, at least about 75%, or at least about 78% compared to a mean fluorescence intensity of bound CD59 for the pool of human participants who have <25CL as measured by amyloid PET imaging.

In certain instances, measuring the concentration of biomarker is correlated with specific cells. For example, the concentration of a biomarker may exhibit a significant difference from healthy people when measured on particular cells. Cell population subsets can be identified in any suitable manner, and correlated with other biomarkers. For example, leukocytes can be isolated from whole blood, and the concentration of CD163 can be measured on leukocytes only. Or the leukocytes or subsets thereof can be gated according to known methods useful in flow cytometry. Natural killer (NK) cells, B lymphocytes, T lymphocytes, classical monocytes, intermediate monocytes, non-classical monocytes and mature neutrophils, for example, can be gated and probed for the expression of one or more biomarkers such as CD163, CD91, and MerTK. Such gating strategy typically involves forward and side scatters of lymphocytes, monocytes and neutrophils, together with their surface expression of cell-specific CD markers, including, for example, monocytes (CD14+), neutrophils (CD15+ or CD16+), B lymphocytes (CD19+), T lymphocytes (CD3+), natural killer cells (CD16+), and combinations thereof. As used herein, classical monocytes can be described as CD14+CD16–, non-classical monocytes are CD14dimCD16+, and intermediate monocytes are CD14+CD16+.

Certain further embodiments relate to determining efficacy of an AD therapeutic candidate in a human patient using a combination of biomarkers. One such method comprises (A) obtaining a first blood sample from the human patient; reacting the first blood sample with a first aliquot of a plurality of antibody-fluorophore conjugates, each antibody-fluorophore conjugate in the plurality comprising a mouse anti-human IgG monoclonal antibody for a scavenger receptor conjugated with a fluorophore, thereby forming first bound scavenger receptors; measuring first concentrations of the first bound scavenger receptors in the first blood sample by fluorescence of the fluorophores;

(B) administering the AD therapeutic candidate to the human patient;

(C) obtaining a second blood sample from the human patient;
reacting the second blood sample with a second aliquot of the plurality of antibody-fluorophore conjugates, thereby forming second bound scavenger receptors; measuring second concentrations of the second bound scavenger receptors in the second blood sample by fluorescence of the fluorophores;

(D) observing an increase from the first concentration of first bound scavenger receptors to the second concentration of second bound scavenger receptors in the human patient;

(E) thereby determining the efficacy of the AD therapeutic candidate in the human patient. Any suitable AD therapeutic candidate can be tested, such as, for example, a phagocytosis-promoting agent, a scavenger receptor agonist, or a candidate that exhibits both mechanisms.

III. Two Panels

Applicants have found two combinations of biomarkers useful in certain of the several compositions, kits, and methods of the present invention. One combination relates to biomarkers CD163, CD59, CD11c, and CD14. The second combination relates to biomarkers CD163, CD59, CD91, and CD14. Those combinations can be represented by binding agents for the biomarkers, such as monoclonal antibodies, conjugated with distinctive detectable moieties, such as fluorophores. Accordingly, one embodiment relates to a composition comprising:

a monoclonal antibody for CD11c conjugated with a first fluorophore;
a monoclonal antibody for CD14 conjugated with a second fluorophore;
a monoclonal antibody for CD59 conjugated with a third fluorophore; and
a monoclonal antibody for CD163 conjugated with a fourth fluorophore. Another embodiment relates to a composition comprising:
a monoclonal antibody for CD91 conjugated with a first fluorophore;
a monoclonal antibody for CD14 conjugated with a second fluorophore;
a monoclonal antibody for CD59 conjugated with a third fluorophore; and
a monoclonal antibody for CD163 conjugated with a fourth fluorophore. Those monoclonal antibodies can include any suitable antibodies, such as, for example, mouse anti-human IgG monoclonal antibodies. As stated above, monoclonal antibodies derived from mice, horses, rabbits, or pigs, for example via hybridomas can be used. At least one anticoagulant also can appear in those compositions, such as, for example, ethylene diamine tetraacetic acid, at least one salt thereof, citric acid, at least one salt thereof, or a combination of any of the foregoing. Suitable additional ingredients can be present, for example, bovine serum albumin and sodium azide, or for another example, phosphate buffered saline, gelatin, and sodium azide.

Detectable moieties include radioisotopes, stable isotopes, fluorophores, and combinations thereof. Any suitable fluorophores can be conjugated with those binding agents, taking care to avoid using two fluorophores with closely-overlapping emission spectra. In some cases, the first fluorophore is fluorescein isothiocyanate, allophycocyanin, or a combination thereof. In further cases, the second fluorophore is a peridinin-chlorophyll-protein complex. Still further cases provide the third fluorophore is R-phycoerythrin. Additional cases provide wherein the fourth fluorophore is fluorescent dye sold under the trademark Alexa Fluor® 647 (Molecular Probes, Inc., Eugene OR). In still further cases, the composition does not contain fluorescent dye sold under the trademark Alexa Fluor® 488 (Molecular Probes, Inc., Eugene OR). The composition may include whole blood from a human patient, for example, when the patient is being assessed for AD.

Kits employing those combinations also appear in the present invention. Thus, another embodiment provides a kit comprising:

a monoclonal antibody for CD11c conjugated with a first fluorophore;
a monoclonal antibody for CD14 conjugated with a second fluorophore;
a monoclonal antibody for CD59 conjugated with a third fluorophore; and
a monoclonal antibody for CD163 conjugated with a fourth fluorophore. And a further embodiment provides a kit comprising:

a monoclonal antibody for CD91 conjugated with a first fluorophore;

a monoclonal antibody for CD14 conjugated with a second fluorophore;

a monoclonal antibody for CD59 conjugated with a third fluorophore; and a monoclonal antibody for CD163 conjugated with a fourth fluorophore.

Those kits can include the binding agents such as antibodies, detectable moieties such as fluorophores, anticoagulants, and additional ingredients as mentioned above. In some instances, the compositions and kits may include the use of particular antibodies, such as, for example, mouse anti-human IgG monoclonal antibodies for those and other biomarkers. Compositions optionally include an anticoagulant and possibly whole human blood. Suitable anticoagulants include, but are not limited to, ethylene diamine tetraacetic acid, at least one salt thereof, citric acid, at least one salt thereof, or a combination of any of the foregoing. The compositions and kits may further include any suitable further ingredients, such as, for example, bovine serum albumin and sodium azide, and phosphate buffered saline, gelatin, and sodium azide as another example.

Suitable fluorophores include those described above. In some cases, the first fluorophore is fluorescein isothiocyanate, allophycocyanin, or a combination thereof. In further cases, the second fluorophore is a peridinin-chlorophyll-protein complex. Additional cases provide R-phycoerythrin as the third fluorophore. Still other cases relate to the fourth fluorophore being fluorescent dye sold under the trademark Alexa Fluor® 647 (Molecular Probes, Inc., Eugene OR).

Methods of using those combinations of biomarkers also appear. Methods for determining the relative expression, diagnosing AD in a human patient, and determining the efficacy of an AD therapeutic candidate as described herein can be employed.

DETAILED DESCRIPTION OF THE DRAWINGS

Further embodiments of the present invention can be understood by reference to the accompanying drawings.

FIG. 1 shows a proposed mechanism. Without wishing to be bound by theory, the proposed mechanism may explain the usefulness of certain embodiments of the present invention. Further elucidation appears in the Discussion below.

EXAMPLES

Testing Biomarkers as Indicative of AD

Applicants examined a suite of common cell-surface leukocyte biomarkers using flow-cytometric techniques for their association with cerebral amyloid-β (Aβ) accumulation as potential biomarkers for AD in a total of 418 human patients. Those patients included 241 cognitively normal (CN), 106 mild cognitive impairment (MCI) and 71 clinically AD dementia patients.

2. Methods:

2.1. Subjects and Ethical Approval

Participants in Phases I, II, and III were recruited from the Australian Imaging, Biomarkers and Lifestyle study (AIBL). This study integrates data from neuroimaging, biomarkers, lifestyle, clinical and neuropsychological analyses. 99% of participants collected by AIBL study are genetic northern European Caucasians who are fluent in English. Classification of the AIBL participants is based on both clinical and neuroimaging/CSF evidence of Aβ accumulation. This study was approved by Human Research Ethics Committee, Research Governance Unit, St Vincent's Hospital, Melbourne, Australia (Ref: HREC-A 028/06). All participants and patient caregivers completed written informed consent before participation. All clinical and demographic information of AIBL participants was masked until the collection of all biological measurements. For Phase IV, the sample was randomly recruited from subjects participating in the Anti-Amyloid Treatment in Asymptomatic Alzheimer's Disease (A4) Study. In this phase, whole blood was obtained from 112 participants who were blindly and randomly selected from the cohort of subjects seen at US sites as part of the screening process for the Anti-Amyloid in Asymptomatic AD (A4) clinical trial (e.g. A4 Biobank Addendum, PI Rissman) [52].

2.2. Aβ-PET Imaging and the Centiloid (CL) Scale

Participants underwent A13-PET imaging as previously described [17, 18]. A 3D T1-weighted MRI was obtained for screening and co-registration with the Aβ-PET images. Researchers involved in blood assessments were blinded to all Aβ-PET and clinical data until reporting of the statistical analyses. Aβ-PET status is based on centiloids (CL): negative <25CL (including borderline >15CL and <25CL) and positive ≥25CL. The thresholds are selected as per their association with risk of disease progression.

2.3. Episodic Memory and Preclinical Alzheimer's Cognitive Composite (PACC) Score The methods used to develop the episodic memory composite and PACC scores are published elsewhere [19, 20].

2.4. Blood Collection

For Phases I-III, peripheral whole blood was collected via venepuncture between 8:00 am and 10:30 am after overnight fasting. Whole blood was kept in EDTA anti-coagulant Vacutainer® tube (Becton Dickinson Biosciences) and was kept on ice during transportation. Processing of whole blood was completed within three hours after collection. For Phase IV, whole blood via venepuncture was collected from overnight fasted participants. Blood collected was shipped overnight on ambient temperature gel packs and processed the following morning for analyses.

2.5. Cell Flow Cytometry Staining

Cell surface staining procedures were carried out using the BD standard protocol: aliquots of 100 µL fresh blood were added into fluorescence-activated cell sorting (FACS®) tubes with pre-mixed antibody cocktails. Mouse anti-human IgG monoclonal antibodies (mAbs) conjugated with fluorophores, which were excited at FITC, PE, PerCP and APC channels, were used to stain leukocytes (Tables A.1s below). An autofluorescence tube containing only whole blood and an IgG isotype control (BD Australia) tube were prepared for each AIBL sample. Optimal concentration for antibodies was determined by titration tests. For intracellular staining, cells were fixed and permeabilized before mixing with antibody cocktail according to the BD standard protocol. Immunophenotyping was performed by flow cytometry using FACSCalibre (BD Biosciences). All flow data were stored in digital form.

2.6. Definition of Phase I, II, III, and IV

Phase I was a triple-color cytometric panel that consisted of 16 surface and 2 intracellular markers. Phase II was a quadruple-color cytometric panel that comprised 18 surface markers. Phase I, II covered some major leukocyte CD markers. Phase III had 19 surface markers and was also a quadruple-color cytometric panel; but was enriched to reflect the emerging evidence that pathways of innate immunity may play a key role in AD pathogenesis. In total, 34 leukocyte markers were examined. Antibody-fluorophore conjugate panels, together with catalogue numbers for the products used, appear in Tables A.1s.

TABLE

A.1.1. Antibody panel for Phase I.

| Phase I | FL1 | FL2 | FL4 |
|---|---|---|---|
| Surface 1 | | Autofluorescence | |
| Surface 2 | IgG₁ (BD#550616) | IgG₁ (BD#554680) | IgG₁ (BD#555751) |
| Surface 3 | CD8 (BD#555366) | CD4 (BD#555347) | CD3 (BD#555342) |
| Surface 4 | CD19 (Dako#F0768) | CD4 (BD#555347) | CD11c (BD#559877) |
| Surface 5 | CD19 (Dako#F0768) | CD11b (BD#555388) | CD4 (BD#555349) |
| Surface 6 | CD40 (BD#555588) | CD11b (BD#555388) | CD14 (BD#340436) |
| Surface 7 | CD16 (BD#555406) | CD11b (BD#555388) | CD14 (BD#340436) |
| Surface 8 | CD15 (BD#555401) | CD11b (BD#555388) | CD14 (BD#340436) |
| Surface 9 | CD8 (BD#555366) | TCRrd (BD#555717) | CD3 (BD#555342) |
| Surface 10 | CD19 (Dako#F0768) | CD4 (BD#555347) | CD34 (BD#555824) |
| Surface 11 | Lin1 (BD#340546) | HLA-DR (BD#347367) | CD11c (BD#559877) |
| Surface 12 | CD14 (BD#347493) | CD16 (Dako#R7012) | ^P2X7 (in house) |
| Intra 1 | | Autofluorescence | |
| Intra 2 | IgG₁ (BD#550616) | IgG₁ (BD#554680) | IgG₁ (BD#555751) |
| Intra 3 | IFN-γ (BD#340449) | CD4 (BD#555347) | CD3 (BD#555342) |
| Intra 4 | *FoxP3 (BD#560047) | CD25 (BD#555432) | CD4 (BD#555349) |

Intra is intracellular staining.

A.1.2. Antibody panel for Phase II.

| Phase II | FL1 | FL2 | FL3 | FL4 |
|---|---|---|---|---|
| Surface 1 | | | Autofluorescence | |
| Surface 2 | IgG1 (BD#550616) | IgG1 (BD#554680) | IgG1 (BD#550672) | IgG1 (BD#555751) |
| Surface 3 | CD19 (Dako#F0768) | #CD16 (Dako#R7012) | CD14 (BD#340585) | CD11c (BD#559877) |
| Surface 4 | CD15 (BD#555401) | CD11b (BD#555388) | CD14 (BD#340585) | CD16 (BD#561304) |
| Surface 5 | CD19 (Dako#F0768) | CD33 (BD#347787) | CD14 (BD#340585) | CD34 (BD#555824) |
| Surface 6 | CD16 (BD#555406) | CD4 (BD#555347) | CD14 (BD#340585) | ^P2X7 (in house) |
| Surface 7 | Lin1 (BD#340546) | HLA-DR (BD#347367) | CD69 (BD#340548) | CD11c (BD#559877) |
| Surface 8 | CD8 (BD#555366) | TCRrd (BD#555717) | CD4 (BD#347324) | CD3 (BD#555342) |
| Surface 9 | CD127 (BD#560549) | CD25 (BD#555432) | CD4 (BD#347324) | CD14 (BD#340436) |

A.1.3. Antibody panel for Phase III.

| Phase III | FL1 | FL2 | FL3 | FL4 |
|---|---|---|---|---|
| Surface 1 | | | Autofluorescence | |
| Surface 2 | IgG1 (BD#550616) | IgG1 (BD#554680) | IgG1 (BD#550672) | IgG1 (BD#555751) |
| Surface 3 | CD16 (BD#555406) | SCARA1 (RD#FAB2708P) | | CD14 (BD#340436) |
| Surface 4 | CD68 (BD#562117) | CD16 (Dako#R7012) | CD14 (BD#340585) | MerTK (RD#FAB8912A) |
| Surface 5 | CD16 (BD#555406) | CD11B (BD#555388) | CD14 (BD#340585) | CD11C (BD#559877) |
| Surface 6 | | CD16 (Dako#R7012) | CD14 (BD#340585) | CD35 (BD#565329) |
| Surface 7 | | CD16 (Dako#R7012) | CD14 (BD#340585) | ^P2X7 (in house) |
| Surface 8 | CD16 (BD#555406) | CD59 (BD#555764) | CD14 (BD#340585) | ^CD163 (BD#562669) |
| Surface 9 | CD36 (BD#555454) | CD91 (BD#550497) | CD14 (BD#340585) | CD16 (BD#561304) |
| Surface 10 | CD16 (BD#555406) | CD44 (BD#555479) | CD4 (BD#347324) | CD14 (BD#340436) |
| Surface 11 | CD18 (BD#555923) | CD16 (Dako#R7012) | CD14 (BD#340585) | RAGE (LS-C212626) |
| Surface 12 | CD16 (BD#555406) | CX3CR1 (BD#565796) | CD14 (BD#340585) | ^CCR2 (BD#558406) |

In Tables A.1s, FL1, FL2, FL3 and FL4 are fluorescence detection channels of BD FACSCalibur.
The fluorochromes for FL1, FL2, FL3, and FL4 are FITC, PE, PerCP and APC, or equivalent.
*FoxP3 is labelled with Alexa Fluor ® 488.
^ represents antibody is labelled with Alexa Fluor ® 647.
BD is Becton Dickinson Biosciences.
Dako is Agilent Dako.
RD is R&D Systems.
LS is LifeSpan Biosciences.

A.1.4 Antibody Panel for Phase IV

| Panel of tubes | FL1 | FL2 | FL3 | FL4 |
|---|---|---|---|---|
| Surface 1 | | | Autofluorescence | |
| Surface 2 | IgG1 (BD#550616) | IgG1 (BD#554680) | IgG1 (BD#550672) | IgG1 (BD#555751) |
| Surface 3 | CD11c (BD#561355) | CD59 (BD#555764) | CD14 (BD#340585) | ^CD163 (BD#562669) |
| Surface 4 | CD91 (BD#550496) | CD59 (BD#555764) | CD14 (BD#340585) | ^CD163 (BD#562669) |

FL1, FL2, FL3 and FL4 are fluorescence detection channels of BD FACSCalibur.
The fluorochromes for FL1, FL2, FL3, and FL4 are FITC, PE, PerCP and APC, or equivalent.
*FoxP3 is labelled with Alexa Fluor ® 488; A represents antibody is labelled with Alexa Fluor ® 647.
BD is Becton Dickinson Biosciences; Dako is Agilent Dako; RD is R&D Systems;
LS is LifeSpan Biosciences.

Flow data was analysed using FlowJo software (V10, FlowJo, LLC). Applicants used forward scatter, side scatter to gate lymphocytes, monocytes and neutrophils. Subpopulations were then gated based on fluorescent intensity of specific markers. In Phase III, Applicants used fluorescent intensity of anti-CD14 and anti-CD16 mAbs to gate natural killer (NK) cells, B and T lymphocytes, classical monocytes, intermediate monocytes, non-classical monocytes, mature neutrophils, and immature neutrophils. Cell count and frequency of subpopulations were calculated. The mean fluorescent intensity (MFI) of different markers on different cell groups was also measured.

2.7. Statistical Analysis

Statistical analysis was performed in GraphPad Prism for Windows (Version 8.4.2, San Diego, California USA) and IBM SPSS® Statistics Software (Version 25.0 Armonk, NY: IBM Corp). Fluorescent intensity of mAbs was compared between CN, MCI and AD groups using One-way ANOVA. Pearson product-moment correlational analysis was performed to examine the strength of relationship between fluorescent intensity of mAbs and PET Aβ centiloid, episodic memory and PACC score. For the predictive analyses, Receiver Operating Characteristic (ROC) analyses was used to define values of sensitivity, specificity and accuracy. Thresholds were chosen via Youden's Index. Models were calculated for individual biomarkers, individual biomarkers adjusted for covariates and combinatorial sets of biomarkers to predict outcome post Logistic Regression. Figures were created in GraphPad Prism for Windows (Version 8.4.2, San Diego, California USA) and statistical analyses were conducted using R (version 4.0).

2.8 Biomarker Assessment

Here Applicants try to discover whether adding new biomarkers can better predict disease risk. Applicants assessed biomarker performance in a logistic regression model created with the rms R package and assessed with the rap R package. R version 4.0.2 was used. The added value of biomarkers to a baseline model were assessed using the change in area under the receiver operator characteristic curve (AUC), the integrated discrimination improvement (IDI) metrics, and the Brier skill score. The change in AUC reflects the change in ranking of the probabilities of the baseline model and the new model. The IDI are presented separately for those with and without the event of interest. They represent the net mean increase in risk for those with the event (IDI event) and mean decrease in risk for those without the event (IDI non-event). The Brier improvement is the relative improvement of the Brier score from the baseline model. The Brier score is the mean squared error of the model and the Brier improvement gives the percent improvement in accuracy with the addition of the biomarker.

The process of model creation was, in brief, to construct an artificial baseline logistic regression model to predict subjects' brain Aβ-PET status. First, variables were chosen by a variable-reduction technique, principal component regression, which reduced the number of variables by shrinking neuropsychological diagnoses together with demographics (i.e., age, sex and year of education). Second, Applicants added each biomarker one by one to the baseline model to assess if the new biomarker improved the diagnostic performance of the baseline model. These are the "new models." Finally, Applicants combined the best performing biomarkers into a panel of biomarkers to achieve the optimal performance. Here Applicants defined disease state simply by centiloids >25CL for Phase III Model 1. Phase III Model 2 sought to explore whether certain biomarkers had physiological value that helps either with differentiation of disease early stage (i.e., borderline). However, the AIBL borderline range, >15CL & <25CL, was too narrow to include enough cases. Therefore, Applicants arbitrarily defined early stage of AD by centiloids ≥25CL & <100CL; and the individuals with centiloids >100CL were removed. Model 3 further considered patients' clinical status alongside their Aβ status to stratify study cohort into healthy controls (CN & <25CL), preclinical (CN & ≥25CL), or prodromal (MCI & Not considering CL) and AD (Not considering CL) stages. Then, Applicants arbitrarily defined disease status for model 3 by combining preclinical and prodromal stages (AD stage was removed). Data skewness was tested by Kolmogorov-Smirnova and Shapiro-Wilk methods.

3. Results:

3.1. Demographics

This cross-sectional study comprised four phases, in which Phase I, II served as discovery data sets and Phase III, IV as validation data sets. Applicants recruited 76, 142 and 200 participants from the AIBL study in Phases I, II, and III, and 112 participants from the A4 study in Phase IV. All data sets included a balanced number of individuals clinically classified as CN, MCI and AD dementia. All samples had corresponding Aβ-PET and cognitive data. Study demographics were simply stratified by high or low Aβ burden, except for Phase III models 2 and 3 (see Methods 2.8).

3.2. Candidate Biomarkers in Phases I and II

Phase I identified CD11c and P2X7 as candidate biomarkers (Table A.2.1 below). The MFI of CD11c decreased by 19-34% (P<0.05) and P2X7 decreased by 20-42% (P<0.01) in MCI and AD groups compared to that of CN group. They also showed a negative correlation with Aβ CL such that the higher Aβ load subjects had lower expression levels of CD11c and P2X7. Phase II identified CD11c, CD11 b and CD33, but not P2X7 as candidate biomarkers (Table A.2.2 below). The MFI of CD11c, CD11b and CD33 decreased in MCI and AD groups by 14-23% (P<0.05), 14-21% (P<0.05) and 16-18% (P<0.05), individually, compared to CN group. However, only CD11c on NK cells correlated with Aβ-PET data.

3.3 Candidate Biomarkers in Phase III

In Phase III, Applicants identified ten candidate markers related to the MFI of CD11c, CD59, CD91 and CD163 that were different between CN, MCI and AD groups (top 10 in Table A.2.3 below) and correlated with the Aβ burden. The MFI of CD11c and CD163 decreased by 15-19% (P<0.01) and 11-16% (P<0.01), respectively, in MCI and AD groups compared to that of CN group, while the MFI of CD59 and CD91 increased by 27-78% (P<0.0001) and 44-59% (P<0.001), respectively, in MCI and AD groups. The bottom four in Table A.2.3 related to MerTK, CD18 and RAGE were excluded because of small sample sizes. Nevertheless, the MFI of CD18 and MerTK decreased by 20-26% (P<0.05) and 12% (P<0.05), respectively and the MFI of RAGE increased on monocytes by 31% (P<0.05) in MCI and AD groups compared to CN group. Changes of all potential biomarkers and their relevance to AD are listed in Table 1 above.

The absolute percentage of CD14-lymphocytes in whole blood was lowered by 11% (P<0.01) in MCI and AD groups compared to CN group (Table A.2.4 below) and was correlated with CL, episodic memory and PACC scores. The differences in the percentage of monocytes in whole blood between CN, MCI and AD groups were trivial, so Applicants divided the whole monocyte population into CD14+CD16+, CD14+CD16− and CD14−CD16+ subpopulations and evaluated their relative percentage from the whole monocyte population. The relative percentage of CD14+CD16− monocytes was increased by 13% (P<0.01) in AD and MCI groups compared to CN group (Table A.2.4). Interestingly, the relative percentage of CD14+CD16+ monocytes decreased by 30% (P=0.02) in MCI groups compared to CN group, but AD and CN did not show any group differences. A lower relative percentage of CD14− CD16+ monocytes in MCI group (−29% P=0.02) was also observed in another tube with smaller sample size. Thereafter, the percentages of CD14− lymphocytes and CD14+CD16− monocytes were added to the ten, making twelve biomarkers for further assessment.

TABLE A.2.1

Phase I differences of mean fluorescent intensity and standard deviation of CD11c and P2X7 in CN, MCI and AD.

| Markers | CN | MCI | AD | MCI&AD | Change of MCI & AD (%) |
|---|---|---|---|---|---|
| CD11c on lym | 8.61 ± 2.48 | 7.17 ± 1.51 | 6.66 ± 1.31 | 6.98 ± 1.43 | −19 |
| CD11c on mono | 73.67 ± 37.28 | 47.99 ± 15.14 | 50.31 ± 7.94 | 48.87 ± 12.77 | −34 |
| CD11c on neutro | 21.43 ± 8.71 | 15.26 ± 4.95 | 16.04 ± 4.52 | 15.56 ± 4.72 | −27 |
| P2X7 on lym | 17.03 ± 4.72 | 13.02 ± 1.99 | 13.25 ± 2.13 | 13.11 ± 2.01 | −23 |
| P2X7 on NK | 21.34 ± 7.7 | 14.58 ± 2.44 | 15.36 ± 4.11 | 14.88 ± 3.13 | −30 |
| P2X7 on T&B | 16.21 ± 4.34 | 12.82 ± 1.88 | 13.06 ± 1.95 | 12.91 ± 1.88 | −20 |
| P2X7 on CD14− CD16+ mono | 40.58 ± 20.37 | 24.96 ± 6.03 | 27.08 ± 12.69 | 25.8 ± 9.07 | −36 |
| P2X7 onCD14+ CD16− mono | 70.7 ± 40.01 | 40.02 ± 10.53 | 42.48 ± 20.76 | 40.99 ± 15.06 | −42 |
| P2X7 on neutro | 32.67 ± 14.37 | 23.31 ± 2.45 | 23.78 ± 4.46 | 23.48 ± 3.24 | −28 |
| P2X7 on CD14− CD16+ neutro | 31.08 ± 12.08 | 22.82 ± 2.51 | 23.31 ± 4.33 | 23 ± 3.21 | −26 |

Lym: lymphocytes.
NK: natural killer cells.
T&B: T cells and B cells.
Mono: monocytes.
Neutro: neutrophils.

TABLE A.2.2

Phase II differences of mean fluorescent intensity and standard deviation of CD11c, CD11b and CD33 in CN, MCI and AD.

| Markers | CN | MCI | AD | MCI &AD | Change of MCI & AD (%) |
|---|---|---|---|---|---|
| CD11c on NK | 24.83 ± 11.46 | 18.81 ± 7.16 | 19.48 ± 7.36 | 19.11 ± 7.21 | −23 |
| CD11c on CD19− CD14+ CD16+ mono | 129.39 ± 39.77 | 107.15 ± 34.81 | 102.28 ± 27.75 | 105.05 ± 31.84 | −19 |
| CD11c on neutro | 22.01 ± 5.69 | 19.02 ± 5.41 | 18.81 ± 6.16 | 18.92 ± 5.73 | −14 |
| CD11c on CD14− CD16+ neutro | 27.22 ± 6.55 | 23.33 ± 6.22 | 22.41 ± 6.75 | 22.91 ± 6.44 | −16 |
| CD11c on CD14− CD16− neutro | 20.94 ± 7.79 | 18.52 ± 6.66 | 15.88 ± 4.87 | 17.34 ± 6.04 | −17 |
| CD11b on CD15− T&B | 17.39 ± 6.34 | 15.22 ± 4.92 | 14.63 ± 4.43 | 14.95 ± 4.68 | −14 |
| CD11b on CD15+ mono* | 399.69 ± 124.42 | 319.89 ± 74.43 | 307.63 ± 79.39 | 314.12 ± 76.47 | −21 |
| CD11b on CD15− mono | 345.5 ± 118.92 | 294.47 ± 76.26 | 292.72 ± 76.12 | 93.67 ± 75.64 | −15 |
| CD11b on CD15− CD14+ CD16− mono | 378.83 ± 136.7 | 321.79 ± 86.51 | 318.72 ± 85.98 | 320.39 ± 85.65 | −15 |
| CD11b on CD15+ CD14− neutro | 516.45 ± 124.25 | 432.55 ± 88.13 | 419.03 ± 99.88 | 426.37 ± 93.23 | −17 |
| CD33 on mono | 232.55 ± 93.31 | 190.62 ± 83.82 | 188.46 ± 100.44 | 189.65 ± 90.99 | −18 |
| CD33 on neutro | 34.66 ± 11.76 | 29.87 ± 10.59 | 28 ± 11.16 | 29.03 ± 10.82 | −16 |

Lym: lymphocytes.
NK: natural killer cells.
T&B: T cells and B cells.
Mono: monocytes.
Neutro: neutrophils.
*Only 10-15% of subjects were found to weakly express CD15 on their monocytes.

TABLE A.2.3

Phase III differences of mean fluorescent intensity and standard deviation of CD11c, CD59, CD163, CD91, MerTK, CD18 and RAGE in CN, MCI and AD.

| Markers | CN | MCI | AD | AD&MCI | % |
|---|---|---|---|---|---|
| CD11c on NK | 14.58 ± 4.7 | 12.01 ± 4.63 | 11.7 ± 5.34 | 11.87 ± 4.92 | −19 |
| CD11c on CD14− CD16+ mono | 57.35 ± 22.02 | 47.29 ± 18.78 | 47.22 ± 28.09 | 47.26 ± 23.22 | −18 |

TABLE A.2.3-continued

Phase III differences of mean fluorescent intensity and standard deviation of CD11c,
CD59, CD163, CD91, MerTK, CD18 and RAGE in CN, MCI and AD.

| Markers | CN | MCI | AD | AD&MCI | % |
|---|---|---|---|---|---|
| CD11c on CD14– neutro | 11.81 ± 3.71 | 9.79 ± 3.21 | 10.33 ± 3.54 | 10.03 ± 3.34 | –15 |
| CD59 on T&B | 7.9 ± 2.14 | 13.22 ± 6.12 | 15.11 ± 6.52 | 14.06 ± 6.33 | 78 |
| CD59 on CD14– CD16+ mono | 10.28 ± 3.05 | 14.74 ± 4.74 | 14.61 ± 4.81 | 14.68 ± 4.74 | 43 |
| CD59 on CD14– CD16+ neutro | 16.64 ± 3.35 | 20.56 ± 6.41 | 21.73 ± 6.72 | 21.08 ± 6.53 | 27 |
| CD163 on CD14+ CD16– mono | 165.03 ± 43.75 | 139.16 ± 48.79 | 139.76 ± 35.52 | 139.43 ± 43.11 | –16 |
| CD163 onCD14– neutro | 13.75 ± 2.71 | 12.18 ± 2.69 | 12.31 ± 1.58 | 12.24 ± 2.25 | –11 |
| CD91 on NK | 4.03 ± 1.63 | 5.51 ± 2.84 | 6.1 ± 3.9 | 5.78 ± 3.36 | 44 |
| CD91 on CD14+ CD16+ mono | 175.2 ± 59.23 | 255.02 ± 114.66 | 304.57 ± 121.16 | 277.89 ± 119.4 | 59 |
| MerTK on CD14– CD16– neutro | 6.85 ± 2.04 | 5.99 ± 0.96 | 6.1 ± 1.04 | 6.04 ± 0.99 | –12 |
| CD18 on NK | 232.13 ± 57.55 | 189.42 ± 40 | 179.42 ± 47.42 | 185 ± 43.19 | –20 |
| CD18 on T&B | 96.64 ± 28.1 | 68.62 ± 20.98 | 75.17 ± 34.45 | 71.51 ± 27.58 | –26 |
| RAGE on CD14– CD16+ mono | 6.64 ± 1.7 | 8.26 ± 2.6 | 9.21 ± 1.99 | 8.68 ± 2.38 | 31 |

Lym: lymphocytes.
NK: natural killer cells.
T&B: T cells and B cells
Mono: monocytes.
Neutro: neutrophils.

TABLE A.2.4

Phase III differences of blood cell percentage and
standard deviation in CN, MCI and AD.

| Markers | CN | MCI | AD | AD&MCI | % |
|---|---|---|---|---|---|
| Absolute % lym | 0.28 ± 0.07 | 0.25 ± 0.07 | 0.24 ± 0.09 | 0.25 ± 0.08 | –11 |
| Relative % CD14+CD16– mono | 0.57 ± 0.12 | 0.64 ± 0.11 | 0.66 ± 0.1 | 0.65 ± 0.11 | 13 |

3.5. Biomarker Assessment

In Tables 3s, the twelve selected biomarkers in Phase III were named as Biomarker 1 (BM1), Biomarker 2 (BM2), . . . and Biomarker12 (BM12). Distribution tests found that Biomarker7 and Biomarker 8 nearly followed normal distributions (Tables A.6s). Others were transformed by using both natural logarithm (lnBM) and square root (sqrtBM). Collinearity test was used to choose only independent biomarkers when combining them into a panel (Tables A.7s).

TABLE 3.1

Phase III: Model 1 biomarker performance.

| Biomarkers | Descriptives | Division of biomarkers | Goodness of fit (original)ᵃ | Goodness of fit (corrected) | AUC.orig (95% CI) | AUC.corrected (95% CI) | Brier. Improvement | IDI.events (95% CI) | IDI.nonevents (95% CI) |
|---|---|---|---|---|---|---|---|---|---|
| Baseline1 | Demographics (Age, Sex, Ed, Psy) | Reference | 0.39 | 0.35 | 0.85 (0.79 to 0.91) | 0.81 (0.76 to 0.88) | NA | NA | NA |
| Biomarker1 | CD11c on NK cells | CD11c | 0.47 | 0.40 | 0.86 (0.8 to 0.91) | 0.83 (0.77 to 0.9) | 4 | 0.047 (0.03 to 0.063) | –0.006 (–0.022 to 0.011) |
| lnBM1 | | CD11c | 0.47 | 0.40 | 0.85 (0.8 to 0.91) | 0.83 (0.79 to 0.9) | 3.7 | 0.045 (0.029 to 0.061) | –0.007 (–0.022 to 0.008) |
| sqrtBM1 | | CD11c | 0.47 | 0.40 | 0.86 (0.8 to 0.91) | 0.84 (0.77 to 0.91) | 4 | 0.046 (0.03 to 0.062) | –0.006 (–0.022 to 0.01) |
| Biomarker2 | CD11c on non-classical monocytes | CD11c | 0.47 | 0.40 | 0.86 (0.8 to 0.91) | 0.83 (0.78 to 0.9) | 4.6 | 0.047 (0.029 to 0.064) | –0.006 (–0.02 to 0.009) |
| lnBM2 | | CD11c | 0.47 | 0.41 | 0.86 (0.8 to 0.91) | 0.84 (0.79 to 0.91) | 4.6 | 0.048 (0.03 to 0.067) | –0.004 (–0.02 to 0.012) |
| sqrtBM2 | | CD11c | 0.47 | 0.42 | 0.86 (0.8 to 0.92) | 0.84 (0.78 to 0.9) | 4.2 | 0.048 (0.03 to 0.066) | –0.005 (–0.02 to 0.01) |
| Biomarker3 | CD11c on neutrophils | CD11c | 0.49 | 0.43 | 0.86 (0.8 to 0.92) | 0.84 (0.79 to 0.91) | 6.2 | 0.055 (0.035 to 0.075) | 0.001 (–0.02 to 0.022) |
| lnBM3 | | CD11c | 0.49 | 0.43 | 0.86 (0.8 to 0.92) | 0.84 (0.78 to 0.9) | 6.6 | 0.054 (0.033 to 0.075) | 0.001 (–0.02 to 0.021) |
| sqrtBM3 | | CD11c | 0.49 | 0.43 | 0.86 (0.8 to 0.92) | 0.84 (0.78 to 0.91) | 6.4 | 0.054 (0.034 to 0.075) | 0.001 (–0.02 to 0.022) |

TABLE 3.1-continued

| | | | | Phase III: Model 1 biomarker performance. | | | | |
|---|---|---|---|---|---|---|---|---|
| Biomarkers | Descriptives | Division of biomarkers | Goodness of fit (original)[a] | Goodness of fit (corrected) | AUC.orig (95% CI) | AUC.corrected (95% CI) | Brier. Improvement | IDI.events (95% CI) | IDI.nonevents (95% CI) |
| Biomarker4 | CD59 on T&B lymphocytes | CD59 | 0.49 | 0.43 | 0.87 (0.82 to 0.93) | 0.85 (0.78 to 0.92) | 7.7 | 0.037 (0.014 to 0.059) | 0.017 (0.003 to 0.031) |
| lnBM4 | | CD59 | 0.49 | 0.42 | 0.86 (0.81 to 0.92) | 0.84 (0.79 to 0.91) | 7.4 | 0.032 (0.013 to 0.051) | 0.012 (0 to 0.025) |
| sqrtBM4 | | CD59 | 0.49 | 0.42 | 0.87 (0.81 to 0.93) | 0.84 (0.8 to 0.92) | 7.3 | 0.034 (0.014 to 0.055) | 0.015 (0.001 to 0.028) |
| Biomarker5 | CD59 on non-classical monocytes | CD59 | 0.48 | 0.40 | 0.86 (0.81 to 0.92) | 0.84 (0.79 to 0.91) | 5.5 | 0.032 (0.015 to 0.048) | 0.012 (−0.002 to 0.027) |
| lnBM5 | | CD59 | 0.48 | 0.41 | 0.86 (0.8 to 0.92) | 0.84 (0.79 to 0.91) | 7.5 | 0.031 (0.015 to 0.048) | 0.012 (−0.003 to 0.026) |
| sqrtBM5 | | CD59 | 0.48 | 0.42 | 0.86 (0.81 to 0.92) | 0.84 (0.79 to 0.92) | 6.9 | 0.032 (0.015 to 0.049) | 0.012 (−0.002 to 0.027) |
| Biomarker6 | CD59 on neutrophils | CD59 | 0.48 | 0.43 | 0.87 (0.81 to 0.92) | 0.85 (0.78 to 0.91) | 6.5 | 0.031 (0.014 to 0.048) | 0.011 (−0.002 to 0.024) |
| lnBM6 | | CD59 | 0.48 | 0.41 | 0.86 (0.8 to 0.92) | 0.84 (0.78 to 0.91) | 5.2 | 0.027 (0.013 to 0.041) | 0.008 (−0.003 to 0.019) |
| sqrtBM6 | | CD59 | 0.48 | 0.40 | 0.86 (0.81 to 0.92) | 0.84 (0.79 to 0.91) | 5.7 | 0.029 (0.013 to 0.045) | 0.01 (−0.002 to 0.022) |
| Biomarker7 | CD163 on classical monocytes | CD163 | 0.47 | 0.41 | 0.86 (0.8 to 0.92) | 0.84 (0.78 to 0.91) | 5.3 | 0.027 (0.014 to 0.041) | 0.008 (−0.003 to 0.019) |
| lnBM7 | | CD163 | 0.47 | 0.40 | 0.86 (0.8 to 0.92) | 0.84 (0.78 to 0.91) | 6 | 0.026 (0.013 to 0.039) | 0.007 (−0.003 to 0.017) |
| sqrtBM7 | | CD163 | 0.47 | 0.41 | 0.86 (0.8 to 0.92) | 0.84 (0.77 to 0.91) | 5.6 | 0.027 (0.013 to 0.04) | 0.008 (−0.003 to 0.018) |
| Biomarker8 | CD163 on neutrophils | CD163 | 0.55 | 0.48 | 0.89 (0.83 to 0.94) | 0.86 (0.81 to 0.93) | 12.7 | 0.057 (0.022 to 0.091) | 0.039 (0.013 to 0.064) |
| lnBM8 | | CD163 | 0.56 | 0.49 | 0.89 (0.84 to 0.94) | 0.87 (0.83 to 0.94) | 16 | 0.06 (0.024 to 0.096) | 0.041 (0.015 to 0.067) |
| sqrtBM8 | | CD163 | 0.55 | 0.49 | 0.89 (0.84 to 0.94) | 0.87 (0.82 to 0.93) | 15.6 | 0.058 (0.023 to 0.093) | 0.04 (0.014 to 0.066) |
| Biomarker9 | CD91 on NK cells | CD91 | 0.47 | 0.38 | 0.86 (0.79 to 0.92) | 0.83 (0.77 to 0.91) | 1.8 | 0.046 (0.021 to 0.07) | 0.005 (−0.021 to 0.032) |
| lnBM9 | | CD91 | 0.48 | 0.40 | 0.86 (0.79 to 0.93) | 0.83 (0.78 to 0.92) | 1.6 | 0.048 (0.023 to 0.074) | 0.008 (−0.021 to 0.036) |
| sqrtBM9 | | CD91 | 0.48 | 0.39 | 0.86 (0.79 to 0.92) | 0.83 (0.77 to 0.91) | 0.6 | 0.047 (0.022 to 0.072) | 0.007 (−0.021 to 0.034) |
| Biomarker10 | CD91 on intermediate monocytes | CD91 | 0.48 | 0.39 | 0.86 (0.79 to 0.93) | 0.83 (0.77 to 0.93) | 3.4 | 0.047 (0.021 to 0.073) | 0.013 (−0.014 to 0.039) |
| lnBM10 | | CD91 | 0.48 | 0.40 | 0.86 (0.79 to 0.93) | 0.83 (0.77 to 0.92) | 4.3 | 0.048 (0.022 to 0.074) | 0.014 (−0.014 to 0.041) |
| sqrtBM10 | | CD91 | 0.48 | 0.40 | 0.86 (0.79 to 0.93) | 0.83 (0.76 to 0.91) | 2.5 | 0.048 (0.022 to 0.073) | 0.013 (−0.014 to 0.04) |
| Biomarker11 | % of lymphocytes in whole leukocytes | % Lymphocyte | 0.48 | 0.42 | 0.87 (0.81 to 0.92) | 0.84 (0.79 to 0.92) | 4.7 | 0.03 (0.013 to 0.047) | 0.011 (−0.003 to 0.024) |
| lnBM11 | | % Lymphocyte | 0.48 | 0.41 | 0.87 (0.81 to 0.92) | 0.84 (0.79 to 0.91) | 3.6 | 0.03 (0.013 to 0.047) | 0.011 (−0.003 to 0.024) |
| sqrtBM11 | | % Lymphocyte | 0.48 | 0.42 | 0.87 (0.81 to 0.92) | 0.84 (0.79 to 0.91) | 5.8 | 0.03 (0.013 to 0.047) | 0.011 (−0.003 to 0.024) |
| Biomarker12 | % of classical monocytes in total monocytes | % Monocyte | 0.48 | 0.40 | 0.86 (0.79 to 0.92) | 0.83 (0.77 to 0.91) | 3 | 0.048 (0.02 to 0.075) | 0.013 (−0.015 to 0.041) |
| lnBM12 | | % Monocyte | 0.48 | 0.40 | 0.86 (0.79 to 0.92) | 0.83 (0.78 to 0.91) | 2.5 | 0.047 (0.02 to 0.074) | 0.012 (−0.015 to 0.04) |
| sqrtBM12 | | % Monocyte | 0.48 | 0.40 | 0.86 (0.79 to 0.92) | 0.86 (0.78 to 0.92) | 3.1 | 0.047 (0.02 to 0.075) | 0.013 (−0.015 to 0.041) |
| New1 | Age, Sex, Ed, Psy, lnBM8, lnBM5, lnBM3 | Reference, CD163, CD59 & CD11c | 0.61 | 0.54 | 0.91 (0.86 to 0.95) | 0.88 (0.84 to 0.94) | 17.8 | 0.085 (0.049 to 0.122) | 0.05 (0.019 to 0.081) |

Psy is Neuropsych.SimpleClassification.
[a]A Hosmer-Lemeshow goodness of fit was used to test calibration of the model.
Ln is natural logarithm of the biomarker and sqrt is square root of the biomarker.
Underscores are best performance biomarkers.
Baseline1 is the baseline of Phase III: Model 1.
New1 is a proposed panel of biomarkers for Phase III: Model 1.

TABLE 3.2

Phase III: Model 2 biomarker performance.

| Biomarkers | Descriptives | Goodness of fit (original)[a] | Goodness of fit (corrected) | AUC.orig (95% CI) | AUC.corrected (95% CI) | Brier. Improvement | IDI.events (95% CI) | IDI.nonevents (95% CI) |
|---|---|---|---|---|---|---|---|---|
| Baseline2 | Demographics (Age, Sex, Ed, Psy) | 0.32 | 0.26 | 0.84 (0.77 to 0.91) | 0.78 (0.71 to 0.87) | NA | NA | NA |
| Biomarker1 | CD11c on NK cells | 0.46 | 0.39 | 0.85 (0.78 to 0.93) | 0.83 (0.74 to 0.91) | 9.8 | 0.067 (0.038 to 0.097) | 0.011 (−0.007 to 0.029) |
| lnBM1 | | 0.45 | 0.38 | 0.85 (0.78 to 0.92) | 0.83 (0.76 to 0.91) | 9.8 | 0.065 (0.036 to 0.094) | 0.01 (−0.007 to 0.027) |
| sqrtBM1 | | 0.46 | 0.37 | 0.85 (0.78 to 0.93) | 0.83 (0.76 to 0.91) | 10.1 | 0.066 (0.037 to 0.096) | 0.01 (−0.007 to 0.028) |
| Biomarker2 | CD11c on non-classical monocytes | 0.48 | 0.40 | 0.87 (0.8 to 0.94) | 0.84 (0.77 to 0.92) | 13.8 | 0.082 (0.042 to 0.121) | 0.018 (−0.002 to 0.038) |
| lnBM2 | | 0.48 | 0.40 | 0.87 (0.8 to 0.93) | 0.84 (0.77 to 0.92) | 13.1 | 0.082 (0.044 to 0.121) | 0.018 (−0.003 to 0.04) |
| sqrtBM2 | | 0.48 | 0.40 | 0.87 (0.8 to 0.94) | 0.84 (0.77 to 0.92) | 14.2 | 0.083 (0.044 to 0.123) | 0.019 (−0.002 to 0.039) |
| Biomarker3 | CD11c on neutrophils | 0.48 | 0.40 | 0.86 (0.79 to 0.93) | 0.84 (0.76 to 0.93) | 14.7 | 0.082 (0.047 to 0.117) | 0.018 (−0.003 to 0.04) |
| lnBM3 | | 0.47 | 0.39 | 0.86 (0.79 to 0.93) | 0.83 (0.76 to 0.92) | 15.2 | 0.079 (0.044 to 0.115) | 0.017 (−0.003 to 0.037) |
| sqrtBM3 | | 0.48 | 0.40 | 0.86 (0.79 to 0.93) | 0.83 (0.75 to 0.91) | 14.4 | 0.081 (0.045 to 0.116) | 0.018 (−0.003 to 0.039) |
| Biomarker4 | CD59 on T&B lymphocytes | 0.45 | 0.35 | 0.86 (0.79 to 0.93) | 0.82 (0.76 to 0.92) | 4.4 | 0.046 (0.023 to 0.068) | 0.014 (0.001 to 0.027) |
| lnBM4 | | 0.45 | 0.36 | 0.85 (0.78 to 0.92) | 0.82 (0.76 to 0.91) | 5.4 | 0.045 (0.024 to 0.066) | 0.014 (0.001 to 0.026) |
| sqrtBM4 | | 0.45 | 0.36 | 0.86 (0.79 to 0.92) | 0.82 (0.76 to 0.91) | 5.2 | 0.045 (0.024 to 0.067) | 0.014 (0.001 to 0.026) |
| Biomarker5 | CD59 on non-classical monocytes | 0.47 | 0.37 | 0.87 (0.8 to 0.93) | 0.83 (0.77 to 0.93) | 9.5 | 0.056 (0.03 to 0.082) | 0.019 (0.003 to 0.035) |
| lnBM5 | | 0.46 | 0.37 | 0.86 (0.79 to 0.93) | 0.83 (0.76 to 0.91) | 8 | 0.052 (0.028 to 0.077) | 0.017 (0.002 to 0.032) |
| sqrtBM5 | | 0.46 | 0.36 | 0.86 (0.8 to 0.93) | 0.83 (0.76 to 0.92) | 7.1 | 0.054 (0.029 to 0.08) | 0.018 (0.002 to 0.034) |
| Biomarker6 | CD59 on neutrophils | 0.45 | 0.36 | 0.85 (0.78 to 0.92) | 0.82 (0.75 to 0.9) | 6.3 | 0.045 (0.024 to 0.066) | 0.014 (0.001 to 0.026) |
| lnBM6 | | 0.45 | 0.35 | 0.85 (0.78 to 0.92) | 0.82 (0.76 to 0.92) | 6.8 | 0.047 (0.025 to 0.069) | 0.015 (0.001 to 0.028) |
| sqrtBM6 | | 0.45 | 0.35 | 0.85 (0.78 to 0.92) | 0.82 (0.75 to 0.92) | 5.2 | 0.046 (0.025 to 0.067) | 0.014 (0.001 to 0.027) |
| Biomarker7 | CD163 on classical monocytes | 0.45 | 0.35 | 0.85 (0.78 to 0.92) | 0.82 (0.76 to 0.91) | 6.9 | 0.046 (0.023 to 0.069) | 0.014 (0.001 to 0.027) |
| lnBM7 | | 0.45 | 0.36 | 0.85 (0.78 to 0.92) | 0.82 (0.76 to 0.92) | 6.2 | 0.045 (0.024 to 0.066) | 0.014 (0.001 to 0.026) |
| sqrtBM7 | | 0.45 | 0.36 | 0.85 (0.78 to 0.92) | 0.82 (0.76 to 0.92) | 6 | 0.046 (0.024 to 0.068) | 0.014 (0.001 to 0.027) |
| Biomarker8 | CD163 on neutrophils | 0.55 | 0.46 | 0.9 (0.84 to 0.95) | 0.86 (0.81 to 0.95) | 19.7 | 0.101 (0.047 to 0.156) | 0.049 (0.022 to 0.075) |
| lnBM8 | New2 | 0.56 | 0.48 | 0.9 (0.84 to 0.96) | 0.87 (0.82 to 0.94) | 20 | 0.106 (0.05 to 0.162) | 0.051 (0.024 to 0.077) |
| sqrtBM8 | | 0.56 | 0.47 | 0.9 (0.84 to 0.96) | 0.87 (0.81 to 0.94) | 19.4 | 0.104 (0.048 to 0.159) | 0.05 (0.023 to 0.076) |
| Biomarker9 | CD91 on NK cells | 0.46 | 0.34 | 0.85 (0.77 to 0.93) | 0.81 (0.74 to 0.92) | 1.4 | 0.089 (0.049 to 0.128) | 0.003 (−0.022 to 0.028) |
| lnBM9 | | 0.47 | 0.36 | 0.86 (0.78 to 0.94) | 0.82 (0.75 to 0.93) | 1.2 | 0.094 (0.053 to 0.135) | 0.006 (−0.022 to 0.034) |
| sqrtBM9 | | 0.46 | 0.34 | 0.86 (0.78 to 0.93) | 0.81 (0.75 to 0.92) | 1.1 | 0.091 (0.051 to 0.132) | 0.005 (−0.022 to 0.031) |
| Biomarker10 | CD91 on intermediate monocytes | 0.44 | 0.33 | 0.84 (0.76 to 0.92) | 0.8 (0.73 to 0.91) | −2.2 | 0.072 (0.04 to 0.104) | −0.001 (−0.021 to 0.02) |
| lnBM10 | | 0.44 | 0.33 | 0.84 (0.76 to 0.92) | 0.8 (0.72 to 0.92) | −1.8 | 0.073 (0.041 to 0.104) | 0 (−0.021 to 0.021) |
| sqrtBM10 | | 0.44 | 0.34 | 0.84 (0.76 to 0.92) | 0.8 (0.73 to 0.91) | −2 | 0.072 (0.04 to 0.104) | 0 (−0.021 to 0.021) |
| Biomarker11 | % of lymphocytes in whole leukocytes | 0.46 | 0.36 | 0.86 (0.79 to 0.93) | 0.82 (0.76 to 0.92) | 6.1 | 0.049 (0.022 to 0.075) | 0.015 (0.001 to 0.029) |
| lnBM11 | | 0.46 | 0.35 | 0.86 (0.79 to 0.93) | 0.83 (0.76 to 0.92) | 6.2 | 0.049 (0.023 to 0.074) | 0.015 (0.001 to 0.03) |

TABLE 3.2-continued

| | | Phase III: Model 2 biomarker performance. | | | | | | |
|---|---|---|---|---|---|---|---|---|
| Biomarkers | Descriptives | Goodness of fit (original)[a] | Goodness of fit (corrected) | AUC.orig (95% CI) | AUC.corrected (95% CI) | Brier. Improvement | IDI.events (95% CI) | IDI.nonevents (95% CI) |
| sqrtBM11 | | 0.46 | 0.37 | 0.86 (0.79 to 0.93) | 0.83 (0.76 to 0.91) | 6.3 | 0.049 (0.023 to 0.075) | 0.015 (0.001 to 0.03) |
| Biomarker12 | % of classical monocytes in total monocytes | 0.47 | 0.36 | 0.86 (0.78 to 0.94) | 0.82 (0.75 to 0.92) | 2.9 | 0.09 (0.048 to 0.132) | 0.011 (−0.015 to 0.035) |
| lnBM12 | | 0.47 | 0.36 | 0.85 (0.77 to 0.93) | 0.82 (0.74 to 0.93) | 3 | 0.088 (0.049 to 0.128) | 0.01 (−0.016 to 0.035) |
| sqrtBM12 | | 0.47 | 0.35 | 0.86 (0.78 to 0.94) | 0.82 (0.74 to 0.92) | 3.4 | 0.089 (0.048 to 0.13) | 0.01 (−0.015 to 0.035) |

Psy is Neuropsych.SimpleClassification.
[a]A Hosmer-Lemeshow goodness of fit was used to test calibration of the model.
Ln is natural logarithm of the biomarker and sqrt is square root of the biomarker.
Underscores are best performance biomarkers.
Baseline2 is the baseline of Phase III: Model 2.
New2 is a proposed panel of biomarkers for Phase III: Model 2. Only one leukocyte biomarker, i.e. lnBM8 can be added into baseline due to the limited size of the model.

TABLE 3.3

| | | Phase III: Model 3 biomarker performance. | | | | | | |
|---|---|---|---|---|---|---|---|---|
| Biomarkers | Descriptives | Goodness of fit (original)[a] | Goodness of fit (corrected) | AUC.orig (95% CI) | AUC.corrected (95% CI) | Brier. improvement | IDI.events (95% CI) | IDI.nonevents (95% CI) |
| Baseline3 | Demographics (Age, Sex, Ed, Psy) | 0.67 | 0.64 | 0.91 (0.86 to 0.96) | 0.9 (0.85 to 0.95) | NA | NA | NA |
| Biomarker1 | CD11c on NK cells | 0.67 | 0.63 | 0.91 (0.87 to 0.96) | 0.9 (0.85 to 0.95) | −3.5 | 0.019 (0.01 to 0.029) | −0.023 (−0.033 to −0.013) |
| lnBM1 | | 0.67 | 0.63 | 0.91 (0.87 to 0.96) | 0.9 (0.84 to 0.96) | −5.1 | 0.019 (0.01 to 0.029) | −0.023 (−0.033 to −0.014) |
| sqrtBM1 | | 0.67 | 0.64 | 0.91 (0.87 to 0.96) | 0.9 (0.85 to 0.95) | −8 | 0.019 (0.01 to 0.029) | −0.023 (−0.033 to −0.013) |
| Biomarker2 | CD11c on non-classical monocytes | 0.67 | 0.63 | 0.91 (0.87 to 0.96) | 0.9 (0.85 to 0.95) | −5.8 | 0.022 (0.009 to 0.034) | −0.021 (−0.033 to −0.01) |
| lnBM2 | | 0.67 | 0.64 | 0.91 (0.87 to 0.96) | 0.9 (0.85 to 0.95) | −8.4 | 0.021 (0.009 to 0.033) | −0.022 (−0.033 to −0.01) |
| sqrtBM2 | | 0.67 | 0.64 | 0.91 (0.87 to 0.96) | 0.9 (0.85 to 0.96) | −4.4 | 0.022 (0.009 to 0.034) | −0.021 (−0.033 to −0.01) |
| Biomarker3 | CD11c on neutrophils | 0.67 | 0.64 | 0.92 (0.87 to 0.96) | 0.9 (0.85 to 0.95) | −4.4 | 0.022 (0.009 to 0.034) | −0.021 (−0.034 to −0.008) |
| lnBM3 | | 0.67 | 0.63 | 0.92 (0.87 to 0.96) | 0.9 (0.86 to 0.96) | −5.5 | 0.021 (0.009 to 0.033) | −0.022 (−0.034 to −0.009) |
| sqrtBM3 | | 0.67 | 0.64 | 0.92 (0.87 to 0.96) | 0.9 (0.85 to 0.95) | −5.1 | 0.021 (0.009 to 0.034) | −0.021 (−0.034 to −0.009) |
| Biomarker4 | CD59 on T&B lymphocytes | 0.78 | 0.75 | 0.96 (0.93 to 0.99) | 0.95 (0.92 to 0.99) | 22 | 0.035 (0.003 to 0.067) | 0.024 (0.007 to 0.041) |
| lnBM4 | | 0.78 | 0.74 | 0.96 (0.92 to 0.99) | 0.95 (0.91 to 0.98) | 18.5 | 0.031 (0.003 to 0.059) | 0.02 (0.002 to 0.038) |
| sqrtBM4 | | 0.78 | 0.75 | 0.96 (0.92 to 0.99) | 0.95 (0.91 to 0.98) | 19.9 | 0.033 (0.003 to 0.063) | 0.022 (0.004 to 0.04) |
| Biomarker5 | CD59 on non-classical monocytes | 0.76 | 0.72 | 0.95 (0.91 to 0.99) | 0.94 (0.9 to 0.98) | 15.6 | 0.021 (0.005 to 0.038) | 0.011 (−0.004 to 0.027) |
| lnBM5 | | 0.76 | 0.73 | 0.95 (0.91 to 0.98) | 0.94 (0.9 to 0.98) | 15.7 | 0.021 (0.005 to 0.038) | 0.011 (−0.005 to 0.027) |
| sqrtBM5 | | 0.76 | 0.73 | 0.95 (0.91 to 0.98) | 0.94 (0.9 to 0.98) | 15.8 | 0.021 (0.005 to 0.038) | 0.011 (−0.004 to 0.027) |
| Biomarker6 | CD59 on neutrophils | 0.77 | 0.73 | 0.95 (0.91 to 0.99) | 0.94 (0.91 to 0.98) | 16.3 | 0.025 (0.006 to 0.044) | 0.014 (−0.003 to 0.032) |
| lnBM6 | | 0.76 | 0.73 | 0.95 (0.91 to 0.99) | 0.94 (0.89 to 0.98) | 14.4 | 0.022 (0.006 to 0.038) | 0.012 (−0.005 to 0.029) |
| sqrtBM6 | | 0.76 | 0.73 | 0.95 (0.91 to 0.99) | 0.94 (0.9 to 0.98) | 17.9 | 0.023 (0.006 to 0.041) | 0.013 (−0.004 to 0.03) |
| Biomarker7 | CD163 on classical monocytes | 0.77 | 0.73 | 0.95 (0.92 to 0.99) | 0.94 (0.9 to 0.98) | 18 | 0.027 (0.005 to 0.048) | 0.016 (−0.002 to 0.034) |

TABLE 3.3-continued

Phase III: Model 3 biomarker performance.

| Biomarkers | Descriptives | Goodness of fit (original)[a] | Goodness of fit (corrected) | AUC.orig (95% CI) | AUC.corrected (95% CI) | Brier. improvement | IDI.events (95% CI) | IDI.nonevents (95% CI) |
|---|---|---|---|---|---|---|---|---|
| lnBM7 | | 0.77 | 0.74 | 0.95 (0.92 to 0.99) | 0.94 (0.9 to 0.98) | 18.1 | 0.024 (0.004 to 0.044) | 0.014 (−0.001 to 0.028) |
| sqrtBM7 | | 0.77 | 0.74 | 0.95 (0.92 to 0.99) | 0.94 (0.9 to 0.98) | 19.6 | 0.026 (0.005 to 0.046) | 0.015 (−0.001 to 0.031) |
| Biomarker8 | CD163 on neutrophils | 0.80 | 0.75 | 0.96 (0.93 to 0.99) | 0.95 (0.92 to 0.99) | 22.5 | 0.045 (0.011 to 0.079) | 0.032 (0.006 to 0.058) |
| lnBM8 | | 0.80 | 0.76 | 0.96 (0.93 to 0.99) | 0.95 (0.92 to 0.99) | 24.4 | 0.049 (0.013 to 0.085) | 0.035 (0.009 to 0.062) |
| sqrtBM8 | | 0.80 | 0.76 | 0.96 (0.93 to 0.99) | 0.95 (0.92 to 0.99) | 23.3 | 0.047 (0.012 to 0.082) | 0.034 (0.008 to 0.06) |
| Biomarker9 | CD91 on NK cells | 0.75 | 0.71 | 0.95 (0.9 to 0.99) | 0.93 (0.89 to 0.98) | 9.1 | 0.034 (0.011 to 0.057) | −0.005 (−0.032 to 0.022) |
| lnBM9 | | 0.75 | 0.71 | 0.95 (0.9 to 0.99) | 0.94 (0.88 to 0.98) | 8.8 | 0.035 (0.01 to 0.059) | −0.004 (−0.031 to 0.023) |
| sqrtBM9 | | 0.75 | 0.71 | 0.95 (0.9 to 0.99) | 0.93 (0.88 to 0.98) | 9 | 0.034 (0.011 to 0.058) | −0.004 (−0.031 to 0.023) |
| Biomarker10 | CD91 on intermediate monocytes | 0.76 | 0.70 | 0.95 (0.9 to 0.99) | 0.93 (0.88 to 0.98) | 10.4 | 0.035 (0.009 to 0.06) | −0.003 (−0.028 to 0.022) |
| lnBM10 | | 0.75 | 0.71 | 0.95 (0.9 to 0.99) | 0.93 (0.89 to 0.99) | 10 | 0.033 (0.009 to 0.057) | −0.004 (−0.029 to 0.02) |
| sqrtBM10 | | 0.75 | 0.71 | 0.95 (0.9 to 0.99) | 0.93 (0.88 to 0.98) | 10.4 | 0.034 (0.009 to 0.059) | −0.004 (−0.028 to 0.021) |
| Biomarker11 | % of lymphocytes in whole leukocyls | 0.76 | 0.74 | 0.95 (0.91 to 0.99) | 0.94 (0.9 to 0.98) | 17.8 | 0.025 (0.009 to 0.041) | 0.015 (−0.003 to 0.032) |
| lnBM11 | | 0.76 | 0.73 | 0.95 (0.91 to 0.99) | 0.94 (0.9 to 0.98) | 19.5 | 0.024 (0.008 to 0.04) | 0.014 (−0.003 to 0.03) |
| sqrtBM11 | | 0.76 | 0.73 | 0.95 (0.91 to 0.99) | 0.94 (0.9 to 0.98) | 19.5 | 0.025 (0.009 to 0.04) | 0.014 (−0.003 to 0.031) |
| Biomarker12 | % of classical monocytes in total monocytes | 0.77 | 0.72 | 0.95 (0.91 to 0.99) | 0.94 (0.9 to 0.99) | 13.1 | 0.04 (0.015 to 0.065) | 0.003 (−0.032 to 0.039) |
| lnBM12 | | 0.77 | 0.73 | 0.95 (0.92 to 0.99) | 0.94 (0.9 to 0.98) | 15.3 | 0.041 (0.015 to 0.067) | 0.005 (−0.032 to 0.041) |
| sqrtBM12 | | 0.77 | 0.73 | 0.95 (0.91 to 0.99) | 0.94 (0.9 to 0.98) | 14.1 | 0.041 (0.015 to 0.066) | 0.004 (−0.032 to 0.04) |
| New3 | Age, Sex, Ed, Psy, lnBM8, sqrtBM4, sqrtBM11 | 0.82 | 0.77 | 0.97 (0.94 to 1) | 0.96 (0.93 to 0.99) | 28.7 | 0.065 (0.018 to 0.112) | 0.049 (0.024 to 0.075) |

Psy is Neuropsych.SimpleClassification.
[a]A Hosmer-Lemeshow goodness of fit was used to test calibration of the model.
Ln is natural logarithm of the biomarker and sqrt is square root of the biomarker.
Underscores are best performance biomarkers.
Baseline3 is the baseline of Phase III: Model 3.
New3 is a proposed panel of biomarkers for Phase III: Model 3.

TABLE 3.4

Phase III: Model 4 biomarker performance.

| Biomarkers | Descriptives | Goodness of fit (original) | Goodness of fit (corrected) | AUC.orig (95% CI) | AUC.corrected (95% CI) | Brier improvement | IDI.events (95% CI) | IDI.nonevents (95% CI) |
|---|---|---|---|---|---|---|---|---|
| Base model4 | Demographics (Age, Sex, Ed, Apoe) | 0.43 | 0.28 | 0.86 (0.79 to 0.93) | 0.81 (0.76 to 0.92) | NA | NA | NA |
| Biomarker1 | MFI of CD11c on NK | 0.43 | 0.26 | 0.85 (0.76 to 0.94) | 0.8 (0.72 to 0.93) | −5.6 | 0.05 (0.03 to 0.07) | −0.02 (−0.03 to −0.01) |
| lnBM1 | | 0.43 | 0.25 | 0.85 (0.76 to 0.92) | 0.79 (0.71 to 0.91) | −5.7 | 0.05 (0.03 to 0.07) | −0.02 (−0.03 to −0.01) |
| sqrtBM1 | | 0.43 | 0.25 | 0.86 (0.77 to 0.92) | 0.79 (0.71 to 0.91) | −5.6 | 0.05 (0.03 to 0.07) | −0.02 (−0.03 to −0.01) |
| Biomarker2 | MFI of CD11c on CD14⁻CD16⁺ Mono | 0.46 | 0.26 | 0.87 (0.78 to 0.95) | 0.8 (0.75 to 0.93) | −1.4 | 0.07 (0 to 0.11) | −0.01 (−0.03 to 0) |
| lnBM2 | | 0.46 | 0.26 | 0.86 (0.77 to 0.94) | 0.8 (0.74 to 0.93) | −1.3 | 0.06 (0.02 to 0.1) | −0.01 (−0.03 to 0) |

TABLE 3.4-continued

Phase III: Model 4 biomarker performance.

| Biomarkers | Descriptives | Goodness of fit (original) | Goodness of fit (corrected) | AUC.orig (95% CI) | AUC.corrected (95% CI) | Brier improvement | IDI.events (95% CI) | IDI.nonevents (95% CI) |
|---|---|---|---|---|---|---|---|---|
| sqrtBM2 | | 0.46 | 0.26 | 0.87 (0.77 to 0.93) | 0.8 (0.73 to 0.96) | −1.1 | 0.06 (0.01 to 0.1) | −0.01 (−0.03 to 0) |
| Biomarker3 | MFI of CD11c on CD14⁻ Neu | 0.45 | 0.27 | 0.86 (0.77 to 0.93) | 0.8 (0.73 to 0.92) | −2.7 | 0.06 (0.02 to 0.09) | −0.02 (−0.03 to 0) |
| lnBM3 | | 0.45 | 0.25 | 0.86 (0.77 to 0.93) | 0.79 (0.73 to 0.93) | −2.9 | 0.05 (0.02 to 0.09) | −0.02 (−0.03 to 0) |
| sqrtBM3 | | 0.45 | 0.25 | 0.86 (0.78 to 0.93) | 0.79 (0.75 to 0.92) | −2.8 | 0.05 (0.02 to 0.09) | −0.02 (−0.03 to 0) |
| Biomarker4 | MFI of CD59 on T&B | 0.56 | 0.42 | 0.9 (0.83 to 0.96) | 0.86 (0.79 to 0.96) | 18.8 | 0.07 (0.02 to 0.12) | 0.01 (−0.01 to 0.03) |
| lnBM4 | | 0.56 | 0.40 | 0.91 (0.82 to 0.96) | 0.86 (0.8 to 0.97) | 18.5 | 0.07 (0.03 to 0.12) | 0.01 (−0.01 to 0.03) |
| sqrtBM4 | | 0.56 | 0.41 | 0.91 (0.82 to 0.97) | 0.86 (0.81 to 0.96) | 18.6 | 0.07 (0.02 to 0.12) | 0.01 (−0.01 to 0.03) |
| Biomarker5 | MFI of CD59 on CD14⁻CD16⁺ Mono | 0.56 | 0.40 | 0.91 (0.82 to 0.97) | 0.85 (0.8 to 0.96) | 19.2 | 0.07 (0.03 to 0.12) | 0.01 (−0.01 to 0.03) |
| lnBM5 | | 0.56 | 0.40 | 0.91 (0.82 to 0.96) | 0.85 (0.79 to 0.97) | 18.9 | 0.07 (0.03 to 0.12) | 0.01 (−0.01 to 0.03) |
| sqrtBM5 | | 0.56 | 0.40 | 0.91 (0.83 to 0.97) | 0.85 (0.78 to 0.98) | 19.1 | 0.07 (0.03 to 0.12) | 0.01 (−0.01 to 0.03) |
| Biomarker6 | MFI of CD59 on CD14⁻CD16⁺ Neu | 0.56 | 0.42 | 0.91 (0.82 to 0.97) | 0.86 (0.79 to 0.96) | 20.5 | 0.08 (0.03 to 0.12) | 0.01 (−0.01 to 0.03) |
| lnBM6 | | 0.56 | 0.40 | 0.91 (0.83 to 0.96) | 0.85 (0.8 to 0.97) | 19.6 | 0.07 (0.03 to 0.12) | 0.01 (−0.01 to 0.03) |
| sqrtBM6 | | 0.56 | 0.40 | 0.91 (0.84 to 0.97) | 0.85 (0.82 to 0.96) | 20 | 0.07 (0.03 to 0.12) | 0.01 (0 to 0.03) |
| Biomarker7 | MFI of CD163 on CD14⁺CD16⁻ Mono | 0.57 | 0.43 | 0.91 (0.83 to 0.96) | 0.86 (0.79 to 0.97) | 20.1 | 0.08 (0.03 to 0.14) | 0.01 (−0.01 to 0.03) |
| lnBM7 | | 0.57 | 0.43 | 0.91 (0.83 to 0.96) | 0.86 (0.82 to 0.96) | 19.4 | 0.07 (0.02 to 0.13) | 0.01 (−0.01 to 0.03) |
| sqrtBM7 | | 0.57 | 0.43 | 0.91 (0.83 to 0.96) | 0.86 (0.81 to 0.96) | 19.7 | 0.08 (0.02 to 0.15) | 0.01 (−0.01 to 0.03) |
| Biomarker8 | MFI of CD163 on CD14⁻ Neu | 0.63 | 0.49 | 0.93 (0.87 to 0.97) | 0.88 (0.86 to 0.97) | 28.3 | 0.12 (0.04 to 0.2) | 0.03 (0 to 0.06) |
| lnBM8 | | 0.64 | 0.51 | 0.94 (0.86 to 0.98) | 0.89 (0.82 to 0.97) | 29.8 | 0.13 (0.05 to 0.2) | 0.03 (0 to 0.06) |
| sqrtBM8 | | 0.63 | 0.50 | 0.93 (0.85 to 0.98) | 0.89 (0.86 to 0.98) | 29.1 | 0.13 (0.04 to 0.21) | 0.03 (0 to 0.06) |
| Biomarker9 | MFI of CD91 on NK | 0.59 | 0.41 | 0.91 (0.82 to 0.97) | 0.85 (0.8 to 0.96) | 13.4 | 0.1 (0.03 to 0.16) | 0 (−0.03 to 0.04) |
| lnBM9 | | 0.59 | 0.40 | 0.91 (0.82 to 0.97) | 0.85 (0.76 to 0.97) | 13.3 | 0.1 (0.03 to 0.17) | 0 (−0.04 to 0.04) |
| sqrtBM9 | | 0.59 | 0.40 | 0.92 (0.82 to 0.98) | 0.85 (0.81 to 0.97) | 13.4 | 0.1 (0.03 to 0.16) | 0 (−0.03 to 0.04) |
| Biomarker10 | MFI of CD91 on CD14⁺CD16⁺ Mono | 0.57 | 0.38 | 0.92 (0.82 to 0.98) | 0.85 (0.72 to 0.96) | 13.4 | 0.09 (0.04 to 0.15) | 0 (−0.03 to 0.03) |
| lnBM10 | | 0.58 | 0.40 | 0.92 (0.84 to 0.98) | 0.86 (0.8 to 0.95) | 13.1 | 0.09 (0.04 to 0.14) | 0 (−0.04 to 0.04) |
| sqrtBM10 | | 0.57 | 0.40 | 0.92 (0.83 to 0.97) | 0.86 (0.74 to 0.95) | 13.3 | 0.09 (0.04 to 0.15) | 0 (−0.04 to 0.03) |
| Biomarker11 | Absolute % Lym | 0.59 | 0.45 | 0.92 (0.85 to 0.98) | 0.88 (0.83 to 0.97) | 28.1 | 0.11 (0.07 to 0.16) | 0.02 (0 to 0.05) |
| lnBM11 | | 0.58 | 0.44 | 0.92 (0.84 to 0.97) | 0.88 (0.82 to 0.98) | 26.4 | 0.1 (0.06 to 0.14) | 0.02 (0 to 0.05) |
| sqrtBM11 | | 0.58 | 0.46 | 0.92 (0.84 to 0.97) | 0.88 (0.84 to 0.97) | 27.3 | 0.1 (0.06 to 0.14) | 0.02 (0 to 0.05) |
| Biomarker12 | Relative % CD14⁺CD16⁻ Mono | 0.61 | 0.43 | 0.92 (0.85 to 0.98) | 0.87 (0.81 to 0.96) | 20 | 0.12 (0.06 to 0.18) | 0.01 (−0.03 to 0.05) |
| lnBM12 | | 0.61 | 0.44 | 0.93 (0.86 to 0.98) | 0.87 (0.77 to 0.98) | 20.3 | 0.12 (0.06 to 0.18) | 0.01 (−0.03 to 0.05) |
| sqrtBM12 | | 0.61 | 0.44 | 0.93 (0.85 to 0.99) | 0.87 (0.79 to 0.97) | 20.2 | 0.12 (0.06 to 0.18) | 0.01 (−0.03 to 0.05) |
| New4 | Age, Sex, Ed, Apoe, lnBM8 | 0.64 | 0.51 | 0.94 (0.86 to 0.98) | 0.89 (0.82 to 0.97) | 29.8 | 0.13 (0.05 to 0.2) | 0.03 (0 to 0.06) |

Model 4 only included cognitively normal subjects alongside their PET Aβ status to stratify study cohort into healthy controls (CN & <25CL), and preclinical (CN & >25CL). Base model 4 is the baseline of Stage III: Model 4, which has age, sex, years of education and genotype of ApoE. Model 4 has 30 cases. In order to prove the concept, one biomarker, MFI of CD163 on CD14⁻ neutrophils (lnBM8), is added to Base model 4 to compose New 4. In the paired-sample design ROC analysis by using SPSS (DeLong test), AUC is improved from Base model 4: 0.87 (CI: 0.81 to 0.96) to New 4: 0.94 (CI: 0.86 to 0.98) with P value of 0.063.

TABLE 3.5

Phase IV: Validation cohort.

| Biomarkers | Descriptives | Goodness of fit (original) | Goodness of fit (corrected) | AUC.orig (95% CI) | AUC.corrected (95% CI) | Brier improvement | IDI.events (95% CI) | IDI.nonevents (95% CI) |
|---|---|---|---|---|---|---|---|---|
| Base model | Demographics (Age, Sex, Ed, ApoE) | 0.40 | 0.25 | 0.81 (CI: 0.72 to 0.9) | 0.74 (CI: 0.26 to 0.84) | NA | NA | NA |
| BM1 | MFI of CD11c in lym | 0.49 | 0.30 | 0.85 (CI: 0.72 to 0.95) | 0.78 (CI: 0.37 to 0.87) | 9.9 | 0.05 (CI: 0.02 to 0.08) | 0 (CI: −0.02 to 0.03) |
| BM2 | MFI of CD11c in CD14⁻ mono | 0.49 | 0.33 | 0.84 (CI: 0.71 to 0.94) | 0.78 (CI: 0.33 to 0.87) | 13.3 | 0.06 (CI: 0.02 to 0.09) | 0 (CI: −0.02 to 0.03) |
| BM3 | MFI of CD59 in CD14⁺ mono | 0.48 | 0.29 | 0.87 (CI: 0.74 to 0.96) | 0.79 (CI: 0.31 to 0.87) | 7.7 | 0.07 (CI: −0.01 to 0.13) | 0.02 (CI: −0.03 to 0.07) |
| BM4 | MFI of CD59 in CD14⁻ mono | 0.45 | 0.23 | 0.85 (CI: 0.73 to 0.93) | 0.77 (CI: 0.43 to 0.88) | 7.5 | 0.01 (CI: −0.04 to 0.06) | 0.03 (CI: −0.01 to 0.06) |
| BM5 | MFI of CD91 in CD14⁺CD59$^{dim}$ mono | 0.44 | 0.23 | 0.83 (CI: 0.7 to 0.93) | 0.75 (CI: 0.34 to 0.87) | 3.2 | 0 (CI: −0.03 to 0.03) | 0.01 (CI: 0.01 to 0.02) |
| BM6 | MFI of CD91 in neutro | 0.43 | 0.23 | 0.82 (CI: 0.69 to 0.94) | 0.74 (CI: 0.39 to 0.89) | 4.6 | 0 (CI: −0.02 to 0.01) | 0.01 (CI: 0.01 to 0.02) |
| BM7 | MFI of CD163 in lym | 0.44 | 0.22 | 0.83 (CI: 0.7 to 0.93) | 0.74 (CI: 0.33 to 0.86) | 4.2 | 0.02 (CI: 0 to 0.04) | 0 (CI: −0.02 to 0.02) |
| BM8 | MFI of CD163 in CD14⁻ neutro | 0.43 | 0.21 | 0.83 (CI: 0.68 to 0.94) | 0.73 (CI: 0.21 to 0.82) | 4.5 | 0.02 (CI: −0.01 to 0.04) | 0.01 (CI: −0.01 to 0.03) |
| V1 | Age, Sex, Ed, ApoE, BM2, BM3 | 0.58 | 0.37 | 0.9 (CI: 0.78 to 0.98) | 0.83 (CI: 0.5 to 0.92) | 22.6 | 0.13 (CI: 0.06 to 0.2) | 0.03 (CI: −0.04 to 0.09) |
| V2 | Age, Sex, Ed, ApoE, BM3, BM6 | 0.59 | 0.38 | 0.91 (CI: 0.81 to 0.99) | 0.84 (CI: 0.51 to 0.88) | 25.1 | 0.11 (CI: 0.01 to 0.21) | 0.06 (CI: 0.02 to 0.11) |
| V3 | Age, Sex, Ed, ApoE, BM2, BM3, BM6 | 0.68 | 0.45 | 0.95 (CI: 0.86 to 1) | 0.86 (CI: 0.6 to 0.96) | 39.8 | 0.18 (CI: 0.11 to 0.26) | 0.07 (CI: 0.01 to 0.14) |

Here in validation cohort we defined disease state simply by centiloids >25CL for an "overall" assessment. Base model is the baseline of Stage III: Validation cohort, which has age, sex, years of education and genotype of ApoE. Validation cohort has 49 cases. A pair of biomarkers, MFI of CD11c in CD14⁻ monocytes (BM2) and MFI of CD59 in CD14⁺ monocytes (BM3), are added to the Base model to compose Validation composite 1 (V1). In the paired-sample design ROC analysis by using SPSS (DeLong test), AUC is improved by 5.2% from the Base model: 0.81 (CI: 0.69 to 0.89) to V1: 0.85 (CI: 0.74 to 0.91) with P value of 0.112. The other performed pair, BM3 and MFI of CD91 in neutrophils (BM6), are added to the Base model to compose V2, which improves AUC by 7% from the Base model: 0.8 (CI: 0.68 to 0.88) to V2: 0.85 (CI: 0.74 to 0.92) with P value of 0.072. Further, if adds three performed biomarkers, BM2, BM3, and BM6 to the baseline, this V3 significantly improves AUC by 7.1% from the Base model: 0.82 (CI: 0.70 to 0.89) to V2: 0.88 (CI: 0.77 to 0.94) with P value of 0.05. However, this model of V3 is overfitted due to not enough cases have been included.

40

TABLE A.6.1

Phase III Model 1 biomarker skewness and normality statistics

| Descriptives | Skewness | Std. Error | Kolmogorov-Smirnova$^a$ (Sig) | Shapiro-Wilk (Sig.) |
|---|---|---|---|---|
| Baseline3.1 | 0.118 | 0.224 | 0.000 | 0.000 |
| Biomarker1 | −0.784 | 0.224 | 0.048 | 0.001 |
| InBM1 | −0.179 | 0.224 | .200* | 0.647 |
| sqrtBM1 | 0.288 | 0.224 | .200* | 0.426 |
| Biomarker2 | −1.096 | 0.224 | 0.039 | 0.000 |
| InBM2 | −0.327 | 0.224 | .200* | 0.422 |
| sqrtBM2 | 0.381 | 0.224 | .200* | 0.307 |
| Biomarker3 | −1.323 | 0.224 | 0.000 | 0.000 |
| InBM3 | 0.452 | 0.224 | 0.154 | 0.100 |
| sqrtBM3 | 0.880 | 0.224 | 0.002 | 0.000 |
| Biomarker4 | 1.385 | 0.224 | 0.000 | 0.000 |
| InBM4 | 0.740 | 0.224 | 0.000 | 0.000 |
| sqrtBM4 | 1.056 | 0.224 | 0.000 | 0.000 |
| Biomarker5 | 1.293 | 0.224 | 0.000 | 0.000 |
| InBM5 | 0.323 | 0.224 | 0.015 | 0.046 |
| sqrtBM5 | 0.825 | 0.224 | 0.000 | 0.000 |
| Biomarker6 | 1.079 | 0.224 | 0.000 | 0.000 |
| InBM6 | 0.553 | 0.224 | 0.000 | 0.001 |
| sqrtBM6 | 0.808 | 0.224 | 0.000 | 0.000 |
| Biomarker7 | 0.322 | 0.224 | .200* | 0.499 |
| InBM7 | −2.041 | 0.224 | 0.000 | 0.000 |
| sqrtBM7 | −0.987 | 0.224 | 0.020 | 0.000 |
| Biomarker8 | −0.392 | 0.224 | .200* | 0.107 |

TABLE A.6.1-continued

Phase III Model 1 biomarker skewness and normality statistics

| Descriptives | Skewness | Std. Error | Kolmogorov-Smirnova$^a$ (Sig) | Shapiro-Wilk (Sig.) |
|---|---|---|---|---|
| InBM8 | −0.080 | 0.224 | .200* | 0.665 |
| sqrtBM8 | 0.155 | 0.224 | .200* | 0.533 |
| Biomarker9 | 1.922 | 0.224 | 0.000 | 0.000 |
| InBM9 | 0.715 | 0.224 | 0.001 | 0.000 |
| sqrtBM9 | 1.308 | 0.224 | 0.000 | 0.000 |
| Biomarker10 | 1.064 | 0.224 | 0.000 | 0.000 |
| InBM10 | 0.257 | 0.224 | 0.018 | 0.046 |
| sqrtBM10 | 0.656 | 0.224 | 0.000 | 0.000 |
| Biomarker11 | −1.037 | 0.224 | 0.036 | 0.000 |
| InBM11 | 0.005 | 0.224 | .200* | 0.267 |
| sqrtBM11 | 0.492 | 0.224 | .200* | 0.023 |
| Biomarker12 | −0.976 | 0.224 | 0.000 | 0.000 |
| InBM12 | −3.034 | 0.224 | 0.000 | 0.000 |
| sqrtBM12 | −1.895 | 0.224 | 0.000 | 0.000 |

$^a$Lilliefors Significance Correction.

*This is a lower bound of the true significance.

TABLE A.6.2

Phase III Model 2 biomarker skewness and normality statistics

| Descriptives | Skewness | Std. Error | Kolmogorov-Smirnova (Sig.) | Shapiro-Wilk (Sig.) |
|---|---|---|---|---|
| Baseline3.2 | 0.574 | 0.224 | 0.094 | 0.000 |
| Biomarker1 | −0.784 | 0.224 | 0.048 | 0.001 |
| InBM1 | −0.184 | 0.224 | .200* | 0.638 |
| sqrtBM1 | 0.288 | 0.224 | .200* | 0.433 |
| Biomarker2 | −1.096 | 0.224 | 0.039 | 0.000 |
| InBM2 | −0.333 | 0.224 | .200* | 0.408 |
| sqrtBM2 | 0.380 | 0.224 | .200* | 0.310 |
| Biomarker3 | −1.323 | 0.224 | 0.000 | 0.000 |
| InBM3 | 0.449 | 0.224 | 0.083 | 0.102 |
| sqrtBM3 | 0.882 | 0.224 | 0.002 | 0.000 |
| Biomarker4 | 1.385 | 0.224 | 0.000 | 0.000 |
| InBM4 | 0.739 | 0.224 | 0.000 | 0.000 |
| sqrtBM4 | 1.056 | 0.224 | 0.000 | 0.000 |
| Biomarker5 | 1.293 | 0.224 | 0.000 | 0.000 |
| InBM5 | 0.327 | 0.224 | 0.014 | 0.044 |
| sqrtBM5 | 0.825 | 0.224 | 0.000 | 0.000 |
| Biomarker6 | 1.079 | 0.224 | 0.000 | 0.000 |
| InBM6 | 0.548 | 0.224 | 0.000 | 0.001 |
| sqrtBM6 | 0.810 | 0.224 | 0.000 | 0.000 |
| Biomarker7 | 0.322 | 0.224 | .200* | 0.499 |
| InBM7 | −2.041 | 0.224 | 0.000 | 0.000 |
| sqrtBM7 | −0.987 | 0.224 | 0.020 | 0.000 |
| Biomarker8 | −0.392 | 0.224 | .200* | 0.107 |
| InBM8 | −0.080 | 0.224 | .200* | 0.665 |
| sqrtBM8 | 0.155 | 0.224 | .200* | 0.533 |
| Biomarker9 | 1.922 | 0.224 | 0.000 | 0.000 |
| InBM9 | 0.711 | 0.224 | 0.001 | 0.000 |
| sqrtBM9 | 1.305 | 0.224 | 0.000 | 0.000 |
| Biomarker10 | 1.064 | 0.224 | 0.000 | 0.000 |
| InBM10 | 0.256 | 0.224 | 0.024 | 0.049 |
| sqrtBM10 | 0.657 | 0.224 | 0.000 | 0.000 |
| Biomarker11 | −1.037 | 0.224 | 0.036 | 0.000 |
| InBM11 | 0.004 | 0.224 | .200* | 0.268 |
| sqrtBM11 | 0.522 | 0.224 | .200* | 0.013 |
| Biomarker12 | −0.976 | 0.224 | 0.000 | 0.000 |
| InBM12 | −3.032 | 0.224 | 0.000 | 0.000 |
| sqrtBM12 | −1.899 | 0.224 | 0.000 | 0.000 |

[a]Lilliefors Significance Correction.
*This is a lower bound of the true significance.

TABLE A.6.3

Phase III Model 3 biomarker skewness and statistics

| Biomarkers | Skewness | Std. Error | Kolmogorov-Smirnova (Sig.) | Shapiro-Wilk (Sig.) |
|---|---|---|---|---|
| Baseline | 0.375 | 0.254 | 0.000 | 0.000 |
| Biomarker1 | −0.816 | 0.254 | .200* | 0.010 |
| InBM1 | −0.315 | 0.254 | .200* | 0.637 |
| sqrtBM1 | 0.261 | 0.254 | .200* | 0.833 |
| Biomarker2 | −0.658 | 0.254 | .200* | 0.052 |
| InBM2 | −0.585 | 0.254 | .200* | 0.111 |
| sqrtBM2 | 0.056 | 0.254 | .200* | 0.991 |
| Biomarker3 | −1.303 | 0.254 | 0.000 | 0.000 |
| InBM3 | 0.365 | 0.254 | 0.164 | 0.441 |
| sqrtBM3 | 0.833 | 0.254 | 0.004 | 0.003 |
| Biomarker4 | 1.608 | 0.254 | 0.000 | 0.000 |
| InBM4 | | | 0.000 | 0.000 |
| sqrtBM4 | 1.305 | 0.254 | 0.000 | 0.000 |
| Biomarker5 | 1.436 | 0.254 | 0.000 | 0.000 |
| InBM5 | 0.380 | 0.254 | 0.049 | 0.064 |
| sqrtBM5 | 0.926 | 0.254 | 0.001 | 0.001 |
| Biomarker6 | 1.283 | 0.254 | 0.000 | 0.000 |
| InBM6 | 0.665 | 0.254 | 0.001 | 0.004 |
| sqrtBM6 | 0.960 | 0.254 | 0.000 | 0.000 |
| Biomarker7 | 0.598 | 0.254 | 0.026 | 0.050 |
| InBM7 | −2.293 | 0.254 | 0.000 | 0.000 |
| sqrtBM7 | −1.285 | 0.254 | 0.000 | 0.000 |
| Biomarker8 | −0.309 | 0.254 | .200* | 0.174 |

TABLE A.6.3-continued

Phase III Model 3 biomarker skewness and statistics

| Biomarkers | Skewness | Std. Error | Kolmogorov-Smirnova (Sig.) | Shapiro-Wilk (Sig.) |
|---|---|---|---|---|
| InBM8 | −0.141 | 0.254 | .200* | 0.409 |
| sqrtBM8 | 0.082 | 0.254 | .200* | 0.444 |
| Biomarker9 | 1.904 | 0.254 | 0.000 | 0.000 |
| InBM9 | 0.506 | 0.254 | 0.003 | 0.013 |
| sqrtBM9 | 1.123 | 0.254 | 0.000 | 0.000 |
| Biomarker10 | 1.057 | 0.254 | 0.000 | 0.000 |
| InBM10 | 0.314 | 0.254 | 0.059 | 0.082 |
| sqrtBM10 | 0.694 | 0.254 | 0.000 | 0.001 |
| Biomarker11 | −0.963 | 0.254 | 0.043 | 0.001 |
| InBM11 | 0.039 | 0.254 | .200* | 0.759 |
| sqrtBM11 | 0.518 | 0.254 | 0.177 | 0.077 |
| Biomarker12 | −1.259 | 0.254 | 0.000 | 0.000 |
| InBM12 | −3.054 | 0.254 | 0.000 | 0.000 |
| sqrtBM12 | −2.118 | 0.254 | 0.000 | 0.000 |

[a]Lilliefors Significance Correction.
*This is a lower bound of the true significance.

TABLE A.7.1

Phase III variables entered/removed[a]

| Model | Variables Entered | Variables Removed | Method |
|---|---|---|---|
| 1 | Biomarker3, Biomarker2, Biomarker1[b] | | Enter |
| 2 | Biomarker5, Biomarker4, Biomarker6[b] | | Enter |
| 3 | Biomarker7, Biomarker8[b] | | Enter |
| 4 | Biomarker9, Biomarker10[b] | | Enter |
| 5 | Biomarker11, Biomarker12[b] | | Enter |

[a]Dependent Variable: Image.PET.Centiloid.
[b]All requested variables entered.

TABLE A.7.2

Phase III collinearity Statistics

| Biomarkers | Tolerance | VIF | Division of biomarkers |
|---|---|---|---|
| Biomarker1 | 0.60 | 1.68 | CD11c |
| Biomarker2 | 0.70 | 1.43 | CD11c |
| Biomarker3 | 0.58 | 1.73 | CD11c |
| Biomarker4 | 0.31 | 3.20 | CD59 |
| Biomarker5 | 0.47 | 2.14 | CD59 |
| Biomarker6 | 0.26 | 3.92 | CD59 |
| Biomarker7 | 0.80 | 1.25 | CD163 |
| Biomarker8 | 0.62 | 1.62 | CD163 |
| Biomarker9 | 0.70 | 1.43 | CD91 |
| Biomarker10 | 0.47 | 2.15 | CD91 |
| Biomarker11 | 0.86 | 1.17 | % Lym |
| Biomarker12 | 0.69 | 1.45 | % Mono |

In model 1 (Table 3.1), the baseline 1 discriminated between <25CL and >25CL with an AUC of 0.85 (0.79 to 0.91). The MFI of CD163 on neutrophils (InBM8) had the best improved AUC of 0.89 (0.84 to 0.94); Brier improvement of 16%; IDI with events of 0.06 (0.024 to 0.096) and without events of 0.041 (0.015 to 0.067). Two other performing biomarkers, MFI of CD59 on CD14−CD16+ monocytes (InBM5) and MFI of CD11c on total neutrophils (InBM3), were included to form a panel of biomarkers: New 1. New 1 had an AUC of 0.91 (0.86 to 0.95), Brier improvement 17.8%, IDI with and without events of 0.085 (0.049 to 0.12) and 0.050 (0.019 to 0.081), respectively. New 1 had sensitivity of 89.9% (95% Cl 80.2% to 95.8%), specificity of 76.9% (66.0% to 85.7%) and overall accuracy 83.0% at the Youden index cut-off point (Table A.8.1).

TABLE A.8.1

ROC metrics for new models in Phase III (in composite with base models).

| New panels[a] | Cut-off values | Value | Sensitivity % (95% CI) | Specificity % (95% CI) | Accuracy % | AUC % (95% CI) | PPV | NPV |
|---|---|---|---|---|---|---|---|---|
| New 1 | Cut-off 1 | ≥0.49 | 86.7 (75.4 to 94.1) | 85.7 (73.8 to 93.6) | 86.2 | 93 (88.7 to 97.3) | 0.867 | 0.857 |
| | Cut-off 2 | ≥0.20 | 95 (86.1 to 99) | 60.7 (46.8 to 73.5) | 78.5 | | 0.722 | 0.919 |
| New 2 | Cut-off 1 | ≥0.39 | 77.5 (61.6 to 89.2) | 88.9 (80 to 94.8) | 85.1 | 90.4 (84.6 to 96.2) | 0.775 | 0.889 |
| | Cut-off 2 | ≥0.11 | 95 (83.1 to 99.4) | 56.8 (45.3 to 67.8) | 69.4 | | 0.521 | 0.958 |
| New 3 | Cut-off 1 | ≥0.68 | 72.9 (55.9 to 83.1) | 93.2 (81.3 to 98.6) | 82.6 | 90.1 (84 to 96.1) | 0.921 | 0.759 |
| | Cut-off 2 | ≥0.16 | 95.8 (85.8 to 99.5) | 50 (34.6 to 65.4) | 73.9 | | 0.677 | 0.917 |
| New 4 | Cut-off 1 | ≥0.25 | 95.2 (76.2 to 99.9) | 83.3 (72.1 to 91.4) | 86.2 | 94.1 (86.3 to 98.8) | 0.645 | 0.982 |

[a]Best performed biomarkers adding into Base model to form panels. Cut-off 1: cut-off value at the Youden index. Cut-off 2: cut-off value at the 95% sensitivity. PPV and NPV: Positive and negative predictive values.
New 1: Added MFI of CD59 on T&B (BM4), MFI of CD163 on CD14⁻ neutrophils (BM8), MFI of CD91 on CD14⁺CD16⁺ monocytes (BM10) and MFI of CD11c on CD14⁻CD16⁺ monocytes (lnBM2) to the Base model; New 2: Added MFI of CD163 on CD14⁻ neutrophils (BM8) to the Base model; and New 3: Added MFI of CD59 on CD14⁻CD16⁺ monocytes (BM5), MFI of CD163 on CD14⁻ neutrophils (lnBM8), MFI of CD91 on CD14⁺CD16⁺ monocytes (BM10) and MFI of CD11c on CD14⁻CD16⁺ monocytes (sqrtBM2) to the Base model.

In model 2 (Table 3.2 above), the baseline 2 discriminated between <25CL and >25CL & <100CL with an AUC of 0.84 (0.77 to 0.91). The MFI of CD163 on neutrophils (lnBM8) had the best improved AUC of 0.90 (0.84 to 0.96); Brier improvement of 20%; IDI with events of 0.106 (0.050 to 0.162) and without events of 0.051 (0.024 to 0.077). Notably, model 2 only had 52 cases and only one biomarker was added so as to not overfit the model, to form New 2. New 2 had sensitivity of 90.0% (76.3% to 97.2%), specificity of 76.5% (65.8% to 85.3%) and overall accuracy of 81.0% at the Youden index cut-off point (Table A.8.1).

In model 3 (Table 3.3 above), the baseline 3 was over-exaggerated because all MCI subjects had been classified as cases. The MFI of CD163 on neutrophils (lnBM8) had the best improved AUC of 0.96 (0.93 to 0.99); Brier improvement of 24.4%; IDI with events of 0.049 (0.013 to 0.085) and without events of 0.035 (0.009 to 0.062). Two other performing biomarkers, MFI of CD59 on CD14–CD16–lymphocytes (sqrtBM4) and absolute percentage of CD14–lymphocyte in whole blood (sqrtBM11), were also included to form a panel of biomarkers: New3. New 3 improved the AUC from the baseline by 6%. New 3 had sensitivity of 91.2% (80.7% to 97.1%), specificity of 93.9% (85.2% to 98.3%) and overall accuracy of 92.7% at the Youden index cut-off point (Table A.8.1).

Overall, different biomarkers, composites or panels were proposed in different models. Whereas three candidate biomarkers: CD11c, CD59 and CD163 performed very well, CD163 was always had the best performance. Model cut-off values, sensitivity, specificity and accuracy for each biomarker can be found in Table A.8.2-4.

TABLE A.8.2

Phase III Model 1 Cut-off values for test biomarkers alone.

| Standalone test biomarkers[b] | Cut-off values | Value | Sensitivity % (95% CI) | Specificity % (95% CI) | Accuracy % | AUC % (95% CI) |
|---|---|---|---|---|---|---|
| BM1 | Cut-off 1 | ≤11.00 | 52.5 (39.1 to 65.7) | 75 (61.6 to 85.6) | 63.5 | 64.7 (53.4 to 73.7) |
| | Cut-off 2 | ≤20.30 | 96.6 (88.3 to 99.6) | 7.1 (2 to 17.3) | 53.0 | |
| BM2 | Cut-off 1 | ≤38.70 | 49.2 (35.9 to 62.5) | 85.7 (73.8 to 93.6) | 67.0 | 65.6 (54.3 to 74.6) |
| | Cut-off 2 | ≤93.50 | 94.9 (85.9 to 98.9) | 5.4 (1.1 to 14.9) | 51.3 | |
| BM3 | Cut-off 1 | ≤9.82 | 66.1 (52.6 to 77.9) | 71.4 (57.8 to 82.7) | 68.7 | 70.1 (59.1 to 78.5) |
| | Cut-off 2 | ≤14.70 | 94.9 (85.9 to 98.9) | 26.8 (15.8 to 40.3) | 61.7 | |
| BM4 | Cut-off 1 | ≥12.20 | 47.5 (34.3 to 60.9) | 91.1 (80.4 to 97) | 68.7 | 67.8 (56.3 to 76.7) |
| | Cut-off 2 | ≥5.84 | 94.9 (85.9 to 98.9) | 3.6 (0.4 to 12.3) | 50.4 | |
| BM5 | Cut-off 1 | ≥13.90 | 49.2 (35.9 to 62.5) | 91.1 (80.4 to 97) | 69.6 | 69.8 (58.8 to 78.3) |
| | Cut-off 2 | ≥8.45 | 94.9 (85.9 to 98.9) | 23.2 (13 to 36.4) | 60.0 | |
| BM6 | Cut-off 1 | ≥20.00 | 50.9 (37.5 to 64.1) | 87.5 (75.9 to 94.8) | 68.7 | 66 (54.5 to 75) |
| | Cut-off 2 | ≥12.20 | 94.9 (85.9 to 98.9) | 1.8 (0.1 to 9.6) | 49.6 | |
| BM7 | Cut-off 1 | ≤157.00 | 67.8 (54.4 to 79.4) | 71.4 (57.8 to 82.7) | 69.6 | 73.2 (62.2 to 81.3) |
| | Cut-off 2 | ≤207.00 | 94.9 (85.9 to 98.9) | 14.3 (6.4 to 26.2) | 55.7 | |
| BM8 | Cut-off 1 | ≤12.70 | 72.9 (59.7 to 83.6) | 69.6 (55.9 to 81.2) | 71.3 | 68.9 (57.7 to 77.6) |
| | Cut-off 2 | ≤16.10 | 94.9 (85.9 to 98.9) | 8.9 (3 to 19.6) | 53.0 | |
| BM9 | Cut-off 1 | ≥3.63 | 69.5 (56.1 to 80.8) | 62.5 (48.6 to 75.1) | 66.1 | 64.8 (53.5 to 73.9) |
| | Cut-off 2 | ≥2.43 | 94.9 (85.9 to 98.9) | 5.4 (1.1 to 14.9) | 51.3 | |

TABLE A.8.2-continued

Phase III Model 1 Cut-off values for test biomarkers alone.

| Standalone test biomarkers[b] | Cut-off values | Value | Sensitivity % (95% CI) | Specificity % (95% CI) | Accuracy % | AUC % (95% CI) |
|---|---|---|---|---|---|---|
| BM10 | Cut-off 1 | ≥241.00 | 50.9 (37.5 to 64.1) | 83.9 (71.7 to 92.4) | 67.0 | 65.1 (53.8 to 74.1) |
| | Cut-off 2 | ≥109.00 | 94.9 (85.9 to 98.9) | 12.5 (5.2 to 24.1) | 54.8 | |
| BM11 | Cut-off 1 | ≤0.27 | 69.5 (56.1 to 80.8) | 64.3 (50.4 to 76.6) | 67.0 | 64.5 (53.2 to 73.5) |
| | Cut-off 2 | ≤0.36 | 94.9 (85.9 to 98.9) | 10.7 (4 to 21.9) | 53.9 | |
| BM12 | Cut-off 1 | ≥0.61 | 71.2 (57.9 to 82.2) | 53.6 (39.7 to 67) | 62.6 | 65.9 (54.8 to 74.7) |
| | Cut-off 2 | ≥0.52 | 94.9 (85.9 to 98.9) | 23.2 (13 to 36.4) | 60.0 | |

[b]Test biomarkers alone without adding into baseline.
Cut-off 1: cut-off value at the Youden index.
Cut-off 2: cut-off value at the 95% sensitivity.

TABLE A.8.3

Phase III Model 2 Cut-off values for test biomarkers alone.

| Standalone test biomarker[b] | Cut-off values | Value | Sensitivity % (95% CI) | Specificity % (95% CI) | Accuracy % | AUC % (95% CI) |
|---|---|---|---|---|---|---|
| BM1 | Cut-off 1 | ≤10.90 | 47.2 (30.4 to 64.5) | 75 (61.6 to 85.6) | 64.1 | 63.1 (50.1 to 73.4) |
| | Cut-off 2 | ≤18.20 | 94.4 (81.3 to 99.3) | 17.9 (8.9 to 30.4) | 47.8 | |
| BM2 | Cut-off 1 | ≤38.70 | 47.2 (30.4 to 64.5) | 85.7 (73.8 to 93.6) | 70.7 | 67.1 (54 to 77.1) |
| | Cut-off 2 | ≤69.60 | 94.4 (81.3 to 99.3) | 25 (14.4 to 38.4) | 52.2 | |
| BM3 | Cut-off 1 | ≤12.50 | 91.7 (77.5 to 98.3) | 42.9 (29.7 to 56.8) | 62.0 | 70.1 (57.9 to 79.3) |
| | Cut-off 2 | ≤13.90 | 94.4 (81.3 to 99.3) | 28.6 (17.3 to 42.2) | 54.4 | |
| BM4 | Cut-off 1 | ≥12.20 | 36.1 (20.8 to 53.8) | 91.1 (80.4 to 97) | 69.6 | 56.5 (41.5 to 68.5) |
| | Cut-off 2 | ≥5.64 | 94.4 (81.3 to 99.3) | 0 (0 to 6.4) | 37.0 | |
| BM5 | Cut-off 1 | ≥13.90 | 44.4 (27.9 to 61.9) | 91.1 (80.4 to 97) | 72.8 | 63.7 (50 to 74.2) |
| | Cut-off 2 | ≥8.45 | 94.4 (81.3 to 99.3) | 23.2 (13 to 36.4) | 51.1 | |
| BM6 | Cut-off 1 | ≥20.00 | 41.7 (25.5 to 59.2) | 87.5 (75.9 to 94.8) | 69.6 | 60.9 (47 to 71.9) |
| | Cut-off 2 | ≥12.00 | 94.4 (81.3 to 99.3) | 0 (0 to 6.4) | 37.0 | |
| BM7 | Cut-off 1 | ≤161.00 | 66.7 (49 to 81.4) | 69.6 (55.9 to 81.2) | 68.5 | 69.8 (56.6 to 79.5) |
| | Cut-off 2 | ≤207.00 | 94.4 (81.3 to 99.3) | 14.3 (6.4 to 26.2) | 45.7 | |
| BM8 | Cut-off 1 | ≤12.70 | 75 (57.8 to 87.9) | 69.6 (55.9 to 81.2) | 71.7 | 70.6 (57.6 to 80.2) |
| | Cut-off 2 | ≤16.10 | 94.4 (81.3 to 99.3) | 8.9 (3 to 19.6) | 42.4 | |
| BM9 | Cut-off 1 | ≥4.06 | 58.3 (40.8 to 74.5) | 69.6 (55.9 to 81.2) | 65.2 | 60.4 (46.7 to 71.3) |
| | Cut-off 2 | ≥2.43 | 94.4 (81.3 to 99.3) | 5.4 (1.1 to 14.9) | 40.2 | |
| BM10 | Cut-off 1 | ≥241.00 | 38.9 (23.1 to 56.5) | 83.9 (71.7 to 92.4) | 66.3 | 57.2 (43.5 to 68.4) |
| | Cut-off 2 | ≥106.00 | 94.4 (81.3 to 99.3) | 10.7 (4 to 21.9) | 43.5 | |
| BM11 | Cut-off 1 | ≤0.27 | 77.8 (60.9 to 89.9) | 62.5 (48.6 to 75.1) | 68.5 | 65.7 (52.3 to 76) |
| | Cut-off 2 | ≤0.36 | 94.4 (81.3 to 99.3) | 10.7 (4 to 21.9) | 43.5 | |
| BM12 | Cut-off 1 | ≥0.59 | 80.6 (64 to 91.8) | 46.4 (33 to 60.3) | 59.8 | 65.1 (52.4 to 75) |
| | Cut-off 2 | ≥0.53 | 94.4 (81.3 to 99.3) | 25 (14.4 to 38.4) | 52.2 | |

[b]Test biomarkers alone without adding into baseline.
Cut-off 1: cut-off value at the Youden index.
Cut-off 2: cut-off value at the 95% sensitivity.

A.8.4 Phase III Model 3 Cut-off values for test biomarkers alone.

| Standalone test biomarkers[a] | Cut-off values | Value | Sensitivity % (95% CI) | Specificity % (95% CI) | Accuracy % | AUC % (95% CI) |
|---|---|---|---|---|---|---|
| BM1 | Cut-off 1 | ≤11.00 | 44.7 (30.2 to 59.9) | 81.8 (67.3 to 91.8) | 62.6 | 65.7 (53 to 75.5) |
| | Cut-off 2 | ≤18.80 | 95.7 (85.5 to 99.5) | 18.2 (8.2 to 32.7) | 58.2 | |
| BM2 | Cut-off 1 | ≤38.70 | 42.6 (28.3 to 57.8) | 86.4 (72.7 to 94.8) | 63.7 | 65 (52.1 to 75) |
| | Cut-off 2 | ≤78.40 | 95.7 (85.5 to 99.5) | 18.2 (8.2 to 32.7) | 58.2 | |
| BM3 | Cut-off 1 | ≤9.68 | 59.6 (44.3 to 73.6) | 77.3 (62.2 to 88.5) | 68.1 | 68.5 (55.8 to 78) |
| | Cut-off 2 | ≤17.00 | 95.7 (85.5 to 99.5) | 15.9 (6.6 to 30.1) | 57.1 | |
| BM4 | Cut-off 1 | ≥12.20 | 40.4 (26.4 to 55.7) | 100 (92 to 100) | 69.2 | 67.2 (54.1 to 77.1) |
| | Cut-off 2 | ≥5.64 | 95.7 (85.5 to 99.5) | 0 (0 to 8) | 49.5 | |
| BM5 | Cut-off 1 | ≥11.70 | 57.5 (42.2 to 71.7) | 84.1 (69.9 to 93.4) | 70.3 | 74.3 (62.3 to 82.9) |
| | Cut-off 2 | ≥8.45 | 95.7 (85.5 to 99.5) | 29.6 (16.8 to 45.2) | 63.7 | |
| BM6 | Cut-off 1 | ≥20.00 | 44.7 (30.2 to 59.9) | 95.5 (84.5 to 99.4) | 69.2 | 68.8 (56.1 to 78.3) |
| | Cut-off 2 | ≥12.00 | 95.7 (85.5 to 99.5) | 0 (0 to 8) | 49.5 | |

-continued

A.8.4 Phase III Model 3 Cut-off values for test biomarkers alone.

| Standalone test biomarkers[a] | Cut-off values | Value | Sensitivity % (95% CI) | Specificity % (95% CI) | Accuracy % | AUC % (95% CI) |
|---|---|---|---|---|---|---|
| BM7 | Cut-off 1 | ≤142.00 | 55.3 (40.1 to 69.8) | 90.9 (78.3 to 97.5) | 72.5 | 71.7 (58.7 to 81.1) |
| | Cut-off 2 | ≤232.00 | 95.7 (85.5 to 99.5) | 2.3 (0.1 to 12) | 50.6 | |
| BM8 | Cut-off 1 | ≤12.70 | 68.1 (52.9 to 80.9) | 72.7 (57.2 to 85) | 70.3 | 67.5 (54.6 to 77.3) |
| | Cut-off 2 | ≤18.30 | 95.7 (85.5 to 99.5) | 4.6 (0.6 to 15.5) | 51.7 | |
| BM9 | Cut-off 1 | ≥3.83 | 63.8 (48.5 to 77.3) | 68.2 (52.4 to 81.4) | 65.9 | 62.7 (49.5 to 73) |
| | Cut-off 2 | ≥2.41 | 95.7 (85.5 to 99.5) | 4.6 (0.6 to 15.5) | 51.7 | |
| BM10 | Cut-off 1 | ≥246.00 | 40.4 (26.4 to 55.7) | 93.2 (81.3 to 98.6) | 65.9 | 61.2 (47.9 to 71.7) |
| | Cut-off 2 | ≥95.30 | 95.7 (85.5 to 99.5) | 4.6 (0.6 to 15.5) | 51.7 | |
| BM11 | Cut-off 1 | ≤0.27 | 59.6 (44.3 to 73.6) | 61.4 (45.5 to 75.6) | 60.4 | 57.7 (44.7 to 68.4) |
| | Cut-off 2 | ≤0.36 | 95.7 (85.5 to 99.5) | 13.6 (5.2 to 27.4) | 56.0 | |
| BM12 | Cut-off 1 | ≥0.59 | 78.7 (64.3 to 89.3) | 50 (34.6 to 65.4) | 64.8 | 66.4 (53.8 to 76.2) |
| | Cut-off 2 | ≥0.42 | 95.7 (85.5 to 99.5) | 9.1 (2.5 to 21.7) | 53.9 | |

[b]. Test biomarkers alone without adding into baseline.
Cut-off 1: cut-off value at the Youden index.
Cut-off 2: cut-off value at the 95% sensitivity.

3.6. Results of Phase IV

Phase III identified CD11c, CD59, CD91 and CD163 as potential biomarkers to differentiate individuals who are PET Aβ positive (CI >25) versus those who are PET Aβ negative (CL<25) after correction for age, gender, education and APOE ε 4 allele status (Model 1, P=0.021). Applicants then validated them in an independent cohort (Phase IV, N=112). Several leukocyte markers showed connection to clinical diagnosis or association with Centiloids, which are consistent with Phase III. A multivariable model for the validation cohort found that a combination of CD59 & CD91 discriminated Aβ status, CL>25 or CL<25, with an AUC of 0.91 (CI: 0.81 to 0.99). The AUC was 0.1 higher than for the mean base model AUC at 0.81 (CI: 0.72 to 0.9) and after correction for age, gender, education and APOE c 4 allele status (p=0.072). A combination of CD11c, CD59 & CD91 was tried, had an AUC after correction at 0.95 (CI: 0.86 to 1), 0.14 above base model, p=0.05, although this value could reflect an overfitting due to the relatively small sample size (Detailed in Table 3.5).

4. Discussion:

Leukocyte surface markers exhibited differential expression when compared among groups of CN, MCI and AD, and/or associated with A13-PET data. The design of Phases I and II was maximal in variety of major CD markers that constrained its screening capacity. The new scope of leukocyte surface markers in Phase III was adjusted to reflecting the GWAS and other evidence that phagocytosis/endocytosis in the microglial/monocyte pathways may play a key role in AD pathogenesis [7, 21]. Although the exact molecular mechanism remains unclear, decreased expression of phagocytic receptors, MerTK and P2X7; scavenger receptors, CD36 and CD163; and integrins, CD11b, CD11c and CD18, accords closely with certain of the present inventors' previous work [7] that infers an impaired monocyte phagocytic function in the AD patients (Table 1; FIG. 1 Left). It is also notable that CD18 is a common subunit of CD11b/CD18 and CD11c/CD18, which are also known as complement receptor 3 and 4 (CR3, CR4). Both CR3 and CR4 have been found to be down-regulated in AD by this study. CD59 is a main inhibitor of the membrane attack complex (MAC) [22]. What Applicants found the upregulation of CD59 in AD may prevent cell lysis and phagocytic clearance. See FIG. 1 Right side. Orchestrated changes in two or more pathways represent a functional inhibition in AD associated with opsonisation, phagocytosis and clearance of pathogenic factors.

In this study, three markers, CD33, CD35/CR1 and CD91, are protein products of AD risk genes reported by GWAS meta-analysis [23, 24] or by other genetic association studies [25-27]. Both CD35 and CD91 were found up-regulated in AD by this study. Bradshaw et al. [28] found that the CD33 risk allele, rs3865444C, was associated with greater cell surface expression of CD33 in the monocytes of young and older individuals; however, it was associated with diminished internalization of Aβ42, accumulation of neuritic tau-positive change and increased numbers of activated human microglia. Over-expression of CD33 on monocytes in individuals carrying the rs3865444C risk genotype may be a mechanism to compensate its loss of function. CD35/CR1 is a receptor for complement factors, C3b and C4b [29], but its relevance to AD is unknown. CD91 is a receptor for ApoE, and the endocytosis and degradation of secreted amyloid precursor protein (APP) [30], suggesting that a single pathway links two molecules implicated in the pathophysiology of AD.

Besides CD91, RAGE is also a receptor for Aβ. Yan et al. [31] reported that expression of RAGE increased in AD, particularly in neurons close to deposits of Aβ and to neurofibrillary tangles. In mice, Deane et al. [32] showed that RAGE mediated the transport of human Aβ40 and Aβ42 across the blood-brain barrier and resulted in the expression of proinflammatory cytokines and endothelin-1. Arancio et al. [33] showed that RAGE is a cofactor for Aβ-induced neuronal perturbation and is involved in microglial cell activation in transgenic mice. In the current study, expression of RAGE was increased in AD, consistent with Yan et al. [31] and it may provide a mirror to what happens in brain-resident microglia. CD36 was found to be down-regulated in AD in this study. CD36 is a receptor for oxidized low density lipoprotein (LDL) [34] and a receptor for Aβ [35]. Immobilized Aβ oligomers bound CD36-Fc protein showed comparable affinity to that of RAGE-Fc and TREM2-Fc [36].

Applicants' data from blood grouping suggest there may be abnormalities in percentages of lymphocytes and monocytic subsets. Hematopoietic aging is characterized by expansion of hematopoietic stem cells (HSCs) with impaired function, that more myeloid and fewer lymphoid daughter cell are generated, which is termed as myeloid-biased haematopoiesis [37, 38]. The percentage of each type of leukocyte in the blood is largely determined by differences in stem cell activity and hence, decreased lymphocytes might be due to this myelopoiesis [39]. However, such differences do not explain the observed patterns of other monocytic subsets altered in opposite direction. It is possible that CD14+CD16+ monocytes (a highly phagocytic cells resembling tissue macrophages) exudate into sites of Aβ plaques in the brain, leading to a transient decline in MCI and an incomplete recovery in AD, most likely due to failure in chemotactic function or obliterated passage, representing a U-shaped response. It is apparent from the patterns of CD14−CD16+ monocytes that these two minor monocytic subsets had similar responses, whereas the CD14−CD16+ monocytes had lesser recovery in AD. Either percentage of CD14+CD16+ or percentage of CD14−CD16+ was correlated with none of CL, EM or PACC, due to this U-shaped response. It is interesting to note that percentage of monocytes in the blood did not change, possibly due to this subset inconsistency.

Applicants and others have found that a significant percentage (30%) of CN individuals show high Aβ PET and low Aβ42 levels in the CSF, these people are now classified as preclinical AD. Mild Cognitive Impairment (MCI) is considered a prodromal phase of AD, with 40-60% of people meeting criteria for MCI eventually progressing to clinical AD, or about 5-25% per year [40]. Diagnostic decision making is a two-class prediction problem; hence Applicants established a binary classifier, i.e. health and disease, and the classifier boundary was determined by the logistic model. Unfortunately, diagnosis of AD is based a multidimensional criteria, including clinical considerations, cognition, behaviour, advanced imaging and CSF biomarkers, moreover, there is neither specific criterion for early detection, nor is a clear definition for preclinical stages, and, thus, Applicants used CL as a simple surrogate for identifying stages in the model 1 and 2, however, Applicants further added clinical classifications into the model 3 to reflecting the latest movements made by NIA-AA [13] and IWG [41].

Applicants' findings may have implications for early diagnosis for individuals at increased risk from genetic factor (e.g. APOE) to watch for preclinical signs of AD without obvious changes in neuroimaging or CSF biomarkers and to initiate early intervention. The use of plasma biomarkers for AD has been demonstrated recently by Nakamura et al. and Fossati et al. [15, 42], therefore, justify the reason using blood based biomarkers for AD diagnosis, and Applicants' novel findings could attribute to, if connected, AD proteinopathies in the blood. The role of the altered leukocyte biomarkers or blood grouping or transcriptional networks such as PU.1 [21, 43] in modulating these processes remains to be determined but may contribute to molecular pathology of AD.

4.7. In conclusion, Applicants' results suggest that leukocyte biomarkers are objective, measurable indicator of AD progression and could be valuable for early diagnosis. Furthermore, leukocyte biomarkers are superior in terms of cost and simplicity and can be easily employed in the clinic, confirming the importance of leukocyte biomarkers for development of novel efficacious drug as well as outcome measures for all phases of clinical trials.

REFERENCES

[1] 2020 Alzheimer's disease facts and figures. Alzheimers Dement. 2020.

[2] Scheltens P, Blennow K, Breteler M M B, de Strooper B, Frisoni G B, Salloway S, et al. Alzheimer's disease. The Lancet. 2016; 388:505-17.

[3] Wang J, Gu B J, Masters C L, Wang Y J. A systemic view of Alzheimer disease—insights from amyloid-beta metabolism beyond the brain. Nat Rev Neurol. 2017; 13:612-23.

[4] Coraci I S, Husemann J, Berman J W, Hulette C, Dufour J H, Campanella G K, et al. CD36, a class B scavenger receptor, is expressed on microglia in Alzheimer's disease brains and can mediate production of reactive oxygen species in response to beta-amyloid fibrils. Am J Pathol. 2002; 160:101-12.

[5] Frenkel D, Wilkinson K, Zhao L, Hickman S E, Means T K, Puckett L, et al. Scaral deficiency impairs clearance of soluble amyloid-beta by mononuclear phagocytes and accelerates Alzheimer's-like disease progression. Nat Commun. 2013; 4:2030.

[6] Roberts K F, Elbert D L, Kasten T P, Patterson B W, Sigurdson W C, Connors R E, et al. Amyloid-beta efflux from the central nervous system into the plasma. Ann Neurol. 2014; 76:837-44.

[7] Gu B J, Huang X, Ou A, Rembach A, Fowler C, Avula P K, et al. Innate phagocytosis by peripheral blood monocytes is altered in Alzheimer's disease. Acta Neuropathol. 2016; 132:377-89.

[8] Cheng Y, Tian D Y, Wang Y J. Peripheral clearance of brain-derived Abeta in Alzheimer's disease: pathophysiology and therapeutic perspectives. Transl Neurodegener. 2020; 9:16.

[9] Tosto G, Reitz C. Genome-wide association studies in Alzheimer's disease: a review. Curr Neurol Neurosci Rep. 2013; 13:381.

[10] Jack C R, Jr., Bennett D A, Blennow K, Carrillo M C, Feldman H H, Frisoni G B, et al. A/T/N: An unbiased descriptive classification scheme for Alzheimer disease biomarkers. Neurology. 2016; 87:539-47.

[11] Fagan A M, Xiong C, Jasielec M S, Bateman R J, Goate A M, Benzinger T L, et al. Longitudinal change in CSF biomarkers in autosomal-dominant Alzheimer's disease. Sci Transl Med. 2014; 6:226ra30.

[12] Dubois B, Hampel H, Feldman H H, Scheltens P, Aisen P, Andrieu S, et al. Preclinical Alzheimer's disease: Definition, natural history, and diagnostic criteria. Alzheimers Dement. 2016; 12:292-323.

[13] Sperling R A, Aisen P S, Beckett L A, Bennett D A, Craft S, Fagan A M, et al. Toward defining the preclinical stages of Alzheimer's disease: recommendations from the National Institute on Aging-Alzheimer's Association workgroups on diagnostic guidelines for Alzheimer's disease. Alzheimers Dement. 2011; 7:280-92.

[14] McKhann G M, Knopman D S, Chertkow H, Hyman B T, Jack C R, Jr., Kawas C H, et al. The diagnosis of dementia due to Alzheimer's disease: recommendations from the National Institute on Aging-Alzheimers Association workgroups on diagnostic guidelines for Alzheimer's disease. Alzheimers Dement. 2011; 7:263-9.

[15] Nakamura A, Kaneko N, Villemagne V L, Kato T, Doecke J, Dore V, et al. High performance plasma amyloid-beta biomarkers for Alzheimer's disease. Nature. 2018; 554:249-54.

[16] Janelidze S, Berron D, Smith R, Strandberg O, Proctor N K, Dage J L, et al. Associations of Plasma

51

Phospho-Tau217 Levels With Tau Positron Emission Tomography in Early Alzheimer Disease. JAMA Neurol. 2020.

[17] Klunk W E, Koeppe R A, Price J C, Benzinger T L, Devous M D, Sr., Jagust W J, et al. The Centiloid Project: standardizing quantitative amyloid plaque estimation by PET. Alzheimers Dement. 2015; 11:1-15 e1-4.

[18] Bourgeat P, Dore V, Fripp J, Ames D, Masters C L, Salvado 0, et al. Implementing the centiloid transformation for (11)C-PiB and beta-amyloid (18)F-PET tracers using CapAIBL. Neuroimage. 2018; 183:387-93.

[19] Lim Y Y, Maruff P, Pietrzak R H, Ames D, Ellis K A, Harrington K, et al. Effect of amyloid on memory and non-memory decline from preclinical to clinical Alzheimer's disease. Brain. 2014; 137:221-31.

[20] Lim Y Y, Snyder P J, Pietrzak R H, Ukiqi A, Villemagne V L, Ames D, et al. Sensitivity of composite scores to amyloid burden in preclinical Alzheimer's disease: Introducing the Z-scores of Attention, Verbal fluency, and Episodic memory for Nondemented older adults composite score. Alzheimers Dement (Amst). 2016; 2:19-26.

[21] Tansey K E, Cameron D, Hill M J. Genetic risk for Alzheimer's disease is concentrated in specific macrophage and microglial transcriptional networks. Genome Med. 2018; 10:14.

[22] Blom A M. The role of complement inhibitors beyond controlling inflammation. J Intern Med. 2017; 282:116-28.

[23] Naj A C, Jun G, Beecham G W, Wang L S, Vardarajan B N, Buros J, et al. Common variants at MS4A4/MS4A6E, CD2A P, CD33 and EPHA1 are associated with late-onset Alzheimer's disease. Nat Genet. 2011; 43:436-41.

[24] Lambert J C, Heath S, Even G, Campion D, Sleegers K, Hiltunen M, et al. Genome-wide association study identifies variants at CLU and CR1 associated with Alzheimer's disease. Nat Genet. 2009; 41:1094-9.

[25] Lendon C L, Talbot C J, Craddock N J, Han S W, Wragg M, Morris J C, et al. Genetic association studies between dementia of the Alzheimer's type and three receptors for apolipoprotein E in a Caucasian population. Neurosci Lett. 1997; 222:187-90.

[26] Hollenbach E, Ackermann S, Hyman B T, Rebeck G W. Confirmation of an association between a polymorphism in exon 3 of the low-density lipoprotein receptor-related protein gene and Alzheimer's disease. Neurology. 1998; 50:1905-7.

[27] Baum L, Chen L, Ng H K, Chan Y S, Mak Y T, Woo J, et al. Low density lipoprotein receptor related protein gene exon 3 polymorphism association with Alzheimer's disease in Chinese. Neurosci Lett. 1998; 247:33-6.

[28] Bradshaw E M, Chibnik L B, Keenan B T, Ottoboni L, Raj T, Tang A, et al. CD33 Alzheimer's disease locus: altered monocyte function and amyloid biology. Nat Neurosci. 2013; 16:848-50.

[29] Klickstein L B, Bartow T J, Miletic V, Rabson L D, Smith J A, Fearon D T. Identification of distinct C3b and C4b recognition sites in the human C3b/C4b receptor (CR1, CD35) by deletion mutagenesis. J Exp Med. 1988; 168:1699-717.

[30] Kounnas M Z, Moir R D, Rebeck G W, Bush A I, Argraves W S, Tanzi R E, et al. LDL receptor-related protein, a multifunctional ApoE receptor, binds secreted beta-amyloid precursor protein and mediates its degradation. Cell. 1995; 82:331-40.

[31] Yan S D, Chen X, Fu J, Chen M, Zhu H, Roher A, et al. RAGE and amyloid-beta peptide neurotoxicity in Alzheimer's disease. Nature. 1996; 382:685-91.

[32] Deane R, Du Yan S, Submamaryan R K, LaRue B, Jovanovic S, Hogg E, et al. RAGE mediates amyloid-beta peptide transport across the blood-brain barrier and accumulation in brain. Nat Med. 2003; 9:907-13.

[33] Arancio O, Zhang H P, Chen X, Lin C, Trinchese F, Puzzo D, et al. RAGE potentiates Abeta-induced perturbation of neuronal function in transgenic mice. EMBO J. 2004; 23:4096-105.

[34] Endemann G, Stanton L W, Madden K S, Bryant C M, White R T, Protter A A. CD36 is a receptor for oxidized low density lipoprotein. J Biol Chem. 1993; 268:11811-6.

[35] Stewart C R, Stuart L M, Wilkinson K, van Gils J M, Deng J, Halle A, et al. CD36 ligands promote sterile inflammation through assembly of a Toll-like receptor 4 and 6 heterodimer. Nat Immunol. 2010; 11:155-61.

[36] Zhao Y, Wu X, Li X, Jiang L L, Gui X, Liu Y, et al. TREM2 Is a Receptor for beta-Amyloid that Mediates Microglial Function. Neuron. 2018; 97:1023-31 e7.

[37] Pang W W, Price E A, Sahoo D, Beerman I, Maloney W J, Rossi D J, et al. Human bone marrow hematopoietic stem cells are increased in frequency and myeloid-biased with age. Proc Natl Acad Sci USA. 2011; 108:20012-7.

[38] Ho Y H, Del Toro R, Rivera-Torres J, Rak J, Korn C, Garcia-Garcia A, et al. Remodeling of Bone Marrow Hematopoietic Stem Cell Niches Promotes Myeloid Cell Expansion during Premature or Physiological Aging. Cell Stem Cell. 2019; 25:407-18 e6.

[39] Sampath P, Moideen K, Ranganathan U D, Bethunaickan R. Monocyte Subsets: Phenotypes and Function in Tuberculosis Infection. Front Immunol. 2018; 9:1726.

[40] Masters C L, Bateman R, Blennow K, Rowe C C, Sperling R A, Cummings J L. Alzheimer's disease. Nat Rev Dis Primers. 2015; 1:15056.

[41] Wu Y T, Fratiglioni L, Matthews F E, Lobo A, Breteler M M, Skoog I, et al. Dementia in western Europe: epidemiological evidence and implications for policy making. Lancet Neurol. 2016; 15:116-24.

[42] Fossati S, Ramos Cejudo J, Debure L, Pirraglia E, Sone J Y, Li Y, et al. Plasma tau complements CSF tau and P-tau in the diagnosis of Alzheimer's disease. Alzheimers Dement (Amst). 2019; 11:483-92.

[43] Huang K L, Marcora E, Pimenova A A, Di Narzo A F, Kapoor M, Jin S C, et al. A common haplotype lowers PU.1 expression in myeloid cells and delays onset of Alzheimer's disease. Nat Neurosci. 2017; 20:1052-61.

[44] Fourgeaud L, Traves P G, Tufail Y, Leal-Bailey H, Lew E D, Burrola P G, et al. TAM receptors regulate multiple features of microglial physiology. Nature. 2016; 532:240-4.

[45] Gal A, Li Y, Thompson D A, Weir J, Orth U, Jacobson S G, et al. Mutations in MERTK, the human orthologue of the RCS rat retinal dystrophy gene, cause retinitis pigmentosa. Nat Genet. 2000; 26:270-1.

[46] Kunis G, Baruch K, Rosenzweig N, Kertser A, Miller O, Berkutzki T, Schwartz M (2013) IFN-gamma-dependent activation of the brain's choroid plexus for CNS immune surveillance and repair. Brain 136, 3427-3440.

[47] Baruch K, Deczkowska A, Rosenzweig N, Tsitsou-Kampeli A, Sharif A M, Matcovitch-Natan O, Kertser A, David E, Amit I, Schwartz M (2016) PD-1 immune checkpoint blockade reduces pathology and improves memory in mouse models of Alzheimer's disease. Nat Med 22, 135-137.

[48] Rezai-Zadeh K, Gate D, Szekely C A, Town T (2009) Can peripheral leukocytes be used as Alzheimer's disease biomarkers? Expert Rev Neurother 9, 1623-1633.

[49] Jiang Y, Zhou X, Ip F C, Chan P, Chen Y, Lai N C H, Cheung K, Lo R M N, Tong E P S, Wong B W Y, Chan A L T, Mok V C T, Kwok T C Y, Mok K Y, Hardy J, Zetterberg H, Fu A K Y, Ip N Y (Epub May 25, 2021) Large-scale plasma proteomic profiling identifies a high-performance biomarker panel for Alzheimer's disease screening and staging. Alzheimers Dement. 2022; 18(1), 88-102.

[50] Phongpreecha T, Fernandez R, Mrdjen D, Culos A, Gajera C R, Wawro A M, Stanley N, Gaudilliere B, Poston K L, Aghaeepour N, Montine T J (2020) Single-cell peripheral immunoprofiling of Alzheimer's and Parkinson's diseases. Sci Adv 6 (48) (available at: https://www.ncbi.nlm.nih.gov/pmc/articles/PMC7688332/pdf/abd5575.pdf).

[51] Fowler C, Rainey-Smith S R, Bird S, Bomke J, Bourgeat P, Brown B M, Burnham S C, Bush A I, Chadunow C, Collins S, Doecke J, Dore V, Ellis K A, Evered L, Fazlollahi A, Fripp J, Gardener S L, Gibson S, Grenfell R, Harrison E, Head R, Jin L, Kamer A, Lamb F, Lautenschlager N T, Laws S M, Li Q X, Lim L, Lim Y Y, Louey A, Macaulay S L, Mackintosh L, Martins R N, Maruff P, Masters C L, McBride S, Milicic L, Peretti M, Pertile K, Porter T, Radler M, Rembach A, Robertson J, Rodrigues M, Rowe C C, Rumble R, Salvado O, Savage G, Silbert B, Soh M, Sohrabi H R, Taddei K, Taddei T, Thai C, Trounson B, Tyrrell R, Vacher M, Varghese S, Villemagne V L, Weinborn M, Woodward M, Xia Y, Ames D, the Ai (2021) Fifteen Years of the Australian Imaging, Biomarkers and Lifestyle (AIBL) Study: Progress and Observations from 2,359 Older Adults Spanning the Spectrum from Cognitive Normality to Alzheimer's Disease. J Alzheimers Dis Rep 5, 443-468.

[52] Sperling R A, Donohue M C, Raman R, Sun C K, Yaari R, Holdridge K, Siemers E, Johnson K A, Aisen P S, Team A S (2020) Association of Factors With Elevated Amyloid Burden in Clinically Normal Older Individuals. JAMA Neurol 77, 735-745.

[53] Rowe C C, Ellis K A, Rimajova M, Bourgeat P, Pike K E, Jones G, Fripp J, Tochon-Danguy H, Morandeau L, O'Keefe G, Price R, Raniga P, Robins P, Acosta O, Lenzo N, Szoeke C, Salvado O, Head R, Martins R, Masters C L, Ames D, Villemagne V L (2010) Amyloid imaging results from the Australian Imaging, Biomarkers and Lifestyle (AIBL) study of aging. Neurobiol Aging 31, 1275-1283.

[54] Bourgeat P, Villemagne V L, Dore V, Brown B, Macaulay S L, Martins R, Masters C L, Ames D, Ellis K, Rowe C C, Salvado O, Fripp J, Group A R (2015) Comparison of M R-less PiB SUVR quantification methods. Neurobiol Aging 36 Suppl 1, S159-166.

[55] Pencina M J, D'Agostino R B, Sr., D'Agostino R B, Jr., Vasan R S (2008) Evaluating the added predictive ability of a new marker: from area under the ROC curve to reclassification and beyond. Stat Med 27, 157-172; discussion 207-112.

[56] Pickering J W, Endre Z H (2012) New metrics for assessing diagnostic potential of candidate biomarkers. Clin J Am Soc Nephrol 7, 1355-1364.

[57] Steyerberg E W, Vickers A J, Cook N R, Gerds T, Gonen M, Obuchowski N, Pencina M J, Kattan M W (2010) Assessing the performance of prediction models: a framework for traditional and novel measures. Epidemiology 21, 128-138.

[58] BRIER G W (1950) VERIFICATION OF FORECASTS EXPRESSED IN TERMS OF PROBABILITY. Monthly Weather Review 78, 1-3.

[59] Raposo C, Graubardt N, Cohen M, Eitan C, London A, Berkutzki T, Schwartz M (2014) CNS repair requires both effector and regulatory T cells with distinct temporal and spatial profiles. J Neurosci 34, 10141-10155.

[60] Baruch K, Deczkowska A, David E, Castellano J M, Miller O, Kertser A, Berkutzki T, Barnett-Itzhaki Z, Bezalel D, Wyss-Coray T, Amit I, Schwartz M (2014) Aging. Aging-induced type I interferon response at the choroid plexus negatively affects brain function. Science 346, 89-93.

CLAUSES

Clause 1. A composition comprising:
a binding agent for CD163 conjugated with a detectable moiety.

Clause 2. The composition of clause 1, wherein the binding agent for CD163 is chosen from a single chain variable fragment, an antibody mimetic, an antibody fragment, an antibody, a monoclonal antibody, and combinations thereof.

Clause 3. The composition of any one of clauses 1-2, wherein the detectable moiety is chosen from a radioisotope, a stable isotope, a fluorophore, and combinations thereof.

Clause 4. A composition comprising:
a mouse anti-human IgG monoclonal antibody for CD163 conjugated with a fluorophore; and
ethylene diamine tetraacetic acid, at least one salt thereof, citric acid, at least one salt thereof, or a combination of any of the foregoing.

Clause 5. A composition comprising:
a mouse anti-human IgG monoclonal antibody for CD163 conjugated with a fluorophore;
ethylene diamine tetraacetic acid, at least one salt thereof, citric acid, at least one salt thereof, or a combination of any of the foregoing; and
whole blood of a human patient.

Clause 6. A composition comprising:
a mouse anti-human IgG monoclonal antibody for CD163 conjugated with a fluorophore; and
at least one anti-coagulant.

Clause 7. The composition of clause 6, wherein the at least one anti-coagulant is chosen from ethylene diamine tetraacetic acid, at least one salt thereof, citric acid, at least one salt thereof, or a combination of any of the foregoing.

Clause 8. The composition of any one of clauses 4-7, wherein the composition does not contain heparin.

Clause 9. The composition of any one of clauses 4-8, wherein the composition does not contain allophycocyanin.

Clause 10. The composition of any one of clauses 4-9, further comprising bovine serum albumin and sodium azide.

Clause 11. The composition of any one of clauses 4-10, wherein the fluorophore is chosen from fluorescein isothiocyanate, allophycocyanin, or a combination thereof.

Clause 12. The composition of any one of clauses 4-10, wherein the fluorophore is chosen from: fluorescent dye sold under the trademark Alexa Fluor® 488 (Molecular Probes, Inc., Eugene OR); fluorescent dye sold under the trademark Alexa Fluor® 647 (Molecular Probes, Inc., Eugene OR); BUV395; BUV563; BUV615; BUV661; BUV737; BUV805, BV421; BV480; BV510, BV605; BV650; BV711, BV750; BV786; FITC; PE; PE-CF594; PerCP-Cy™5.5; R718; or a combination of two or more thereof.

Clause 13. The composition of any one of clauses 4-10, wherein the fluorophore is chosen from: fluorescein, rhodamine, lanthanide phosphors, and their derivatives thereof. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine, tetramethylrhodamine, and sulforhodamine.

Clause 14. The composition of any one of clauses 4-10, wherein the fluorophore is chosen from fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, R-Phycoerythrin, Allophycocyanin, or other fluorophores known in the art.

Clause 15. The composition of any one of clauses 4-14, wherein the composition does not contain fluorescent dye sold under the trademark Alexa Fluor® 488 (Molecular Probes, Inc., Eugene OR).

Clause 16. The composition of any one of clauses 4-15, wherein the composition does not contain heparin.

Clause 17. The composition of any one of clauses 1-16, wherein the composition further comprises a second binding agent for for one or more of scavenger receptors and their regulators conjugated with a second detectable moiety.

Clause 18. The composition of clause 17, wherein the second binding agent is chosen from a single chain variable fragment, an antibody mimetic, an antibody fragment, an antibody, a monoclonal antibody, and combinations thereof.

Clause 19. The composition of any one of clauses 17-18, wherein the second detectable moiety is chosen from a radioisotope, a stable isotope, a fluorophore, and combinations thereof.

Clause 20. A method for diagnosing AD in a human patient, comprising:
obtaining a blood sample from the human patient;
optionally storing the blood sample in ice;
optionally testing the blood sample within three hours of obtaining the blood sample;
reacting the blood sample with a mouse anti-human IgG monoclonal antibody for CD163 conjugated with a fluorophore to obtain bound CD163;
measuring the concentration of bound CD163 in the blood sample by fluorescence of the fluorophore;
comparing the concentration with a concentration range of CD163 in healthy humans;
observing a decreased concentration of CD163 in the blood sample; thereby diagnosing AD in the human patient.

Clause 21. The method of clause 20, wherein the measuring the concentration of bound CD163 comprises measuring the mean fluorescence intensity of bound CD163 on leukocytes.

Clause 22. The method of any one of clauses 20-21, wherein the comparing the concentration comprises comparing the mean fluorescence intensity of bound CD163 for the human patient with the mean fluorescence intensity of bound CD163 for a pool of human participants who have <25CL as measured by amyloid PET imaging.

Clause 23. The method of any one of clauses 20-22, wherein the observing a decreased concentration of CD163 in the blood sample comprises measuring a decrease in mean fluorescence intensity of at least about 11%, at least about 12%, at least about 13%, at least about 14%, at least about 15%, at least about 16%, at least about 17%, at least about 18%, or at least about 19% compared to a mean fluorescence intensity of bound CD163 for a pool of human participants who have <25CL as measured by amyloid PET imaging.

Clause 24. The method of any one of clauses 20-23, wherein the mouse anti-human IgG monoclonal antibody for CD163 conjugated with a fluorophore comprises mouse anti-human CD163 antigen conjugated with fluorescent dye sold under the trademark Alexa Fluor® 647 (Molecular Probes, Inc., Eugene OR).

Clause 25. A method for determining the efficacy of an AD therapeutic candidate in a human patient, comprising:
(A) obtaining a first blood sample from the human patient;
optionally storing the first blood sample in ice;
optionally testing the first blood sample within three hours of obtaining the first blood sample;
reacting the first blood sample with
a mouse anti-human IgG monoclonal antibody for CD163 conjugated with a fluorophore to obtain first bound CD163;
measuring a first concentration of first bound CD163 in the first blood sample by fluorescence of the fluorophore;
(B) administering the AD therapeutic candidate to the human patient;
(C) obtaining a second blood sample from the human patient;
optionally storing the second blood sample in ice;
optionally testing the second blood sample within three hours of obtaining the second blood sample;
reacting the second blood sample with
the mouse anti-human IgG monoclonal antibody for CD163 conjugated with the fluorophore to obtain second bound CD163;
measuring a second concentration of second bound CD163 in the second blood sample by fluorescence of the fluorophore;
(D) observing increase from the first concentration of first bound CD163 to the second concentration of second bound CD163;
(E) thereby determining the efficacy of the AD therapeutic candidate in the human patient.

Clause 26. The method of clause 25, wherein the AD therapeutic candidate is a phagocytosis-promoting agent.

Clause 27. The method of clause 25, wherein the AD therapeutic candidate is a scavenger receptor agonist.

Clause 28. The method of any one of clauses 25-27, wherein the measuring the first concentration comprises measuring the first concentration on leukocytes, and the measuring the second concentration comprises measuring the second concentration on leukocytes.

Clause 29. A composition comprising a binding agent for CD91 conjugated with a detectable moiety.

Clause 30. The composition of clause 29, wherein the binding agent is chosen from single chain variable fragments, antibody mimetics, antibody fragments, antibodies, monoclonal antibodies, and combinations thereof.

Clause 31. The composition of any one of clauses 29-30, wherein the detectable moiety is chosen from radioisotopes, stable isotopes, fluorophores, and combinations thereof.

Clause 32. A use of a binding agent for CD163 for the diagnosis of AD in a human patient in need thereof.

Clause 33. The use of clause 32, wherein the binding agent is chosen from single chain variable fragments, antibody mimetics, antibody fragments, antibodies, monoclonal antibodies, and combinations thereof.

Clause 34. The use of any one of clauses 32-33, wherein the binding agent is conjugated with a detectable moiety.

Clause 35. The use of clause 34, wherein the detectable moiety is chosen from radioisotopes, stable isotopes, fluorophores, and combinations thereof.

Clause 36. A binding agent for CD163 for use in the diagnosis of AD in a human patient in need thereof.

Clause 37. The binding agent for CD163 of clause 36, wherein the binding agent is chosen from single chain variable fragments, antibody mimetics, antibody fragments, antibodies, monoclonal antibodies, and combinations thereof.

Clause 38. The binding agent for CD163 of any one of clauses 36-37, wherein the binding agent is conjugated with a detectable moiety.

Clause 39. The binding agent for CD163 of clause 38, wherein the detectable moiety is chosen from radioisotopes, stable isotopes, fluorophores, and combinations thereof.

Clause 40. A method for diagnosing AD in a human patient, comprising:

obtaining a blood sample from the human patient;

optionally storing the blood sample in ice;

optionally testing the blood sample within three hours of obtaining the blood sample;

reacting the blood sample with a mouse anti-human IgG monoclonal antibody for CD91 conjugated with a fluorophore to obtain bound CD91;

measuring the concentration of bound CD91 in the blood sample by fluorescence of the fluorophore;

comparing the concentration with a concentration range of CD91 in healthy humans;

observing an increased concentration of CD91 in the blood sample; thereby diagnosing AD in the human patient.

Clause 41. The method of clause 40, wherein the measuring the concentration of bound CD91 comprises measuring the mean fluorescence intensity of bound CD91 on leukocytes.

Clause 42. The method of any one of clauses 40-41, wherein the comparing the concentration comprises comparing the mean fluorescence intensity of bound CD91 for the human patient with the mean fluorescence intensity of bound CD91 for a pool of human participants who have <25CL as measured by amyloid PET imaging.

Clause 43. The method of any one of clauses 40-42, wherein the observing an increased concentration of CD91 in the blood sample comprises measuring an increase in mean fluorescence intensity of at least about 44%, at least about 50%, at least about 55%, or at least about 59% compared to a mean fluorescence intensity of bound CD91 for a pool of human participants who have <25CL as measured by amyloid PET imaging.

Clause 44. A method for determining the efficacy of an AD therapeutic candidate in a human patient, comprising:

(A) obtaining a first blood sample from the human patient;

optionally storing the first blood sample in ice;

optionally testing the first blood sample within three hours of obtaining the first blood sample;

reacting the first blood sample with a mouse anti-human IgG monoclonal antibody for CD91 conjugated with a fluorophore to obtain first bound CD91;

measuring a first concentration of first bound CD91 in the first blood sample by fluorescence of the fluorophore;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with the mouse anti-human IgG monoclonal antibody for CD91 conjugated with the fluorophore to obtain second bound CD91;

measuring a second concentration of second bound CD91 in the second blood sample by fluorescence of the fluorophore;

(D) observing a decrease from the first concentration of first bound CD91 to the second concentration of second bound CD91;

(E) thereby determining the efficacy of the AD therapeutic candidate in the human patient.

Clause 45. The method of clause 44, wherein the AD therapeutic candidate is a phagocytosis-promoting agent.

Clause 46. The method of clause 44, wherein the AD therapeutic candidate is a scavenger receptor agonist.

Clause 47. The method of any one of clauses 44-46, wherein the measuring the first concentration comprises measuring the first concentration on leukocytes, and the measuring the second concentration comprises measuring the second concentration on leukocytes.

Clause 48. A use of a binding agent for CD91 for the diagnosis of AD in a human patient in need thereof.

Clause 49. The use of clause 48, wherein the binding agent is chosen from single chain variable fragments, antibody mimetics, antibody fragments, antibodies, monoclonal antibodies, and combinations thereof.

Clause 50. The use of any one of clauses 48-49, wherein the binding agent is conjugated with a detectable moiety.

Clause 51. The use of clause 50, wherein the detectable moiety is chosen from radioisotopes, stable isotopes, fluorophores, and combinations thereof.

Clause 52. A binding agent for CD91 for use in the diagnosis of AD in a human patient in need thereof.

Clause 53. The binding agent for CD91 of clause 52, wherein the binding agent is chosen from single chain variable fragments, antibody mimetics, antibody fragments, antibodies, monoclonal antibodies, and combinations thereof.

Clause 54. The binding agent for CD91 of any one of clauses 51-53, wherein the binding agent is conjugated with a detectable moiety.

Clause 55. The binding agent for CD91 of clause 54, wherein the detectable moiety is chosen from radioisotopes, stable isotopes, fluorophores, and combinations thereof.

Clause 56. A composition comprising a binding agent for MerTK conjugated with a detectable moiety.

Clause 57. The composition of clause 56, wherein the binding agent is chosen from single chain variable fragments, antibody mimetics, antibody fragments, antibodies, monoclonal antibodies, and combinations thereof.

Clause 58. The composition of any one of clauses 56-57, wherein the detectable moiety is chosen from radioisotopes, stable isotopes, fluorophores, and combinations thereof.

Clause 59. A method for diagnosing AD in a human patient, comprising:

obtaining a blood sample from the human patient;

optionally storing the blood sample in ice;

optionally testing the blood sample within three hours of obtaining the blood sample;

reacting the blood sample with a mouse anti-human IgG monoclonal antibody for MerTK conjugated with a fluorophore to obtain bound MerTK;

measuring the concentration of bound MerTK in the blood sample by fluorescence of the fluorophore;

comparing the concentration with a concentration range of MerTK in healthy humans;

observing a decreased concentration of MerTK in the blood sample;

thereby diagnosing AD in the human patient.

Clause 60. The method of clause 59, wherein the measuring the concentration of bound MerTK comprises measuring the mean fluorescence intensity of bound MerTK on leukocytes.

Clause 61. The method of any one of clauses 59-60, wherein the comparing the concentration comprises comparing the mean fluorescence intensity of bound MerTK for the human patient with the mean fluorescence intensity of bound MerTK for a pool of human participants who have <25CL as measured by amyloid PET imaging.

Clause 62. The method of any one of clauses 59-61, wherein the observing a decreased concentration of MerTK in the blood sample comprises measuring a decrease in mean fluorescence intensity of at least about 12% compared to a mean fluorescence intensity of bound MerTK for a pool of human participants who have <25CL as measured by amyloid PET imaging.

Clause 63. A method for determining the efficacy of an AD therapeutic candidate in a human patient, comprising:

(A) obtaining a first blood sample from the human patient;

optionally storing the first blood sample in ice;

optionally testing the first blood sample within three hours of obtaining the first blood sample;

reacting the first blood sample with a mouse anti-human IgG monoclonal antibody for MerTK conjugated with a fluorophore to obtain first bound MerTK;

measuring a first concentration of first bound MerTK in the first blood sample by fluorescence of the fluorophore;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with the mouse anti-human IgG monoclonal antibody for MerTK conjugated with the fluorophore to obtain second bound MerTK;

measuring a second concentration of second bound MerTK in the second blood sample by fluorescence of the fluorophore;

(D) observing an increase from the first concentration of first bound MerTK to the second concentration of second bound MerTK;

(E) thereby determining the efficacy of the AD therapeutic candidate in the human patient.

Clause 64. The method of clause 63, wherein the AD therapeutic candidate is a phagocytosis-promoting agent.

Clause 65. The method of clause 63, wherein the AD therapeutic candidate is a scavenger receptor agonist.

Clause 66. The method of any one of clauses 63-65, wherein the measuring the first concentration comprises measuring the first concentration on leukocytes, and the measuring the second concentration comprises measuring the second concentration on leukocytes.

Clause 67. A use of a binding agent for MerTK for the diagnosis of AD in a human patient in need thereof.

Clause 68. The use of clause 67, wherein the binding agent is chosen from single chain variable fragments, antibody mimetics, antibody fragments, antibodies, monoclonal antibodies, and combinations thereof.

Clause 69. The use of any one of clauses 67-68, wherein the binding agent is conjugated with a detectable moiety.

Clause 70. The use of clause 69, wherein the detectable moiety is chosen from radioisotopes, stable isotopes, fluorophores, and combinations thereof.

Clause 71. A binding agent for MerTK for use in the diagnosis of AD in a human patient in need thereof.

Clause 72. The binding agent for MerTK of clause 71, wherein the binding agent is chosen from single chain variable fragments, antibody mimetics, antibody fragments, antibodies, monoclonal antibodies, and combinations thereof.

Clause 73. The binding agent for MerTK of any one of clauses 84-85, wherein the binding agent is conjugated with a detectable moiety.

Clause 74. The binding agent for MerTK of clause 73, wherein the detectable moiety is chosen from radioisotopes, stable isotopes, fluorophores, and combinations thereof.

Clause 75. A composition comprising: a first binding agent for CD59 conjugated with a first detectable moiety; and a second binding agent for CD163 conjugated with a second detectable moiety.

Clause 76. The composition of clause 75, wherein the first binding agent and second binding agent are independently chosen from single chain variable fragments, antibody mimetics, antibody fragments, antibodies, monoclonal antibodies, and combinations thereof.

Clause 77. The composition of any one of clauses 75-76, wherein the first detectable moiety, second detectable moiety, and third detectable moiety are independently chosen from radioisotopes, stable isotopes, fluorophores, and combinations thereof.

Clause 78. A composition comprising:

a monoclonal antibody for CD59 conjugated with a first fluorophore; and a monoclonal antibody for CD163 conjugated with a second fluorophore.

Clause 79. A composition comprising:

a mouse anti-human IgG monoclonal antibody for CD59 conjugated with a first fluorophore; and a mouse anti-human IgG monoclonal antibody for CD163 conjugated with a second fluorophore.

Clause 80. The composition of any one of clauses 78-79, further comprising at least one anticoagulant.

Clause 81. The composition of any one of clauses 78-80, wherein the at least one anticoagulant comprises ethylene diamine tetraacetic acid, at least one salt thereof, citric acid, at least one salt thereof, or a combination of any of the foregoing.

Clause 82. The composition of any one of clauses 78-81, wherein the composition does not contain heparin.

Clause 83. The composition of any one of clauses 78-82, wherein the composition does not contain allophycocyanin.

Clause 84. The composition of any one of clause 78-83, wherein the composition does not contain fluorescent dye sold under the trademark Alexa Fluor® 647 (Molecular Probes, Inc., Eugene OR).

Clause 85. The composition of any one of clauses 78-84, further comprising bovine serum albumin and sodium azide.

Clause 86. The composition of any one of clauses 78-85, wherein the composition does not contain fluorescent dye sold under the trademark Alexa Fluor® 488 (Molecular Probes, Inc., Eugene OR).

Clause 87. The composition of any one of clauses 78-86, wherein the first fluorophore is R-phycoerythrin.

Clause 88. The composition of any one of clauses 78-87, wherein the second fluorophore is fluorescent dye sold under the trademark Alexa Fluor® 647 (Molecular Probes, Inc., Eugene OR).

Clause 89. The composition of any one of clauses 78-88, further comprising whole blood from a human patient.

Clause 90. A kit comprising:
  a first binding agent for CD59 conjugated with a first detectable moiety; and
  a second binding agent for CD163 conjugated with a second detectable moiety.

Clause 91. The kit of clause 90,
  wherein the first binding agent and second binding agent, are independently chosen from single chain variable fragments, antibody mimetics, antibody fragments, antibodies, monoclonal antibodies, and combinations thereof.

Clause 92. The kit of any one of clauses 90-91, wherein the first detectable moiety and second detectable moiety, are independently chosen from radioisotopes, stable isotopes, fluorophores, and combinations thereof.

Clause 93. A kit comprising:
  a monoclonal antibody for CD59 conjugated with a first fluorophore; and
  a monoclonal antibody for CD163 conjugated with a second fluorophore.

Clause 94. A kit comprising:
  a mouse anti-human IgG monoclonal antibody for CD59 conjugated with a first fluorophore; and
  a mouse anti-human IgG monoclonal antibody for CD163 conjugated with a second fluorophore.

Clause 95. The kit of any one of clauses 93-94, wherein the composition does not contain fluorescent dye sold under the trademark Alexa Fluor® 488 (Molecular Probes, Inc., Eugene OR).

Clause 96. The kit of any one of clauses 93-95, wherein the first fluorophore is R-phycoerythrin.

Clause 97. The kit of any one of clauses 93-96, wherein the second fluorophore is fluorescent dye sold under the trademark Alexa Fluor® 647 (Molecular Probes, Inc., Eugene OR).

Clause 98. A method of measuring relative expression of CD59 and CD163 in a human patient, comprising:
  obtaining a sample of whole blood from the human patient;
  contacting the sample with
    a first binding agent for CD59 conjugated with a first detectable moiety; and a second binding agent for CD163 conjugated with a second detectable moiety,
    to form bound CD59, and bound CD163,
  measuring the concentration of the first detectable moiety and the second detectable moiety,
  thereby determining the relative expression of CD59 and CD163.

Clause 99. The method of clause 98, wherein the measuring the concentration comprises measuring the concentration on leukocytes.

Clause 100. A method of measuring relative expression of CD59 and CD163 in a human patient, comprising:
  obtaining a sample of whole blood from the human patient;
  contacting the sample with
    a monoclonal antibody for CD59 conjugated with a first fluorophore; and
    a monoclonal antibody for CD163 conjugated with a second fluorophore,
    to form bound CD59 and bound CD163;
  measuring fluorescence of the first fluorophore and the second fluorophore, thereby determining the relative expression of CD59 and CD163.

Clause 101. A method of measuring relative expression of CD59 and CD163 in a human patient, comprising:
  obtaining a sample of whole blood from the human patient;
  contacting the sample with
    a mouse anti-human IgG monoclonal antibody for CD59 conjugated with a first fluorophore; and
    a mouse anti-human IgG monoclonal antibody for CD163 conjugated with a second fluorophore,
    to form bound CD59 and bound CD163;
  measuring fluorescence of the first fluorophore and the second fluorophore, thereby determining the relative expression of CD59 and CD163.

Clause 102. The methods of any one of clauses 100-101, wherein the relative expression of CD59 and CD163 is the relative expression of CD59 and CD163 on leukocytes.

Clause 103. A method for diagnosing AD in a human patient, comprising:
  obtaining a blood sample from the human patient;
  optionally storing the blood sample in ice;
  optionally testing the blood sample within three hours of obtaining the blood sample;
  reacting the blood sample with
    a mouse anti-human IgG monoclonal antibody for CD59 conjugated with a first fluorophore to obtain bound CD59;
    a mouse anti-human IgG monoclonal antibody for CD163 conjugated with a second fluorophore to obtain bound CD163;
  measuring a concentration of bound CD59 and a concentration of bound CD163 in the blood sample by fluorescence of the first fluorophore and the second fluorophore,
  observing an increase in the concentration of bound CD59 relative to a concentration range of CD59 in healthy humans;
  observing a decrease in the concentration of bound CD163 relative to a concentration range of CD163 in healthy humans;
  thereby diagnosing AD in the human patient.

Clause 104. The method of clause 103, wherein the measuring the concentration comprises measuring the concentration on leukocytes.

Clause 105. The method of any one of clauses 103-104, wherein the measuring the concentration of bound CD59 comprises measuring the mean fluorescence intensity of bound CD59.

Clause 106. The method of any one of clauses 103-105, wherein the measuring the concentration of bound CD163 comprises measuring the mean fluorescence intensity of bound CD163.

Clause 107. The method of any one of clauses 103-106, wherein the observing an increase in the concentration of bound CD59 comprises comparing a mean fluorescence intensity of bound CD59 for the human patient with a mean fluorescence intensity of bound CD59 for a pool of human participants who have <25CL as measured by amyloid PET imaging.

Clause 108. The method of clause 107, wherein the observing an increase in the concentration of bound CD59 comprises measuring an increase in mean fluorescence intensity of at least about 27%, at least about 30%, at least about 35%, at least about 40%, at least about 45%, at least about 50%, at least about 55%, at least about 60%, at least about 65%, at least about 70%, at least about 75%, or at least about 78% compared to a mean fluorescence intensity of bound CD59 for the pool of human patients who have <15CL as measured by amyloid PET imaging.

Clause 109. The method of any one of clauses 103-108, wherein the observing a decrease in the concentration of bound CD163 comprises comparing a mean fluorescence intensity of bound CD163 for the human patient with a mean fluorescence intensity of bound CD163 for a pool of human participants who have <25CL as measured by amyloid PET imaging.

Clause 110. The method of clause 109, wherein the observing a decrease in the concentration of bound CD163 comprises measuring a decrease in mean fluorescence intensity of at least about 11%, at least about 12%, at least about 13%, at least about 14%, at least about 15%, at least about 16%, at least about 17%, at least about 18%, or at least about 19% compared to a mean fluorescence intensity of bound CD163 for the pool of human patients who have <15CL as measured by amyloid PET imaging.

Clause 111. A method for determining the efficacy of an AD therapeutic candidate in a human patient, comprising:

(A) obtaining a first blood sample from the human patient;

optionally storing the first blood sample in ice;

optionally testing the first blood sample within three hours of obtaining the first blood sample;

reacting the first blood sample with a mouse anti-human IgG monoclonal antibody for CD59 conjugated with a first fluorophore to obtain first bound CD59;

a mouse anti-human IgG monoclonal antibody for CD163 conjugated with a second fluorophore to obtain first bound CD163;

measuring a first concentration of first bound CD59 and a first concentration of first bound CD163 in the first blood sample by fluorescence of the first fluorophore and second fluorophore;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with the mouse anti-human IgG monoclonal antibody for CD59 conjugated with the first fluorophore to obtain second bound CD59;

the mouse anti-human IgG monoclonal antibody for CD163 conjugated with the second fluorophore to obtain second bound CD163;

measuring a second concentration of second bound CD59 and a second concentration of second bound CD163 in the second blood sample by fluorescence of the first fluorophore and second fluorophore;

(D) observing a decrease from the first concentration of first bound CD59 to the second concentration of second bound CD59 in the human patient;

observing an increase from the first concentration of first bound CD163 to the second concentration of second bound CD163;

(E) thereby determining the efficacy of the AD therapeutic candidate in the human patient.

Clause 112. The method of clause 111, wherein the AD therapeutic candidate is a phagocytosis-promoting agent.

Clause 113. The method of clause 111, wherein the AD therapeutic candidate is a scavenger receptor agonist.

Clause 114. The method of any one of clauses 111-113, wherein the measuring the first concentration comprises measuring the first concentration on leukocytes, and the measuring the second concentration comprises measuring the second concentration on leukocytes.

Clause 115. A use of a binding agent for CD59 and a binding agent for CD163 for the diagnosis of AD in a human patient in need thereof.

Clause 116. The use of clause 115, wherein the binding agents are chosen from single chain variable fragments, antibody mimetics, antibody fragments, antibodies, monoclonal antibodies, and combinations thereof.

Clause 117. The use of any one of clauses 115-116, wherein the binding agent for CD59 is conjugated with a first detectable moiety, and the binding agent for CD163 is conjugated with a second detectable moiety.

Clause 118. The use of clause 117, wherein the first detectable moiety and the second detectable moiety are independently chosen from radioisotopes, stable isotopes, fluorophores, and combinations thereof.

Clause 119. A method for diagnosing AD in a human patient, comprising:

obtaining a blood sample from the human patient;

optionally storing the blood sample in ice;

optionally testing the blood sample within three hours of obtaining the blood sample;

reacting the blood sample with a mouse anti-human IgG monoclonal antibody for a scavenger receptor conjugated with a fluorophore to obtain bound scavenger receptor;

measuring a concentration of bound scavenger receptor in the blood sample by fluorescence of the fluorophore;

observing a decrease in the concentration of bound scavenger receptor relative to a concentration range of scavenger receptor in healthy humans;

thereby diagnosing AD in the human patient.

Clause 120. A method for diagnosing AD in a human patient, comprising:

obtaining a blood sample from the human patient;

optionally storing the blood sample in ice;

optionally testing the blood sample within three hours of obtaining the blood sample;

reacting the blood sample with a plurality of antibody-fluorophore conjugates, each antibody-fluorophore conjugate in the plurality comprising a mouse anti-human IgG monoclonal antibody for a scavenger receptor conjugated with a fluorophore;

thereby forming bound scavenger receptors;

measuring concentrations of the bound scavenger receptors in the blood sample by fluorescence of the fluorophores;

observing a decrease in the concentration of at least one bound scavenger receptor relative to a concentration range of a corresponding scavenger receptor in healthy humans;

thereby diagnosing AD in the human patient.

Clause 121. The method of any one of clauses 119-120, wherein the scavenger receptor is chosen from CD163, MerTK, CD18, and combinations thereof.

Clause 122. The method of any one of clauses 119-121, wherein the scavenger receptor is expressed on leukocytes.

Clause 123. A method for determining the efficacy of an AD therapeutic candidate in a human patient, comprising:

(A) obtaining a first blood sample from the human patient;

optionally storing the first blood sample in ice;

optionally testing the first blood sample within three hours of obtaining the first blood sample;

reacting the first blood sample with a first aliquot of a plurality of antibody-fluorophore conjugates, each antibody-fluorophore conjugate in the plurality comprising a mouse anti-human IgG monoclonal antibody for a scavenger receptor conjugated with a fluorophore;

thereby forming first bound scavenger receptors;

measuring first concentrations of the first bound scavenger receptors in the first blood sample by fluorescence of the fluorophores;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with a second aliquot of the plurality of antibody-fluorophore conjugates;

thereby forming second bound scavenger receptors;

measuring second concentrations of the second bound scavenger receptors in the second blood sample by fluorescence of the fluorophores;

(D) observing an increase from the first concentration of first bound scavenger receptors to the second concentration of second bound scavenger receptors in the human patient;

(E) thereby determining the efficacy of the AD therapeutic candidate in the human patient.

Clause 124. The method of clause 123, wherein the AD therapeutic candidate is a phagocytosis-promoting agent.

Clause 125. The method of clause 123, wherein the AD therapeutic candidate is a scavenger receptor agonist.

Clause 126. The method of any one of clauses 123-125, wherein the measuring first concentrations comprises measuring first concentrations on leukocytes, and the measuring second concentrations comprises measuring second concentrations on leukocytes.

Clause 127. The method of any one of clauses 123-126, wherein the scavenger receptor is chosen from CD163, MerTK, CD18, and combinations thereof.

Clause 128. A composition comprising:

a first binding agent for CD18 conjugated with a first detectable moiety.

Clause 129. The composition of clause 128, wherein the first binding agent is chosen from single chain variable fragments, antibody mimetics, antibody fragments, antibodies, monoclonal antibodies, and combinations thereof.

Clause 130. The composition of any one of clauses 128-129, wherein the first detectable moiety is chosen from radioisotopes, stable isotopes, fluorophores, and combinations thereof.

Clause 131. A composition comprising:

a monoclonal antibody for CD18 conjugated with a first fluorophore.

Clause 132. A composition comprising:

a mouse anti-human IgG monoclonal antibody for CD18 conjugated with a first fluorophore.

Clause 133. The composition of any one of clauses 131-132, further comprising whole blood from a human patient.

Clause 134. A kit comprising:

a first binding agent for CD18 conjugated with a first detectable moiety.

Clause 135. The kit of clause 134, wherein the first binding agent is chosen from single chain variable fragments, antibody mimetics, antibody fragments, antibodies, monoclonal antibodies, and combinations thereof.

Clause 136. The kit of any one of clauses 134-135, wherein the first detectable moiety is chosen from radioisotopes, stable isotopes, fluorophores, and combinations thereof.

Clause 137. A kit comprising:

a monoclonal antibody for CD18 conjugated with a first fluorophore.

Clause 138. A kit comprising:

a mouse anti-human IgG monoclonal antibody for CD18 conjugated with a first fluorophore.

Clause 139. A method of measuring relative expression of CD18 in a human patient, comprising:

obtaining a sample of whole blood from the human patient;

contacting the sample with a monoclonal antibody for CD18 conjugated with a first fluorophore, to form bound CD18;

measuring fluorescence of the first fluorophore, thereby determining the relative expression of CD18.

Clause 140. A method of measuring relative expression of CD18 in a human patient, comprising:

obtaining a sample of whole blood from the human patient;

contacting the sample with a mouse anti-human IgG monoclonal antibody for CD18 conjugated with a first fluorophore, to form bound CD18;

measuring fluorescence of the first fluorophore, thereby determining the relative expression of CD18.

Clause 141. The methods of any one of clauses 139-140, wherein the relative expression of CD18 is the relative expression of CD18 on leukocytes.

Clause 142. A method for diagnosing AD in a human patient, comprising:

obtaining a blood sample from the human patient;

optionally storing the blood sample in ice;

optionally testing the blood sample within three hours of obtaining the blood sample; reacting the blood sample with a mouse anti-human IgG monoclonal antibody for CD18 conjugated with a first fluorophore to obtain bound CD18;

measuring a concentration of bound CD18 in the blood sample by fluorescence of the first fluorophore;

observing a decrease in the concentration of bound CD18 relative to a concentration range of CD18 in healthy humans;

thereby diagnosing AD in the human patient.

Clause 143. The method of clause 142, wherein the measuring the concentration comprises measuring the concentration on leukocytes.

Clause 144. A use of a binding agent for CD18 for the diagnosis of AD in a human patient in need thereof.

Clause 145. The use of clause 144, wherein the binding agent is chosen from single chain variable fragments, antibody mimetics, antibody fragments, antibodies, monoclonal antibodies, and combinations thereof.

Clause 146. The use of any one of clauses 144-145, wherein the binding agent for CD18 is conjugated with a first detectable moiety.

Clause 147. The use of clause 146, wherein the first detectable moiety is chosen from radioisotopes, stable isotopes, fluorophores, and combinations thereof.

Clause 148. A method for determining the efficacy of an AD therapeutic candidate in a human patient, comprising:

(A) obtaining a first blood sample from the human patient;

optionally storing the first blood sample in ice;

optionally testing the first blood sample within three hours of obtaining the first blood sample;

reacting the first blood sample with a mouse anti-human IgG monoclonal antibody for CD18 conjugated with a first fluorophore to obtain first bound CD18;

measuring a first concentration of first bound CD18 in the first blood sample by fluorescence of the first fluorophore;

(B) administering the AD therapeutic candidate to the human patient;

(C) obtaining a second blood sample from the human patient;

optionally storing the second blood sample in ice;

optionally testing the second blood sample within three hours of obtaining the second blood sample;

reacting the second blood sample with the mouse anti-human IgG monoclonal antibody for CD18 conjugated with the first fluorophore to obtain second bound CD18;

measuring a second concentration of second bound CD18 in the second blood sample by fluorescence of the first fluorophore;

(D) observing an increase from the first concentration of first bound CD18 to the second concentration of second bound CD18;

(E) thereby determining the efficacy of the AD therapeutic candidate in the human patient.

Clause 149. The method of clause 148, wherein the AD therapeutic candidate is a phagocytosis-promoting agent.

Clause 150. The method of clause 148, wherein the AD therapeutic candidate is a scavenger receptor agonist.

Clause 151. The method of any one of clauses 148-150, wherein the measuring the first concentrations comprises measuring the first concentrations on leukocytes, and the measuring the second concentrations comprises measuring the second concentrations on leukocytes.

Clause 152. A composition comprising:

one or more first binding agents for one or more of CD33, CD35, CD36, CD59, CD91, P2X7, and RAGE conjugated with one or more first detectable moieties; and one or more second binding agents for one or more of CD18, CD163, and MerTK conjugated with one or more second detectable moieties.

Clause 153. A composition comprising:

one or more of monoclonal antibodies for one or more of CD33, CD35, CD36, CD59, CD91, P2X7, and RAGE conjugated with one or more first fluorophores; and one or more monoclonal antibodies for one or more of CD18, CD163, and MerTK conjugated with one or more second fluorophores.

Clause 154. The composition of any one of clauses 152-153, further comprising at least one anticoagulant.

Clause 155. The composition of any one of clauses 152-154, further comprising whole blood from a human patient.

Clause 156. A kit comprising:

one or more first binding agents for one or more of CD33, CD35, CD36, CD59, CD91, P2X7, and RAGE conjugated with one or more first detectable moieties; and one or more second binding agents for one or more of CD18, CD163, and MerTK conjugated with one or more second detectable moieties.

Clause 157. A kit comprising:

one or more of monoclonal antibodies for one or more of CD33, CD35, CD36, CD59, CD91, P2X7, and RAGE conjugated with one or more first fluorophores; and one or more monoclonal antibodies for one or more of CD18, CD163, and MerTK conjugated with one or more second fluorophores.

Clause 158. A composition comprising:

one or more of monoclonal antibodies for one or more of scavenger receptors and their regulators CD163, CD91, P2X7, MerTK CD59, CD18 conjugated with different fluorophores, and the fluorophores have different but compatible emission and excitation spectrum in multiple-colour flow cytometry analysis.

Clause 159. A composition comprising:

one or more first binding agents for one or more of scavenger receptors and their regulators CD163, CD91, P2X7, MerTK CD59, CD18 conjugated with different first detectable moieties.

Clause 160. A kit comprising:

one or more of monoclonal antibodies for one or more of CD18 and CD59 conjugated with one or more first fluorophores.

Clause 161. A kit comprising:

one or more first binding agents for one or more of, CD18 and CD59, conjugated with one or more first detectable moieties.

Clause 162. A composition comprising:

one or more of monoclonal antibodies for one or more of CD91, CD163, P2X7, and MerTK conjugated with one or more first fluorophores.

Clause 163. A composition comprising:

one or more first binding agents for one or more of CD91, CD163, P2X7, and MerTK conjugated with one or more first detectable moieties.

Clause 164. A kit comprising:

one or more of monoclonal antibodies for one or more of CD91, CD163, P2X7, and MerTK conjugated with one or more first fluorophores.

Clause 165. A kit comprising:

one or more first binding agents for one or more of CD91, CD163, P2X7, and MerTK conjugated with one or more first detectable moieties.

Clause 166. A composition comprising:

one or more of monoclonal antibodies for one or more of CD91, CD163, P2X7, and MerTK conjugated with one or more first fluorophores;

one or more of monoclonal antibodies for one or more of CD18 and CD59 conjugated with one or more second fluorophores.

Clause 167. A composition comprising:

one or more first binding agents for one or more of CD91, CD163, P2X7, and MerTK conjugated with one or more first detectable moieties;

one or more of second binding agents for one or more of CD18 and CD59 conjugated with one or more second detectable moieties.

Clause 168. A kit comprising:

one or more of monoclonal antibodies for one or more of CD91, CD163, P2X7, and MerTK conjugated with one or more first fluorophores;

one or more of monoclonal antibodies for one or more of CD18 and CD59, conjugated with one or more second fluorophores.

Clause 169. A kit comprising:

one or more first binding agents for one or more of CD91, CD163, P2X7, and MerTK conjugated with one or more first detectable moieties;

one or more of second binding agents for one or more of CD18 and CD59 conjugated with one or more second detectable moieties.

Clause 170. A kit comprising:

a first binding agent for one or more of CD163, CD91, and MerTK, conjugated with a first detectable moiety.

Clause 171. The kit of clause 170, wherein the wherein the first binding agent is chosen from single chain variable fragments, antibody mimetics, antibody fragments, antibodies, monoclonal antibodies, and combinations thereof.

Clause 172. The kit of any one of clauses 170-171, wherein the first detectable moiety is chosen from radioisotopes, stable isotopes, fluorophores, and combinations thereof.

Clause 173. A composition comprising:

a first binding agent for CD59 conjugated with a first detectable moiety; and a second binding agent for CD163 conjugated with a second detectable moiety.

Clause 174. The composition of clause 173, wherein the first binding agent and second binding agent are independently chosen from single chain variable fragments, antibody mimetics, antibody fragments, antibodies, monoclonal antibodies, and combinations thereof.

Clause 175. The composition of any one of clauses 173-174, wherein the first detectable moiety and second detectable moiety are chosen from radioisotopes, stable isotopes, fluorophores, and combinations thereof.

Clause 176. A composition comprising:

a monoclonal antibody for CD59 conjugated with a first fluorophore; and a monoclonal antibody for CD163 conjugated with a second fluorophore.

Clause 177. A composition comprising:

a mouse anti-human IgG monoclonal antibody for CD59 conjugated with a first fluorophore; and a mouse anti-human IgG monoclonal antibody for CD163 conjugated with a second fluorophore.

Clause 178. The composition of any one of clauses 176-177, further comprising at least one anticoagulant.

Clause 179. The composition of any one of clauses 176-178, wherein the at least one anticoagulant comprises ethylene diamine tetraacetic acid, at least one salt thereof, citric acid, at least one salt thereof, or a combination of any of the foregoing.

Clause 180. The composition of any one of clauses 176-179, further comprising bovine serum albumin and sodium azide.

Clause 181. The composition of any one of clauses 176-180, further comprising phosphate buffered saline, gelatin, and sodium azide.

Clause 182. The composition of any one of clauses 176-181, wherein the composition does not contain fluorescent dye sold under the trademark Alexa Fluor® 488 (Molecular Probes, Inc., Eugene OR).

Clause 183. The composition of any one of clauses 176-182, wherein the first fluorophore is R-phycoerythrin.

Clause 184. The composition of any one of clauses 176-183, wherein the second fluorophore is fluorescent dye sold under the trademark Alexa Fluor® 647 (Molecular Probes, Inc., Eugene OR).

Clause 185. The composition of any one of clauses 176-184, further comprising whole blood from a human patient.

Clause 186. A kit comprising:

a first binding agent for CD59 conjugated with a first detectable moiety; and a second binding agent for CD163 conjugated with a second detectable moiety.

Clause 187. The kit of clause 186, wherein the first binding agent and second binding agent are independently chosen from single chain variable fragments, antibody mimetics, antibody fragments, antibodies, monoclonal antibodies, and combinations thereof.

Clause 188. The kit of any one of clauses 186-187, wherein the first detectable moiety and second detectable moiety are independently chosen from radioisotopes, stable isotopes, fluorophores, and combinations thereof.

Clause 189. A kit comprising:

a monoclonal antibody for CD59 conjugated with a first fluorophore; and a monoclonal antibody for CD163 conjugated with a second fluorophore.

Clause 190. A kit comprising:

a mouse anti-human IgG monoclonal antibody for CD59 conjugated with a first fluorophore; and a mouse anti-human IgG monoclonal antibody for CD163 conjugated with a second fluorophore.

Clause 191. The kit of any one of clauses 189-190, wherein the kit does not contain fluorescent dye sold under the trademark Alexa Fluor® 488 (Molecular Probes, Inc., Eugene OR).

Clause 192. The kit of any one of clauses 189-191, wherein the first fluorophore is R-phycoerythrin.

Clause 193. The kit of any one of clauses 189-192, wherein the second fluorophore is fluorescent dye sold under the trademark Alexa Fluor® 647 (Molecular Probes, Inc., Eugene OR).

Clause 194. A use of a binding agent for CD59 and a binding agent for CD163 for the diagnosis of AD in a human patient in need thereof.

Clause 195. The use of clause 194, wherein the binding agents are chosen from single chain variable fragments, antibody mimetics, antibody fragments, antibodies, monoclonal antibodies, and combinations thereof.

Clause 196. The use of any one of clauses 194-195, wherein the binding agent for CD59 is conjugated with a first detectable moiety, and the binding agent for CD163 is conjugated with a second detectable moiety.

Clause 197. The use of clause 196, wherein the first detectable moiety and the second detectable moiety are independently chosen from radioisotopes, stable isotopes, fluorophores, and combinations thereof.

Clause 198. A composition comprising:
a first binding agent for CD91 conjugated with a first detectable moiety;
a second binding agent for CD59 conjugated with a second detectable moiety; and
a third binding agent for CD163 conjugated with a third detectable moiety.

Clause 199. The composition of clause 198,
wherein the first binding agent, second binding agent, and third binding agent, are independently chosen from single chain variable fragments, antibody mimetics, antibody fragments, antibodies, monoclonal antibodies, and combinations thereof.

Clause 200. The composition of any one of clauses 198-199, wherein the first detectable moiety, second detectable moiety, and third detectable moiety are independently chosen from radioisotopes, stable isotopes, fluorophores, and combinations thereof.

Clause 201. A composition comprising:
a monoclonal antibody for CD91 conjugated with a first fluorophore;
a monoclonal antibody for CD59 conjugated with a second fluorophore; and
a monoclonal antibody for CD163 conjugated with a third fluorophore.

Clause 202. A composition comprising:
a mouse anti-human IgG monoclonal antibody for CD91 conjugated with a first fluorophore;
a mouse anti-human IgG monoclonal antibody for CD59 conjugated with a second fluorophore; and
a mouse anti-human IgG monoclonal antibody for CD163 conjugated with a third fluorophore.

Clause 203. The composition of any one of clauses 201-202, further comprising at least one anticoagulant.

Clause 204. The composition of any one of clauses 201-203, wherein the at least one anticoagulant comprises ethylene diamine tetraacetic acid, at least one salt thereof, citric acid, at least one salt thereof, or a combination of any of the foregoing.

Clause 205. The composition of any one of clauses 201-204, further comprising bovine serum albumin and sodium azide.

Clause 206. The composition of any one of clauses 201-205, further comprising phosphate buffered saline, gelatin, and sodium azide.

Clause 207. The composition of any one of clauses 201-206, wherein the first fluorophore is fluorescein isothiocyanate.

Clause 208. The composition of any one of clauses 201-207, wherein the composition does not contain fluorescent dye sold under the trademark Alexa Fluor® 488 (Molecular Probes, Inc., Eugene OR).

Clause 209. The composition of any one of clauses 201-208, wherein the second fluorophore is R-phycoerythrin.

Clause 210. The composition of any one of clauses 201-209, wherein the third fluorophore is fluorescent dye sold under the trademark Alexa Fluor® 647 (Molecular Probes, Inc., Eugene OR).

Clause 211. The composition of any one of clauses 201-210, further comprising whole blood from a human patient.

Clause 212. A kit comprising:
a first binding agent for CD91 conjugated with a first detectable moiety;
a second binding agent for CD59 conjugated with a second detectable moiety; and
a third binding agent for CD163 conjugated with a third detectable moiety.

Clause 213. The kit of clause 212,
wherein the first binding agent, second binding agent, and third binding agent are independently chosen from single chain variable fragments, antibody mimetics, antibody fragments, antibodies, monoclonal antibodies, and combinations thereof.

Clause 214. The kit of any one of clauses 212-213, wherein the first detectable moiety, second detectable moiety, and third detectable moiety are independently chosen from radioisotopes, stable isotopes, fluorophores, and combinations thereof.

Clause 215. A kit comprising:
a monoclonal antibody for CD91 conjugated with a first fluorophore;
a monoclonal antibody for CD59 conjugated with a second fluorophore; and
a monoclonal antibody for CD163 conjugated with a third fluorophore.

Clause 216. A kit comprising:
a mouse anti-human IgG monoclonal antibody for CD91 conjugated with a first fluorophore;
a mouse anti-human IgG monoclonal antibody for CD59 conjugated with a second fluorophore; and
a mouse anti-human IgG monoclonal antibody for CD163 conjugated with a third fluorophore.

Clause 217. The kit of any one of clauses 215-216, wherein the first fluorophore is fluorescein isothiocyanate.

Clause 218. The kit of any one of clauses 215-217, wherein the kit does not contain fluorescent dye sold under the trademark Alexa Fluor® 488 (Molecular Probes, Inc., Eugene OR).

Clause 219. The kit of any one of clauses 215-218, wherein the second fluorophore is R-phycoerythrin.

Clause 220. The kit of any one of clauses 215-219, wherein the third fluorophore is fluorescent dye sold under the trademark Alexa Fluor® 647 (Molecular Probes, Inc., Eugene OR).

Clause 221. A use of a binding agent for CD91, a binding agent for CD59, and a binding agent for CD163 for the diagnosis of AD in a human patient in need thereof.

Clause 222. The use of clause 221, wherein the binding agents are chosen from single chain variable fragments, antibody mimetics, antibody fragments, antibodies, monoclonal antibodies, and combinations thereof.

Clause 223. The use of any one of clauses 221-222, wherein the binding agent for CD91 is conjugated with a first detectable moiety, the binding agent for CD59 is conjugated with a second detectable moiety, and the binding agent for CD163 is conjugated with a third detectable moiety.

Clause 224. The use of clause 223, wherein the first detectable moiety, the second detectable moiety, and the third detectable moiety, are independently chosen from radioisotopes, stable isotopes, fluorophores, and combinations thereof.

Clause 225. A composition comprising:

a first binding agent for CD91 conjugated with a first detectable moiety;

a second binding agent for CD59 conjugated with a second detectable moiety; and a third binding agent for CD163 conjugated with a third detectable moiety.

Clause 226. The composition of clause 225, wherein the first binding agent, second binding agent, and third binding agent are independently chosen from single chain variable fragments, antibody mimetics, antibody fragments, antibodies, monoclonal antibodies, and combinations thereof.

Clause 227. The composition of any one of clauses 225-226, wherein the first detectable moiety, second detectable moiety, and third detectable moiety are independently chosen from radioisotopes, stable isotopes, fluorophores, and combinations thereof.

Clause 228. The composition of clause 225, wherein the first binding agent for CD91 is a monoclonal antibody for CD91, and the first detectable moiety is a first fluorophore;

the second binding agent for CD59 is a monoclonal antibody for CD59, and the second detectable moiety is a second fluorophore; and the third binding agent for CD163 is a monoclonal antibody for CD163, and the third detectable moiety is a third fluorophore.

Clause 229. The composition of clause 228, wherein the monoclonal antibody for CD91 is a mouse anti-human IgG monoclonal antibody for CD91;

the monoclonal antibody for CD59 is a mouse anti-human IgG monoclonal antibody for CD59; and the monoclonal antibody for CD163 is a mouse anti-human IgG monoclonal antibody for CD163.

Clause 230. The composition of any one of clauses 228-229, wherein the first fluorophore is fluorescein isothiocyanate.

Clause 231. The composition of any one of clauses 228-230, wherein the second fluorophore is R-phycoerythrin.

Clause 232. The composition of any one of clauses 228-231, wherein the third fluorophore is fluorescent dye sold under the trademark Alexa Fluor® 647 (Molecular Probes, Inc., Eugene OR).

Clause 233. The composition of any one of clauses 225-232, further comprising whole blood from a human patient.

Clause 234. The composition of any one of clauses 225-233 further comprising at least one anticoagulant.

Clause 235. A method for diagnosing AD in a human patient, comprising:

obtaining a blood sample from the human patient;

optionally storing the blood sample in ice;

optionally testing the blood sample within three hours of obtaining the blood sample;

reacting the blood sample with a mouse anti-human IgG monoclonal antibody for CD91 conjugated with a first fluorophore to obtain bound CD91;

a mouse anti-human IgG monoclonal antibody for CD59 conjugated with a second fluorophore to obtain bound CD59;

a mouse anti-human IgG monoclonal antibody for CD163 conjugated with a third fluorophore to obtain bound CD163;

measuring a concentration of bound CD91, a concentration of bound CD59, and a concentration of bound CD163 in the blood sample by fluorescence of the first fluorophore, the second fluorophore, and the third fluorophore;

observing an increase in the concentration of bound CD91 relative to a concentration range of CD91 in healthy humans;

observing an increase in the concentration of bound CD59 relative to a concentration range of CD59 in healthy humans;

observing a decrease in the concentration of bound CD163 relative to a concentration range of CD163 in healthy humans;

thereby diagnosing AD in the human patient.

As previously stated, detailed embodiments of the present invention are disclosed herein; however, it is to be understood that the disclosed embodiments are merely exemplary of the invention that may be embodied in various forms. It will be appreciated that many modifications and other variations stand within the intended scope of this invention as claimed below. Furthermore, the foregoing description of various embodiments does not necessarily imply exclusion. For example, "some" embodiments may include all or part of "other" and "further" embodiments within the scope of this invention. In addition, "a" does not mean "one and only one;" "a" can mean "one and more than one."

We claim:

1. A kit for diagnosing and prognosing Alzheimer's Disease (AD) in a blood sample obtained from a subject, comprising:

(i) a panel of biomarkers consisting of:

a first binding agent for CD91 on a blood cell in the blood sample, wherein the first binding agent is conjugated with a first detectable moiety;

a second binding agent for CD59 on a blood cell in the blood sample, wherein the second binding agent is conjugated with a second detectable moiety;

a third binding agent for CD163 on a blood cell in the blood sample, wherein the third binding agent is conjugated with a third detectable moiety; and a fourth binding agent for CD11c on a blood cell in the blood sample, wherein the fourth binding agent is conjugated with a fourth detectable moiety;

(ii) an anticoagulant; and (iii) instructions for use;

wherein the first binding agent, the second binding agent, the third binding agent, and the fourth binding agent are independently chosen from single chain variable fragments, antibody mimetics, antibody fragments, antibodies, monoclonal antibodies, and combinations thereof.

2. The kit of claim 1, wherein the first detectable moiety, the second detectable moiety, the third detectable moiety, and the fourth detectable moiety are independently chosen from radioisotopes, stable isotopes, fluorophores, and combinations thereof.

3. The kit of claim 1, wherein the first binding agent for CD91 is a monoclonal antibody for CD91, and the first detectable moiety is a first fluorophore;

the second binding agent for CD59 is a monoclonal antibody for CD59, and the second detectable moiety is a second fluorophore;

the third binding agent for CD163 is a monoclonal antibody for CD163, and the third detectable moiety is a third fluorophore; and the fourth binding agent for CD11c is a monoclonal antibody for CD11c, and the fourth detectable moiety is a fourth fluorophore.

4. The kit of claim 3, wherein the monoclonal antibody for CD91 is a mouse anti-human IgG monoclonal antibody for CD91;

the monoclonal antibody for CD59 is a mouse anti-human IgG monoclonal antibody for CD59;

the monoclonal antibody for CD163 is a mouse anti-human IgG monoclonal antibody for CD163; and the monoclonal antibody for CD11c is a mouse anti-human IgG monoclonal antibody for CD11c.

5. The kit of claim 2, wherein the fluorophores comprise fluorescein isothiocyanate, R-phycoerythrin, fluorescent dye 647, or combinations thereof.

6. The kit of claim 1, further comprising a blood collection tube.

7. The kit of claim 1, wherein the anticoagulant comprises ethylene diamine tetraacetic acid, citric acid, or a combination thereof.

8. The kit of claim 1, further comprising sodium azide.

9. The kit of claim 1, further comprising a control blood sample obtained from a cognitively normal (CN) human subject having a negative Aβ-PET status.

10. A kit for diagnosing and prognosing Alzheimer's Disease (AD) in a blood sample obtained from a subject, comprising:

(i) a panel of biomarkers consisting of:

a first binding agent for CD91 on a blood cell in the blood sample, wherein the first binding agent is conjugated with a first detectable moiety;

a second binding agent for CD59 on a blood cell in the blood sample, wherein the second binding agent is conjugated with a second detectable moiety;

a third binding agent for CD163 on a blood cell in the blood sample, wherein the third binding agent is conjugated with a third detectable moiety; and a fourth binding agent for CD11c on a blood cell in the blood sample, wherein the fourth binding agent is conjugated with a fourth detectable moiety;

a fifth binding agent for CD14 on a blood cell in the blood sample, wherein the fifth binding agent is conjugated with a fifth detectable moiety; and a sixth binding agent for CD16 on a blood cell in the blood sample, wherein the sixth binding agent is conjugated with a sixth detectable moiety;

(ii) an anticoagulant; and (iii) instructions for use;

wherein the first binding agent, the second binding agent, the third binding agent, and the fourth binding agent are independently chosen from single chain variable fragments, antibody mimetics, antibody fragments, antibodies, monoclonal antibodies, and combinations thereof.

11. The kit of claim 10, wherein the first binding agent for CD91 is a monoclonal antibody for CD91, and the first detectable moiety is a first fluorophore;

the second binding agent for CD59 is a monoclonal antibody for CD59, and the second detectable moiety is a second fluorophore;

the third binding agent for CD163 is a monoclonal antibody for CD163, and the third detectable moiety is a third fluorophore;

the fourth binding agent for CD11c is a monoclonal antibody for CD11c, and the fourth detectable moiety is a fourth fluorophore;

the fifth binding agent for CD14 is a monoclonal antibody for CD14, and the fifth detectable moiety is a fifth fluorophore; and the sixth binding agent for CD16 is a monoclonal antibody for CD16, and the sixth detectable moiety is a sixth fluorophore.

12. The kit of claim 11, wherein the monoclonal antibody for CD91 is a mouse anti-human IgG monoclonal antibody for CD91;

the monoclonal antibody for CD59 is a mouse anti-human IgG monoclonal antibody for CD59;

the monoclonal antibody for CD163 is a mouse anti-human IgG monoclonal antibody for CD163;

the monoclonal antibody for CD11c is a mouse anti-human IgG monoclonal antibody for CD11c;

the monoclonal antibody for CD14 is a mouse anti-human IgG monoclonal antibody for CD14; and the monoclonal antibody for CD16 is a mouse anti-human IgG monoclonal antibody for CD16.

13. The kit of claim 10, wherein the first detectable moiety, the second detectable moiety, the third detectable moiety, the fourth detectable moiety, the fifth detectable moiety, and the sixth detectable moiety are independently chosen from radioisotopes, stable isotopes, fluorophores, and combinations thereof.

14. The kit of claim 13, wherein the fluorophores comprise fluorescein isothiocyanate, R-phycoerythrin, fluorescent dye 647, or combinations thereof.

15. The kit of claim 10, wherein the first detectable moiety, the second detectable moiety, the third detectable moiety, the fourth detectable moiety, the fifth detectable moiety, and the sixth detectable moiety are distinguishable from each other for quantitative assessment.

16. The kit of claim 1, further comprising an IgG isotype control.

17. The kit of claim 1, further comprising bovine serum albumin.

18. The kit of claim 1, further comprising phosphate buffered saline and gelatin.

19. The kit of claim 1, wherein the first detectable moiety, the second detectable moiety, the third detectable moiety, and the fourth detectable moiety are distinguishable from each other for quantitative assessment.

20. The kit of claim 1, wherein the first binding agent for CD91, the second binding agent for CD59, the third binding agent for CD163, and the fourth binding agent for CD11c are contained in a FACS tube in a pre-mixture.

21. A kit for diagnosing and prognosing Alzheimer's Disease (AD) in a blood sample obtained from a subject, comprising:

(i) a panel of biomarkers consisting of:

a first binding agent for CD91 on a blood cell in the blood sample, wherein the first binding agent is conjugated with a first detectable moiety;

a second binding agent for CD59 on a blood cell in the blood sample, wherein the second binding agent is conjugated with a second detectable moiety;

a third binding agent for CD163 on a blood cell in the blood sample, wherein the third binding agent is conjugated with a third detectable moiety; and a fourth binding agent for CD11c on a blood cell in the blood sample, wherein the fourth binding agent is conjugated with a fourth detectable moiety;

a fifth binding agent for CD14 on a blood cell in the blood sample, wherein the fifth binding agent is conjugated with a fifth detectable moiety; and a sixth binding agent for CD16 on a blood cell in the blood sample, wherein the sixth binding agent is conjugated with a sixth detectable moiety;

a seventh binding agent for CD11b on a blood cell in the blood sample, wherein the seventh binding agent is conjugated with a seventh detectable moiety;

an eighth binding agent for CD3 on a blood cell in the blood sample, wherein the eighth binding agent is conjugated with a eighth detectable moiety;

(ii) an anticoagulant; and (iii) instructions for use;

wherein the first binding agent, the second binding agent, the third binding agent, and the fourth binding agent are independently chosen from single chain variable fragments, antibody mimetics, antibody fragments, antibodies, monoclonal antibodies, and combinations thereof.

22. The kit of claim 21, wherein the first detectable moiety, the second detectable moiety, the third detectable moiety, the fourth detectable moiety, the fifth detectable moiety, the sixth detectable moiety, the seventh detectable moiety, and the eighth detectable moiety are independently chosen from radioisotopes, stable isotopes, fluorophores, and combinations thereof.

23. The kit of claim 21, wherein the first binding agent for CD91 is a monoclonal antibody for CD91, and the first detectable moiety is a first fluorophore;

the second binding agent for CD59 is a monoclonal antibody for CD59, and the second detectable moiety is a second fluorophore;

the third binding agent for CD163 is a monoclonal antibody for CD163, and the third detectable moiety is a third fluorophore;

the fourth binding agent for CD11c is a monoclonal antibody for CD11c, and the fourth detectable moiety is a fourth fluorophore;

the fifth binding agent for CD14 is a monoclonal antibody for CD14, and the fifth detectable moiety is a fifth fluorophore;

the sixth binding agent for CD16 is a monoclonal antibody for CD16, and the sixth detectable moiety is a sixth fluorophore;

the seventh binding agent for CD11b is a monoclonal antibody for CD11b, and the seventh detectable moiety is a seventh fluorophore; and the eighth binding agent for CD3 is a monoclonal antibody for CD3, and the eighth detectable moiety is an eighth fluorophore.

24. The kit of claim 21, wherein the first detectable moiety, the second detectable moiety, the third detectable moiety, the fourth detectable moiety, the fifth detectable moiety, the sixth detectable moiety, the seventh detectable moiety, and the eighth detectable moiety are distinguishable from each other for quantitative assessment.

* * * * *